(12) United States Patent
Timm et al.

(10) Patent No.: US 12,059,275 B2
(45) Date of Patent: *Aug. 13, 2024

(54) ROBOTIC ARM CART AND USES THEREFOR

(71) Applicants: Verb Surgical Inc., Santa Clara, CA (US); CILAG GMBH INTERNATIONAL, Zug (CH)

(72) Inventors: Richard William Timm, Cincinnati, OH (US); David James Cagle, Belmont, CA (US); Seung Mo Lim, Santa Cruz, CA (US); Jacob Spencer Gee, Cincinnati, OH (US); Omar J. Vakharia, Palo Alto, CA (US); Clinton Denlinger, Cincinnati, OH (US)

(73) Assignees: Verb Surgical Inc., Santa Clara, CA (US); CILAG GMBH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,826

(22) Filed: Mar. 27, 2023

(65) Prior Publication Data

US 2023/0310109 A1 Oct. 5, 2023

Related U.S. Application Data

(63) Continuation of application No. 17/021,860, filed on Sep. 15, 2020, now Pat. No. 11,622,830, which is a
(Continued)

(51) Int. Cl.
*A61B 50/13* (2016.01)
*A61B 90/50* (2016.01)
(Continued)

(52) U.S. Cl.
CPC .............. *A61B 50/13* (2016.02); *A61B 90/50* (2016.02); *A61B 90/57* (2016.02); *B25J 9/0009* (2013.01);
(Continued)

(58) Field of Classification Search
CPC ......... A61B 50/13; A61B 90/50; A61B 90/57; B25J 9/0009; B62B 3/02
(Continued)

(56) References Cited

U.S. PATENT DOCUMENTS 5,351,676 A * 10/1994 Putman .................... B25J 9/042
600/117
5,876,325 A 3/1999 Mizuno et al.
(Continued)

FOREIGN PATENT DOCUMENTS

AU 2020260428 A1 11/2020
CA 2913943 A1 12/2014
(Continued)

OTHER PUBLICATIONS

Notice of Reason for Refusal for Japanese Application No. 2019-563190; Oct. 22, 2020; 7pp.
(Continued)

*Primary Examiner* — Todd M Epps
(74) *Attorney, Agent, or Firm* — Aikin & Gallant, LLP

(57) ABSTRACT

In some embodiments, an apparatus can include a robotic arm cart for transporting, delivering, and securing robotic arms to a surgical table having a table top. The arm cart can include an arm container and a base. The arm container can be configured to receive and contain one or more robotic arms. The arm cart can include a first coupling member configured to engage with a second coupling member associated with a surgical table such that, when the first coupling member is engaged with the second coupling member, the
(Continued)

one or more robotic arms can be releasably coupled with the surgical table. The arm cart can provide for movement of the one or more robotic arms in at least one of a lateral, longitudinal, or vertical direction relative to the table top prior to the securement of the one or more robotic arms to the surgical table.

20 Claims, 36 Drawing Sheets

Related U.S. Application Data continuation of application No. 15/785,341, filed on Oct. 16, 2017, now Pat. No. 10,792,119.

(60) Provisional application No. 62/509,611, filed on May 22, 2017.

(51) Int. Cl.
  *A61B 90/57* (2016.01)
  *B25J 9/00* (2006.01)
  *B62B 3/02* (2006.01)
  *A61B 34/30* (2016.01)

(52) U.S. Cl.
  CPC ............... *B62B 3/02* (2013.01); *A61B 34/30* (2016.02); *A61B 2090/5025* (2016.02); *A61B 2090/571* (2016.02); *A61B 2560/0437* (2013.01)

(58) Field of Classification Search
  USPC ........................................ 248/645
  See application file for complete search history.

(56) References Cited

U.S. PATENT DOCUMENTS

| | | |
|---|---|---|
| 5,878,193 A | 3/1999 | Wang et al. |
| 6,132,368 A | 10/2000 | Cooper |
| 6,246,200 B1 * | 6/2001 | Blumenkranz ......... A61B 34/70 318/568.25 |
| 6,264,219 B1 | 7/2001 | Smith |
| 6,330,890 B1 | 12/2001 | Ekman |
| 6,331,181 B1 | 12/2001 | Tierney et al. |
| 6,346,072 B1 | 2/2002 | Cooper |
| 6,450,978 B1 | 9/2002 | Brosseau et al. |
| 6,451,027 B1 | 9/2002 | Cooper et al. |
| 6,535,756 B1 | 3/2003 | Simon et al. |
| 6,587,750 B2 | 7/2003 | Gerbi et al. |
| 6,608,628 B1 | 8/2003 | Ross et al. |
| 6,659,939 B2 | 12/2003 | Moll et al. |
| 6,768,496 B2 | 7/2004 | Bieger et al. |
| 6,788,018 B1 | 9/2004 | Blumenkranz |
| 6,866,671 B2 | 3/2005 | Tierney et al. |
| 6,920,347 B2 | 7/2005 | Simon et al. |
| 6,962,581 B2 | 11/2005 | Thoe |
| 6,995,744 B1 | 2/2006 | Moore et al. |
| 7,008,362 B2 | 3/2006 | Fitzgibbon |
| 7,012,203 B2 | 3/2006 | Hanson et al. |
| 7,048,745 B2 | 5/2006 | Tierney et al. |
| 7,206,627 B2 | 4/2007 | Abovitz et al. |
| 7,217,269 B2 | 5/2007 | El-Galley et al. |
| 7,277,120 B2 | 10/2007 | Gere et al. |
| 7,317,955 B2 | 1/2008 | Mcgreevy |
| 7,331,967 B2 | 2/2008 | Lee et al. |
| 7,357,774 B2 | 4/2008 | Cooper |
| 7,369,116 B2 | 5/2008 | Logue |
| 7,379,790 B2 | 5/2008 | Toth et al. |
| 7,498,532 B2 | 3/2009 | Kuhner et al. |
| 7,524,320 B2 | 4/2009 | Tierney et al. |
| 7,554,526 B2 | 6/2009 | Logue |
| 7,594,912 B2 | 9/2009 | Cooper et al. |
| 7,666,191 B2 | 2/2010 | Orban et al. |
| 7,699,855 B2 | 4/2010 | Anderson et al. |
| 7,727,244 B2 | 6/2010 | Orban et al. |
| 7,768,702 B2 | 8/2010 | Hirose et al. |
| 7,781,941 B2 | 8/2010 | Horvath et al. |
| 7,783,133 B2 | 8/2010 | Dunki-Jacobs et al. |
| 7,789,874 B2 | 9/2010 | Yu et al. |
| 7,789,875 B2 | 9/2010 | Brock et al. |
| 7,819,885 B2 | 10/2010 | Cooper |
| 7,840,042 B2 | 11/2010 | Kriveshko et al. |
| 7,843,158 B2 | 11/2010 | Prisco |
| 7,853,305 B2 | 12/2010 | Simon et al. |
| 7,865,266 B2 | 1/2011 | Moll et al. |
| 7,883,458 B2 | 2/2011 | Hamel |
| 7,907,166 B2 | 3/2011 | Lamprecht et al. |
| 7,922,439 B2 | 4/2011 | Kato |
| 7,947,050 B2 | 5/2011 | Lee et al. |
| 7,955,322 B2 | 6/2011 | Devengenzo et al. |
| 7,983,793 B2 | 7/2011 | Toth et al. |
| 8,004,229 B2 | 8/2011 | Nowlin et al. |
| 8,062,288 B2 | 11/2011 | Cooper et al. |
| 8,079,950 B2 | 12/2011 | Stern et al. |
| 8,086,008 B2 | 12/2011 | Coste-Maniere et al. |
| 8,095,200 B2 | 1/2012 | Quaid, III |
| 8,100,133 B2 | 1/2012 | Mintz et al. |
| 8,105,338 B2 | 1/2012 | Anderson et al. |
| 8,120,301 B2 | 2/2012 | Goldberg et al. |
| 8,126,114 B2 | 2/2012 | Naylor et al. |
| 8,131,031 B2 | 3/2012 | Lloyd |
| 8,142,447 B2 | 3/2012 | Cooper et al. |
| 8,147,503 B2 | 4/2012 | Zhao et al. |
| 8,155,479 B2 | 4/2012 | Hoffman et al. |
| 8,190,238 B2 | 5/2012 | Moll et al. |
| 8,202,278 B2 | 6/2012 | Orban et al. |
| 8,206,406 B2 | 6/2012 | Orban, III |
| 8,256,319 B2 | 9/2012 | Cooper et al. |
| 8,332,072 B1 | 12/2012 | Schaible et al. |
| 8,343,096 B2 | 1/2013 | Kirschenman et al. |
| 8,391,954 B2 | 3/2013 | Quaid, III |
| 8,395,342 B2 | 3/2013 | Prisco |
| 8,398,541 B2 | 3/2013 | Dimaio et al. |
| 8,418,073 B2 | 4/2013 | Mohr et al. |
| 8,469,947 B2 | 6/2013 | Devengenzo et al. |
| 8,473,031 B2 | 6/2013 | Nixon et al. |
| 8,496,647 B2 | 7/2013 | Blumenkranz et al. |
| 8,504,136 B1 | 8/2013 | Sun et al. |
| 8,506,555 B2 | 8/2013 | Ruiz Morales |
| 8,508,173 B2 | 8/2013 | Goldberg et al. |
| 8,521,331 B2 | 8/2013 | Itkowitz |
| 8,527,094 B2 | 9/2013 | Kumar et al. |
| 8,541,970 B2 | 9/2013 | Nowlin et al. |
| 8,562,594 B2 | 10/2013 | Cooper et al. |
| 8,594,841 B2 | 11/2013 | Zhao et al. |
| 8,600,551 B2 | 12/2013 | Itkowitz et al. |
| 8,620,473 B2 | 12/2013 | Diolaiti et al. |
| 8,624,537 B2 | 1/2014 | Nowlin et al. |
| 8,628,518 B2 | 1/2014 | Blumenkranz et al. |
| 8,634,957 B2 | 1/2014 | Toth et al. |
| 8,638,056 B2 | 1/2014 | Goldberg et al. |
| 8,672,922 B2 | 3/2014 | Loh et al. |
| 8,682,489 B2 | 3/2014 | Itkowitz et al. |
| 8,706,184 B2 | 4/2014 | Mohr et al. |
| 8,715,167 B2 | 5/2014 | Stern et al. |
| 8,747,288 B2 | 6/2014 | Strotzer et al. |
| 8,749,189 B2 | 6/2014 | Nowlin et al. |
| 8,749,190 B2 | 6/2014 | Nowlin et al. |
| 8,761,337 B2 | 6/2014 | Naylor et al. |
| 8,786,241 B2 | 7/2014 | Nowlin et al. |
| 8,806,359 B2 | 8/2014 | Garibaldi et al. |
| 8,816,628 B2 | 8/2014 | Nowlin et al. |
| 8,823,308 B2 | 9/2014 | Nowlin et al. |
| 8,828,023 B2 | 9/2014 | Neff et al. |
| 8,831,782 B2 | 9/2014 | Itkowitz |
| 8,870,861 B2 | 10/2014 | El-Galley et al. |
| 8,888,764 B2 | 11/2014 | Devengenzo et al. |
| 8,930,027 B2 | 1/2015 | Schaible et al. |
| 8,939,500 B2 | 1/2015 | Voigt et al. |
| 8,968,333 B2 | 3/2015 | Yu et al. |
| 8,989,903 B2 | 3/2015 | Weir et al. |
| 8,996,173 B2 | 3/2015 | Itkowitz et al. |

(56) References Cited

U.S. PATENT DOCUMENTS

| | | |
|---|---|---|
| 9,002,517 B2 | 4/2015 | Bosscher et al. |
| 9,026,247 B2 | 5/2015 | White et al. |
| 9,078,686 B2 | 7/2015 | Schena |
| 9,108,318 B2 | 8/2015 | Diolaiti |
| 9,126,614 B2 | 9/2015 | Lorenzo et al. |
| 9,129,422 B2 | 9/2015 | Mountney et al. |
| 9,179,980 B2 | 11/2015 | Yoon |
| 9,198,731 B2 | 12/2015 | Balaji et al. |
| 9,215,293 B2 | 12/2015 | Miller |
| 9,221,172 B2 | 12/2015 | Williamson et al. |
| 9,232,984 B2 | 1/2016 | Guthart et al. |
| 9,241,768 B2 | 1/2016 | Sandhu et al. |
| 9,254,572 B2 | 2/2016 | Strotzer |
| 9,256,936 B2 | 2/2016 | Jacobs et al. |
| 9,259,276 B2 | 2/2016 | Mintz et al. |
| 9,259,282 B2 | 2/2016 | Azizian et al. |
| 9,295,524 B2 | 3/2016 | Schena et al. |
| 9,320,568 B2 | 4/2016 | Orban et al. |
| 9,333,042 B2 | 5/2016 | Diolaiti et al. |
| 9,345,546 B2 | 5/2016 | Toth et al. |
| 9,433,288 B2 | 9/2016 | Voigt et al. |
| 9,486,159 B2 | 11/2016 | Coste-Maniere et al. |
| 9,694,839 B2 | 7/2017 | Canady et al. |
| 10,034,721 B1* | 7/2018 | Timm .................. B62B 5/0006 |
| 10,333,296 B1 | 6/2019 | Wu et al. |
| 10,485,623 B2 | 11/2019 | Wiggers |
| 10,792,119 B2* | 10/2020 | Timm .................. A61B 90/50 |
| 10,856,948 B2* | 12/2020 | Cagle .................. A61B 50/13 |
| 10,913,145 B2* | 2/2021 | Cagle .................. B62B 3/005 |
| 10,913,291 B2 | 2/2021 | Nishiura |
| 11,622,830 B2* | 4/2023 | Timm .................. A61B 50/13 |
| | | 248/645 |
| 2002/0133174 A1 | 9/2002 | Charles et al. |
| 2004/0236175 A1 | 11/2004 | Boone et al. |
| 2005/0206107 A1 | 9/2005 | Schubert et al. |
| 2006/0161136 A1 | 7/2006 | Anderson et al. |
| 2009/0068620 A1 | 3/2009 | Knobel et al. |
| 2009/0240370 A1 | 9/2009 | Nichols et al. |
| 2009/0248041 A1 | 10/2009 | Williams et al. |
| 2010/0012798 A1 | 1/2010 | Blum et al. |
| 2010/0243344 A1 | 9/2010 | Wyrobek et al. |
| 2010/0286712 A1 | 11/2010 | Won et al. |
| 2012/0154564 A1 | 6/2012 | Hoffman et al. |
| 2013/0085389 A1 | 4/2013 | Tsang et al. |
| 2013/0085510 A1 | 4/2013 | Stefanchik et al. |
| 2014/0052154 A1 | 2/2014 | Griffiths et al. |
| 2014/0100588 A1 | 4/2014 | Blumenkranz et al. |
| 2014/0107627 A1 | 4/2014 | Blumenkranz et al. |
| 2014/0130810 A1 | 5/2014 | Azizian et al. |
| 2014/0168073 A1 | 6/2014 | Chizeck et al. |
| 2014/0171965 A1 | 6/2014 | Loh et al. |
| 2014/0188131 A1 | 7/2014 | Toth et al. |
| 2014/0276949 A1 | 9/2014 | Staunton et al. |
| 2014/0282196 A1 | 9/2014 | Zhao et al. |
| 2014/0297130 A1 | 10/2014 | Griffiths et al. |
| 2015/0032126 A1 | 1/2015 | Nowlin et al. |
| 2015/0045812 A1 | 2/2015 | Seo |
| 2015/0051733 A1 | 2/2015 | Nowlin et al. |
| 2015/0190201 A1 | 7/2015 | Olson |
| 2015/0223897 A1 | 8/2015 | Kostrzewski et al. |
| 2015/0265356 A1 | 9/2015 | Schena |
| 2015/0321355 A1 | 11/2015 | Kishi |
| 2015/0374446 A1 | 12/2015 | Malackowski et al. |
| 2016/0076992 A1 | 3/2016 | Gillespie et al. |
| 2016/0140875 A1 | 5/2016 | Kumar et al. |
| 2016/0157943 A1 | 6/2016 | Mintz et al. |
| 2016/0166345 A1 | 6/2016 | Kumar et al. |
| 2016/0184037 A1 | 6/2016 | Cooper et al. |
| 2016/0242860 A1 | 8/2016 | Diolaiti et al. |
| 2017/0000575 A1 | 1/2017 | Griffiths et al. |
| 2017/0065354 A1 | 3/2017 | Shiels et al. |
| 2017/0065355 A1 | 3/2017 | Ross et al. |
| 2017/0071692 A1 | 3/2017 | Taylor et al. |
| 2017/0071693 A1 | 3/2017 | Taylor et al. |
| 2017/0079730 A1 | 3/2017 | Azizian et al. |
| 2017/0083453 A1 | 3/2017 | Guilford et al. |
| 2017/0087730 A1 | 3/2017 | Robinson et al. |
| 2017/0119421 A1 | 5/2017 | Staunton et al. |
| 2017/0135771 A1 | 5/2017 | Auld et al. |
| 2017/0245927 A1 | 8/2017 | Govari et al. |
| 2017/0312047 A1 | 11/2017 | Swarup et al. |
| 2018/0042682 A1 | 2/2018 | Iceman et al. |
| 2018/0051850 A1 | 2/2018 | Bax et al. |
| 2018/0078439 A1 | 3/2018 | Cagle et al. |
| 2018/0078440 A1 | 3/2018 | Koenig et al. |
| 2018/0147104 A1 | 5/2018 | Timm et al. |
| 2018/0147105 A1 | 5/2018 | Timm et al. |
| 2018/0147106 A1 | 5/2018 | Soundararajan et al. |
| 2018/0207794 A1 | 7/2018 | Sebring et al. |
| 2018/0271604 A1 | 9/2018 | Grout et al. |
| 2018/0333215 A1 | 11/2018 | Timm et al. |
| 2018/0344421 A1 | 12/2018 | Cagle et al. |
| 2018/0361568 A1 | 12/2018 | Cagle et al. |
| 2018/0362060 A1 | 12/2018 | Schaller et al. |
| 2020/0000536 A1 | 1/2020 | Yakimovich et al. |

FOREIGN PATENT DOCUMENTS

| | | |
|---|---|---|
| CN | 102006834 A | 4/2011 |
| CN | 103448643 A | 12/2013 |
| CN | 105163998 A | 12/2015 |
| CN | 105213030 A | 1/2016 |
| CN | 105310775 A | 2/2016 |
| CN | 205073024 U | 3/2016 |
| CN | 107128341 A | 9/2017 |
| CN | 110868954 A | 3/2020 |
| CN | 110868956 A | 3/2020 |
| CN | 110913820 A | 3/2020 |
| EP | 0752237 A1 | 1/1997 |
| EP | 2145586 A1 | 1/2010 |
| EP | 2145596 A1 | 1/2010 |
| EP | 2893898 A1 | 7/2015 |
| EP | 2898898 A1 | 7/2015 |
| EP | 3600122 A1 | 2/2020 |
| JP | 61-173822 A | 8/1986 |
| JP | 02-059468 A | 2/1990 |
| JP | 04-019729 A | 1/1992 |
| JP | 06-297378 A | 10/1994 |
| JP | 08-224243 A | 9/1996 |
| JP | 2000-255428 A | 9/2000 |
| JP | 2007-276063 A | 10/2007 |
| JP | 2014-158942 A | 9/2014 |
| JP | 2017-513550 A | 6/2017 |
| KR | 10-2010-0067846 A | 6/2010 |
| KR | 10-2016-0135240 A | 11/2016 |
| RU | 122281 U1 | 11/2012 |
| WO | 2008/103209 A1 | 8/2008 |
| WO | 2010/068005 A2 | 6/2010 |
| WO | 2014/151621 A1 | 9/2014 |
| WO | 2014/152694 A1 | 9/2014 |
| WO | 2014/201538 A1 | 12/2014 |
| WO | 2015/142798 A1 | 9/2015 |
| WO | 2015/142801 A1 | 9/2015 |
| WO | 2015/175203 A1 | 11/2015 |
| WO | 2016/048738 A1 | 3/2016 |
| WO | 2016/054256 A1 | 4/2016 |
| WO | 2016/058079 A1 | 4/2016 |
| WO | 2016/069661 A1 | 5/2016 |
| WO | 2017/030848 A1 | 2/2017 |
| WO | 2017/062391 A1 | 4/2017 |
| WO | 2017/083453 A1 | 5/2017 |
| WO | 2017/083459 A1 | 5/2017 |
| WO | WO-2017083453 A1 * | 5/2017 ............. A61B 34/30 |
| WO | 2018/053282 A1 | 3/2018 |
| WO | 2018/217518 A1 | 11/2018 |
| WO | 2018/222470 A1 | 12/2018 |
| WO | 2018/236594 A1 | 12/2018 |

OTHER PUBLICATIONS

Notice of Reason for Refusal for Japanese Application No. 2019-563192; Oct. 27, 2020; 7 pp.

(56) References Cited

OTHER PUBLICATIONS

Notice of Reason for Refusal for Japanese Application No. 2019-563290; Dec. 1, 2020; 8 pp.
Notice of Reasons for Refusal of the Japanese Patent Office dated Jun. 22, 2021 for related Japanese Patent Application No. 2019-563290.
Notice of Reasons for Rejection for Japanese Application No. 2019-563141 mailed Oct. 27, 2020, 6 pages.
Notice of Reasons for Rejection for Japanese Application No. 2019-563190 mailed Oct. 27, 2020, 6 pages.
Notice of Reasons for Rejection for Japanese Application No. 2019-563192 mailed Nov. 4, 2020, 7 pages.
Notice of Reasons for Rejection for Japanese Application No. 2019-563290 mailed Dec. 8, 2020, 7 pages.
Notification of Reason for Refusal of the Korean Patent Office dated Oct. 21, 2021 for related Korean Patent Application No. 10-2019-7034549.
Notification to Grant Patent Right for Invention of the Chinese Patent Office dated Sep. 3, 2021 for related Chinese Patent Application No. 201880040951.8.
Office Action and Search Report for Chinese Application No. 2018800409518 mailed Apr. 8, 2021, 13 pages.
Office Action for Japanese Patent Application No. 2021-176398, dated Oct. 11, 2022, 10 pages (including translation).
Office Action for Korean Application No. 10-2019-7033930 mailed Jun. 9, 2021, 13 pages including translation.
Office Action of the BR Patent Office dated Jul. 21, 2022 for related BR Patent Application No. 112019021760-6.
Office Action of the BR Patent Office dated Sep. 7, 2022 for related BR Patent Application No. 112019022313-4.
Office Action of the BR Patent Office dated Sep. 12, 2022 for related BR Patent Application No. 112019022051-8.
Requirement for Restriction/Election of the U.S. Patent Office dated Aug. 3, 2018 for related U.S. Appl. No. 15/725,093.
Requirement for Restriction/Election of the U.S. Patent Office dated Jan. 2, 2020 for related U.S. Appl. No. 15/785,291.
Requirement for Restriction/Election of the U.S. Patent Office dated Jun. 17, 2019 for related U.S. Appl. No. 15/785,341.
Search Report of the Chinese Patent Office dated Aug. 26, 2021 for related Chinese Patent Application No. 201880040951.8.
Search Report of the Chinese Patent Office dated Mar. 31, 2021 for related Chinese Patent Application No. 201880040951.8.
U.S. Patent Application filed on Nov. 27, 2017, by Soundararajan et al., U.S. Appl. No. 15/823,042.
U.S. Patent Application filed on Nov. 27, 2017, by Timm et al., U.S. Appl. No. 15/822,986.
U.S. Patent Application filed on Nov. 27, 2017, by Timm et al., U.S. Appl. No. 15/823,006.
U.S. Patent Application filed on Oct. 16, 2016, by Timm et al., U.S. Appl. No. 15/785,341.
U.S. Patent Application filed on Oct. 16, 2017, by Cagle et al., U.S. Appl. No. 15/785,291.
U.S. Patent Application filed on Oct. 19, 2017, by Schaller et al., U.S. Appl. No. 15/788,730.
U.S. Patent Application filed on Oct. 4, 2017, by Wiggers, U.S. Appl. No. 15/725,093.
U.S. Patent Application filed on Sep. 15, 2017, by Cagle et al., U.S. Appl. No. 15/706,087.
U.S. Patent Application filed on Sep. 15, 2017, by Koenig, U.S. Appl. No. 15/706,112.
U.S. Patent Application filed on Sep. 27, 2017, by Timm et al., U.S. Appl. No. 15/717,599.
U.S. Patent Application No. filed on Oct. 16, 2017, by Cagle et al., U.S. Appl. No. 15/785,331.
Written Decision on Registration of the Korean Patent Office dated Mar. 21, 2022 for related Korean Patent Application No. 10-2019-7034549.
Australian Examination Report for Australian Application No. 2018276946 mailed Jan. 24, 2020, 4 pages.
Australian Examination Report for Australian Application No. 2018341716 mailed Oct. 12, 2020, 3 pp.
Decision of Refusal of the Japanese Patent Office dated Mar. 30, 2021 for related Japanese Patent Application No. 2019-563192.
Decision of Refusal of the Japanese Patent Office dated May 11, 2021 for related Japanese Patent Application No. 2019-563141.
Decision to Grant a Patent of the Japanese Patent Office dated Aug. 24, 2021 for related Japanese Patent Application No. 2019-563192.
Decision to Grant a Patent of the Japanese Patent Office dated Nov. 16, 2021 for related Japanese Patent Application No. 2019-563190.
Decision to Grant a Patent of the Japanese Patent Office dated Nov. 19, 2021 for related Japanese Patent Application No. 2019-563290.
Examination Report for Australian Application No. 2018278218 mailed Jul. 13, 2020, 4 pages.
Examination Report for Australian Application No. 2018289123 mailed May 11, 2020, 4 pages.
Examination Report for Australian Application No. 2020260428 mailed Jul. 23, 2021, 8 pages.
Examination Report No. 1 of the Australian Patent Office dated Jan. 31, 2020 for related Australian Patent Application No. 2018271773.
Examiner Decision of Refusal for Japanese Application No. 2019-563141 mailed Jun. 29, 2021, 6 pages.
Examiner Decision of Refusal for Japanese Application No. 2019-563190 mailed Jun. 22, 2021, 6 pages including ranslalion.
Examiner Decision of Refusal for Japanese Application No. 2019-563192 mailed Apr. 6, 2021, 4 pages.
Examiner Decision of Refusal for Japanese Application No. 2019-563290 mailed Jun. 29, 2021, 8 pages.
Examiner's Decision of Refusal for Japanese Application No. 2019-563192 mailed Mar. 30, 2021, 5 pages.
Examiner's Report for Canadian Application No. 3,060,997 mailed Mar. 10, 2021, 3 pages.
Examiner's Report for Canadian Application No. 3,074,438 mailed Apr. 19, 2021, 5 pages.
Examiner's Report for Canadian Application No. 3,060,359 mailed Dec. 17, 2020, 3 pages.
Examiner's Report for Canadian Application No. 3,060,879 mailed Dec. 17, 2020, 4 pages.
Examiner's Report for Canadian Application No. 3,060,993 mailed Dec. 18, 2020, 4 pages.
Examiner's Report for Canadian Application No. 3,060,359 mailed Aug. 17, 2021, 4 pages.
Examiner's Decision of Refusal of the Japanese Patent Office dated Jun. 22, 2021 for related Japanese Patent Application No. 2019-563190.
Extended European Search Report [Communication pursuant to Rules 70(2) and 70a (2) EPC] of the European Patent Office dated Dec. 8, 2020 for related Korean Patent Application No. 18806664.1.
Extended European Search Report for European Application No. 18862162.7 mailed Mar. 18, 2021, 22 pages.
Extended European Search Report for European Application No. 18806664.1 mailed Nov. 19, 2020, 7 pages.
Extended European Search Report for European Application No. 18808974.2 mailed Nov. 23, 2020, 9 pages.
Extended European Search Report for European Application No. 18810600.9 mailed Dec. 11, 2020, 7 pages.
Extended European Search Report for European Application No. 18820247.7 mailed Dec. 14, 2020, 7 pages.
Final Office Action of the U.S. Patent Office dated Aug. 1, 2022 for related U.S. Appl. No. 17/021,860.
Final Office Action of the U.S. Patent Office dated Jan. 7, 2020 for related U.S. Appl. No. 15/785,341.
Final Office Action of the U.S. Patent Office dated Sep. 6, 2019 for related U.S. Appl. No. 15/785,331.
First Office Action and Search Report of the China National Intellectual Property Administration dated Jun. 1, 2022 for related Chinese Patent Application No. 201880033717.2.
First Office Action and Search Report of the China National Intellectual Property Administration dated Jun. 1, 2022 for related Chinese Patent Application No. 201880035692.X.
First Office Action for Chinese Patent Application No. 201880063157.5, dated Nov. 28, 2022.

(56) References Cited

OTHER PUBLICATIONS

First Office Action of the Chinese Patent Office dated Jun. 20, 2022 for related Chinese Patent Application No. 201880035704.9.
First Office Action of the Chinese Patent Office dated Apr. 8, 2021 for related Chinese Patent Application No. 201880040951.8.
Grant of Patent of the Korean Patent Office dated Aug. 23, 2021 for related Korean Patent Application No. 10-2019-7034862.
Grant of Patent of the Korean Patent Office dated Dec. 20, 2021 for related Korean Patent Application No. 10-2019-7033930.
Grant of Patent of the Korean Patent Office dated Oct. 26, 2021 for related Korean Patent Application No. 10-2019-7037287.
Intention to grant received for European Patent Application No. 18820247.7, mailed on Feb. 6, 2023, 6 pages.
International Preliminary Report on Patentability for International Application No. PCT/US2018/033056, mailed Dec. 5, 2019, 6 pages.
International Preliminary Report on Patentability for International Application No. PCT/US2018/034229, mailed Dec. 12, 2019, 6 pages.
International Preliminary Report on Patentability for International Application No. PCT/US2018/034945, mailed Dec. 12, 2019, 6 pages.
International Preliminary Report on Patentability for International Application No. PCT/US2018/036566, mailed Jan. 2, 2020, 6 pages.
International Search Report and Written Opinion of the PCT Patent Office dated Aug. 9, 2018 for related PCT Patent Application No. PCT/US2018/033056.
International Search Report and Written Opinion of the Searching Authority, dated Aug. 23, 2018, for PCT application No. PCT/US2018/034229.
International Search Report and Written Opinion of the Searching Authority, dated Sep. 13, 2018, for PCT Application No. PCT/US2018/034945.
International Search Report and Written Opinion of the Searching Authority, dated Sep. 27, 2018, for PCT application No. PCT/US2018036566.
Non-Final Office Action of the U.S. Patent Office dated Apr. 25, 2022 for related U.S. Appl. No. 17/067,527.
Non-Final Office Action of the U.S. Patent Office dated Dec. 24, 2021 for related U.S. Appl. No. 17/021,860.
Non-Final Office Action of the U.S. Patent Office dated Jan. 3, 2020 for related U.S. Appl. No. 15/785,331.
Non-Final Office Action of the U.S. Patent Office dated Mar. 23, 2021 for related U.S. Appl. No. 16/653,565.
Non-Final Office Action of the U.S. Patent Office dated Mar. 31, 2020 for related U.S. Appl. No. 15/785,291.
Non-Final Office Action of the U.S. Patent Office dated May 20, 2022 for related U.S. Appl. No. 17/070,822.
Non-Final Office Action of the U.S. Patent Office dated May 28, 2019 for related U.S. Appl. No. 15/785,331.
Non-Final Office Action of the U.S. Patent Office dated Nov. 5, 2018 for related U.S. Appl. No. 15/725,093.
Non-Final Office Action of the U.S. Patent Office dated Sep. 6, 2019 for related U.S. Appl. No. 15/785,341.
Notice of Acceptance of the Australian Patent Office dated Aug. 3, 2020 for related Australian Patent Application No. 2018271773.
Notice of Acceptance of the Australian Patent Office dated Jul. 28, 2020 for related Australian Patent Application No. 2018289123.
Notice of Acceptance of the Australian Patent Office dated Nov. 10, 2020 for related Australian Patent Application No. 2018278218.
Notice of Allowability of the U.S. Patent Office dated Dec. 18, 2020 for related U.S. Appl. No. 15/785,291.
Notice of Allowance of the U.S. Patent Office dated Oct. 24, 2022 for related U.S. Appl. No. 17/070,822.
Notice of Allowance Action of the U.S. Patent Office dated Dec. 21, 2022 for related U.S. Appl. No. 17/070,822.
Notice of Allowance for U.S. Appl. No. 15/785,331; filed on Oct. 16, 2017; 5 pp (Sep. 28, 2020).
Notice of Allowance for Canadian Application No. 3,060,993, mailed Oct. 14, 2021, 1 page.
Notice of Allowance for U.S. Appl. No. 17/070,822 mailed Oct. 12, 2022, 18 pages.
Notice of Allowance of the U.S. Patent Office dated Jan. 11, 2021 for related U.S. Appl. No. 15/785,291.
Notice of Allowance of the U.S. Patent Office dated Apr. 4, 2018 for related U.S. Appl. No. 15/717,599.
Notice of Allowance of the U.S. Patent Office dated Aug. 9, 2021 for related U.S. Appl. No. 16/653,565.
Notice of Allowance of the U.S. Patent Office dated Dec. 27, 2022 for related U.S. Appl. No. 17/067,527.
Notice of Allowance of the U.S. Patent Office dated Dec. 9, 2022 for related U.S. Appl. No. 17/021,860.
Notice of Allowance of the U.S. Patent Office dated Jan. 11, 2023 for related U.S. Appl. No. 17/021,860.
Notice of Allowance of the U.S. Patent Office dated Jan. 20, 2023 for related U.S. Appl. No. 17/070,822.
Notice of Allowance of the U.S. Patent Office dated Jul. 15, 2020 for related U.S. Appl. No. 15/785,331.
Notice of Allowance of the U.S. Patent Office dated Jul. 17, 2019 for related U.S. Appl. No. 15/725,093.
Notice of Allowance of the U.S. Patent Office dated Jul. 23, 2021 for related U.S. Appl. No. 16/653,565.
Notice of Allowance of the U.S. Patent Office dated Mar. 18, 2019 for related U.S. Appl. No. 15/725,093.
Notice of Allowance of the U.S. Patent Office dated May 26, 2020 for related U.S. Appl. No. 15/785,341.
Notice of Allowance of the U.S. Patent Office dated Nov. 12, 2020 for related U.S. Appl. No. 15/785,291.
Notice of Allowance of the U.S. Patent Office dated Nov. 7, 2022 for related U.S. Appl. No. 17/067,527.
Notice of Allowance of the U.S. Patent Office dated Oct. 12, 2022 from related U.S. Appl. No. 17/070,822, 18 pages.
Notice of Allowance of the U.S. Patent Office dated Oct. 12, 2021 for related U.S. Appl. No. 16/653,565.
Notice of Allowance of the U.S. Patent Office dated Oct. 12, 2022 for related U.S. Appl. No. 17/070,822.
Notice of Allowance of the U.S. Patent Office dated Oct. 14, 2022 for related U.S. Appl. No. 17/067,527.
Notice of Allowance of the U.S. Patent Office dated Oct. 30, 2020 for related U.S. Appl. No. 15/785,291.
Notice of Allowance of the U.S. Patent Office dated Oct. 31, 2022 for related U.S. Appl. No. 17/067,527.
Notice of Allowance of the U.S. Patent Office dated Oct. 5, 2022 for related U.S. Appl. No. 17/067,527.
Notice of Allowance of the U.S. Patent Office dated Sep. 10, 2021 for related U.S. Appl. No. 16/653,565.
Notice of Allowance of the U.S. Patent Office dated Sep. 25, 2020 for related U.S. Appl. No. 15/785,291.
Notice of Allowance of the U.S. Patent Office dated Sep. 28, 2020 for related U.S. Appl. No. 15/785,331.
Notice of Allowance of the U.S. Patent Office dated Sep. 28, 2022 for related U.S. Appl. No. 17/067,527.
Notice of Allowance of the U.S. Patent Office dated Sep. 9, 2020 for related U.S. Appl. No. 15/785,341.
Notice of Final Office Action of the Korean Patent Office dated May 27, 2021 for related Korean Patent Application No. 10-2019-7037287.
Notice of Office Action of the Korean Patent Office dated Apr. 22, 2021 for related Korean Patent Application No. 10-2019-7034549.
Notice of Office Action of the Korean Patent Office dated Feb. 22, 2021 for related Korean Patent Application No. 10-2019-7034862.
Notice of Preliminary Rejection from related Korean Patent Application No. 10-2020-7007352 mailed on Dec. 20, 2021, 6 pages.
Notice of Preliminary Rejection of the Korean Patent Office dated Jun. 8, 2021 for related Korean Patent Application No. 10-2020-7007352.
Notice of Reason for Refusal for Japanese Application No. 2019-563141; Oct. 22, 2020; 7 pp.

* cited by examiner

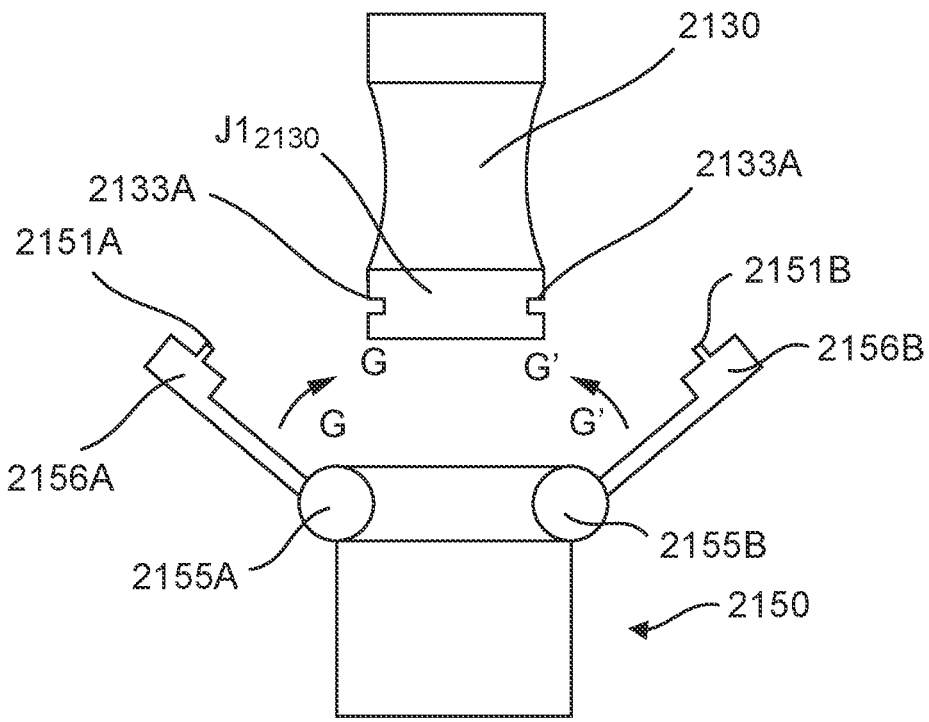
FIG. 15A
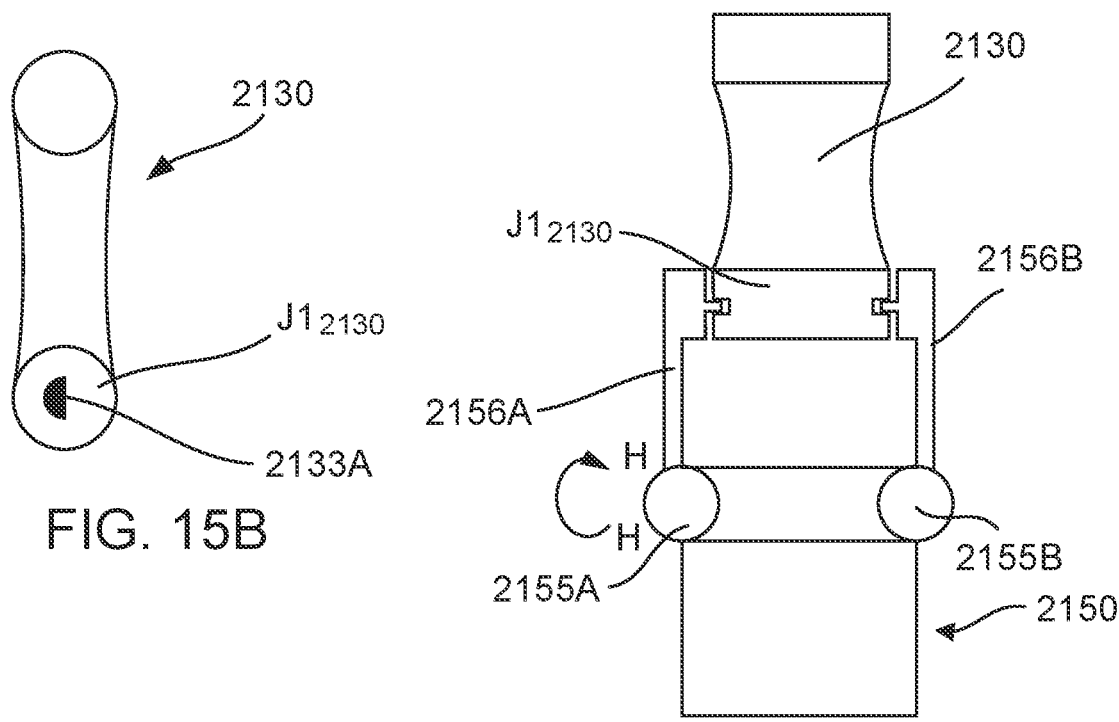
FIG. 15B
FIG. 15C

ROBOTIC ARM CART AND USES THEREFOR

CROSS-REFERENCE TO RELATED APPLICATIONS

This application is a continuation of U.S. application Ser. No. 17/021,860, filed Sep. 15, 2020, entitled "Robotic Arm Cart And Uses Therefor," which in turn is a continuation of and claims priority to U.S. application Ser. No. 15/785,341, filed Oct. 16, 2017, now U.S. Pat. No. 10,792,119, issued Oct. 6, 2020, which in turn claims priority to U.S. Provisional Application No. 62/509,611, filed May 22, 2017, and the entire content of the priority applications is hereby incorporated by reference.

BACKGROUND

Embodiments described herein relate to apparatus and methods for a robotic arm cart for transporting, delivering, and securing robotic arms to, for example, a surgical table.

SUMMARY

Apparatus and methods for providing a robotic arm cart for transporting, delivering, and securing robotic arms to a surgical table having a table top on which a patient can be disposed are described herein. In some embodiments, an apparatus includes an arm cart including an arm container and a base. The arm container can be configured to receive and contain one or more robotic arms. The arm cart can include a first coupling member configured to engage with a second coupling member associated with a surgical table such that, when the first coupling member is engaged with the second coupling member, the one or more robotic arms can be releasably coupled with the surgical table. The arm cart can provide for movement of the one or more robotic arms in at least one of a lateral, longitudinal, or vertical direction relative to the table top prior to the securement of the one or more robotic arms to the surgical table.

BRIEF DESCRIPTION OF THE DRAWINGS

FIGS. 15A-15C are various views of an arm cart and a robotic arm in multiple configurations, according to an embodiment.

DETAILED DESCRIPTION

Apparatus and methods for providing a robotic arm cart for transporting, delivering, and securing robotic arms to a surgical table having a table top on which a patient can be disposed are described herein. In some embodiments, an apparatus includes an arm cart including an arm container and a base. The arm container can be configured to receive and contain one or more robotic arms. The arm cart can include a first coupling member configured to engage with a second coupling member associated with a surgical table such that, when the first coupling member is engaged with the second coupling member, the one or more robotic arms can be releasably coupled with the surgical table. The arm cart can provide for movement of the one or more robotic arms in at least one of a lateral, longitudinal, or vertical direction relative to the table top prior to the securement of the one or more robotic arms to the surgical table.

Figure 1A:
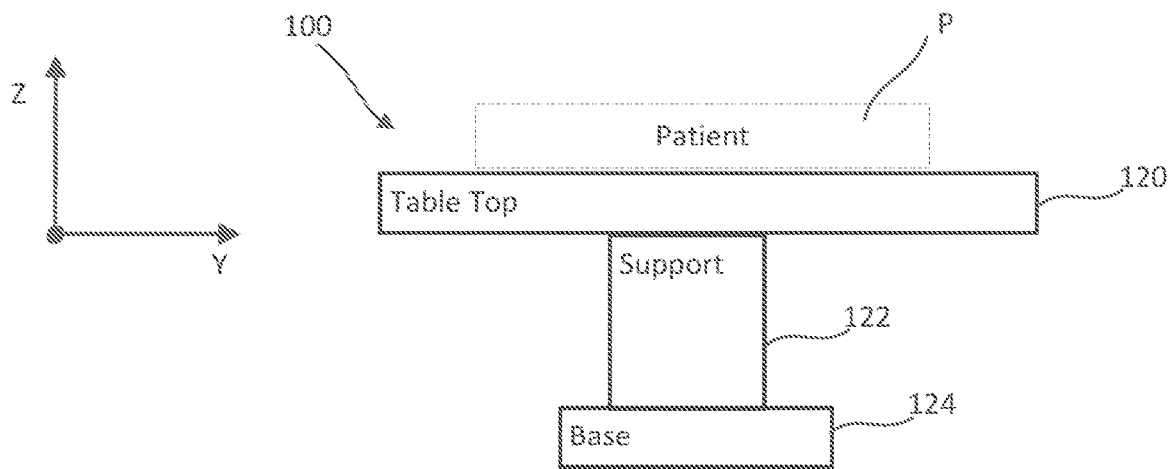
FIGS. 1A and 1B are a schematic side view and a schematic top view, respectively, of a surgical table, according to an embodiment.
Figure 1B:
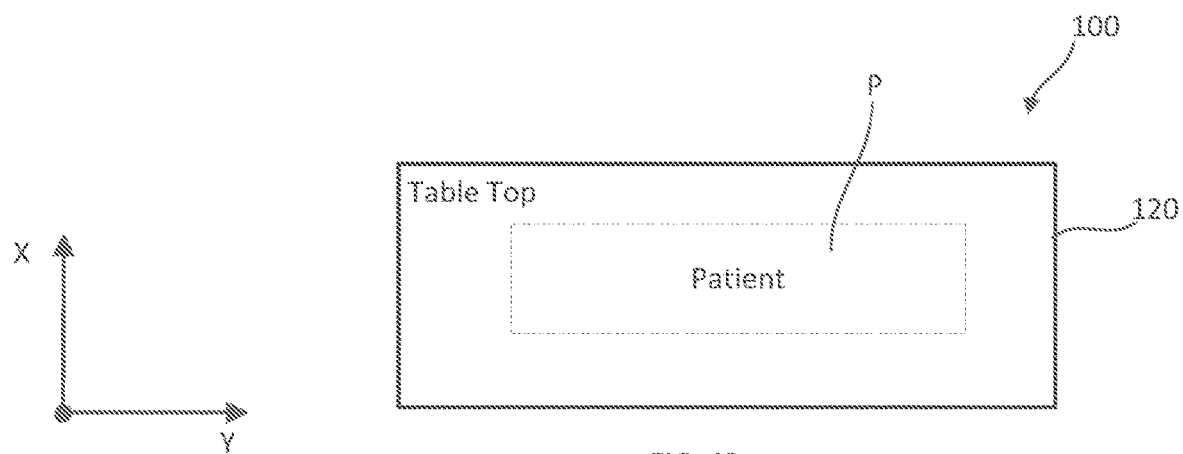

As shown schematically in FIGS. 1A-1B, a surgical table 100 includes a table top 120, a table support 122 and a table base 124. The table top 120 has an upper surface on which a patient P can be disposed during a surgical procedure, as shown schematically in FIG. 1A. The table top 120 is disposed on the support 122, which can be, for example, a pedestal, at a suitable height above the floor. The support 122 (also referred to herein as a pedestal) may provide for movement of the table top 120 in a desired number of degrees of freedom, such as translation in the Z axis (height above the floor), Y axis (along the longitudinal axis of the table), and/or X axis (along the lateral axis of the table), and/or rotation about the Z, Y, and/or X axes. The table top 120 may also include multiple sections that are movable relative to each other along/about any suitable axes, e.g., separate sections for each of the torso, one or both legs, and/or one or both arms, and a head support section. Movement of the table top 120 and/or its constituent sections may be performed manually, driven by motors, controlled remotely, or through any other suitable means. The support 122 for the table top may be mounted to the base 124, which can be fixed to the floor of the operating room, or can be movable relative to the floor, e.g., by use of wheels on the base 124. In some embodiments, the height of the support 122 can be adjusted, which together with, for example, the motion (e.g., axial (longitudinal) or lateral motion) of the table top 120, can allow for the table top 120 to be positioned at a desired surgical site at a certain height above the floor (e.g., to allow surgeon access) and a certain distance from the support 120. This also can allow robotic arms (e.g., arms 130 discussed below) coupled to the table 100 to reach a desired treatment target on a patient P disposed on the table top 120.

In a robotically-assisted surgical procedure, one or more robotic arms 130 (shown schematically in FIGS. 1C and 1D) can be disposed in a desired operative position relative to a patient disposed on the table top 120 of the surgical table 100 (also referred to herein as "table"). The robotic arm(s) can be used to perform a surgical procedure on a patient disposed on the surgical table 100. In particular, the distal end of each robotic arm can be disposed in a desired operative position so that a medical instrument coupled to the distal end of the robotic arm can perform a desired function.

Figure 1C:
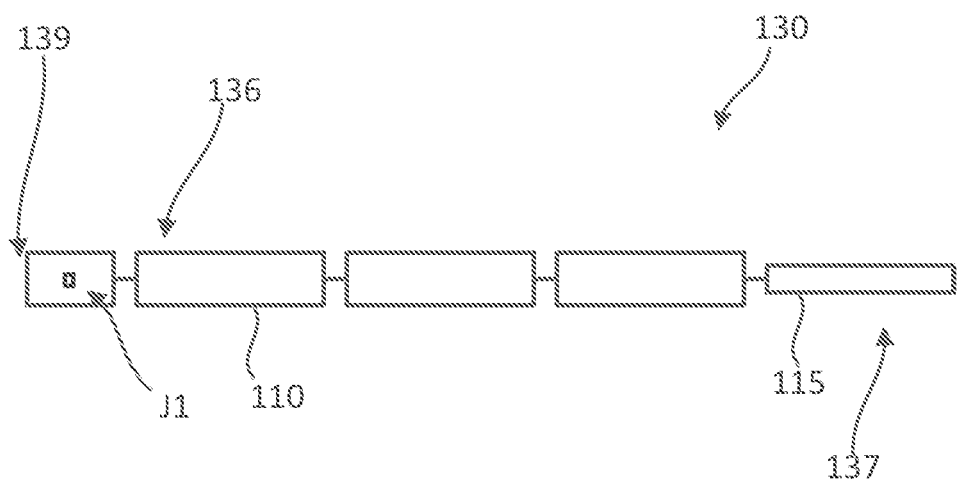
FIG. 1C is a schematic side view of a robotic arm, according to an embodiment, shown in an extended or use configuration.
Figure 1D:
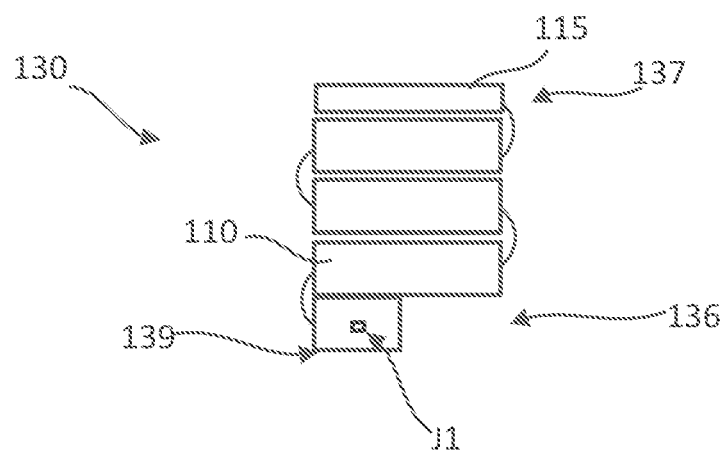
FIG. 1D is a schematic side view of the robotic arm of FIG. 1C, shown in a collapsed or folded configuration.

As shown schematically in FIGS. 1C and 1D, each robotic arm 130 can include a distal end portion 137 and a proximal end portion 136. The distal end portion 137 (also referred to herein as "operating end") can include or have coupled thereto a medical instrument or tool 115. The proximal end portion 136 (also referred to herein as the "mounting end portion" or "mounting end") can include the coupling portion to allow the robotic arm 130 to be coupled to the table 100. The robotic arm 130 can include two or more link members or segments 110 coupled together at joints that can provide for translation along and/or rotation about one or more of the X, Y and/or Z axes (shown, for example, in FIGS. 1A and 1B). The coupling portion of the robotic arm 130 can include a coupling mechanism 139. The coupling mechanism 139 can be disposed at the mounting end 136 of the arm 130 and may be coupled to a segment 110 or incorporated within a segment 110. The robotic arm 130 also includes a target joint J1 disposed at or near the mounting end 136 of the robotic arm 130 that can be included within the coupling mechanism 139 and/or the coupling portion or can be disposed on a link or segment 110 of the robotic arm 130 that is coupled to the coupling portion. The target joint J1 can provide a pivot joint to allow a distal segment of the robotic arm 130 to pivot relative to the table 100. The robotic arm 130 can be moved between various extended configurations for use during a surgical procedure, as shown in FIG. 1C, and various folded or collapsed configurations for storage when not in use, as shown in FIG. 1D.

FIGS. 2A-20C illustrate various embodiments describing apparatus and methods for transporting, delivering, and securing a robotic arm to a surgical table. As described above and in accordance with various embodiments disclosed in more detail below, a robotic arm for use in performing a surgical procedure may be releasably coupled to a surgical table. In some embodiments, robotic arms can be coupled at a fixed location on the table or can be coupled such that the robotic arms can be movable to multiple locations relative to the table top. For example, as shown schematically in FIG. 2A, robotic arms 230 can be coupled to a table top 220 of a surgical table 200. The surgical table 200 can be the same or similar in structure and function to the surgical table 100 described above. For example, the table top 220 has an upper surface on which a patient P can be disposed during a surgical procedure. In some embodiments, the robotic arms 230 can be permanently or releasably coupled, in a fixed or movable location, to an arm adapter that is coupled to or separate from the surgical table. For example, as shown schematically in FIG. 2B, an arm adapter 246 can be coupled to or separate from but engageable with or couplable to the table top 220. The robotic arms 230 can be coupled to the arm adapter 246.

Figure 2A:
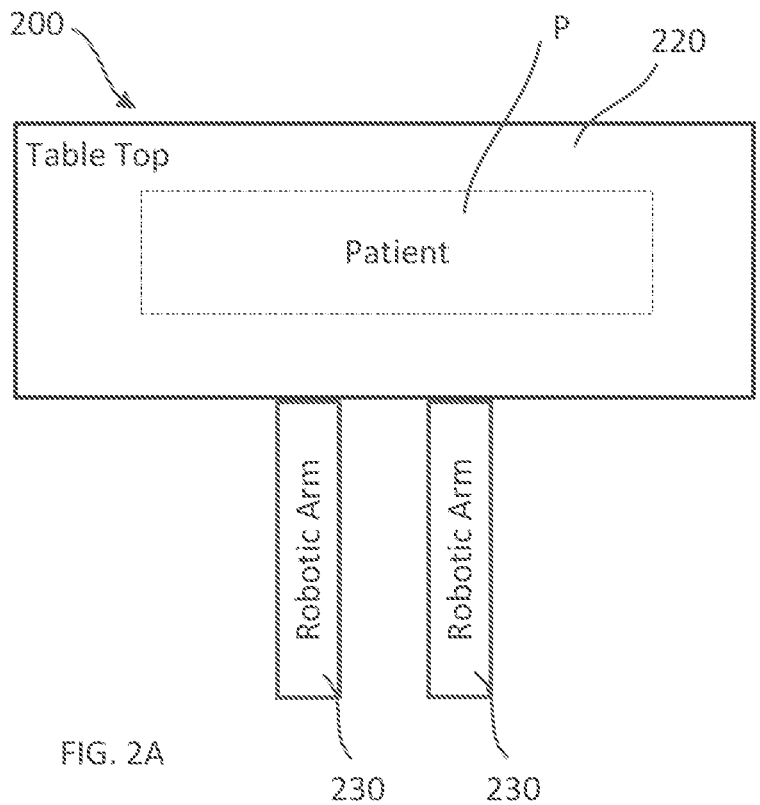
FIG. 2A is a schematic top view of a surgical table with robotic arms coupled thereto, according to an embodiment.
Figure 2B:
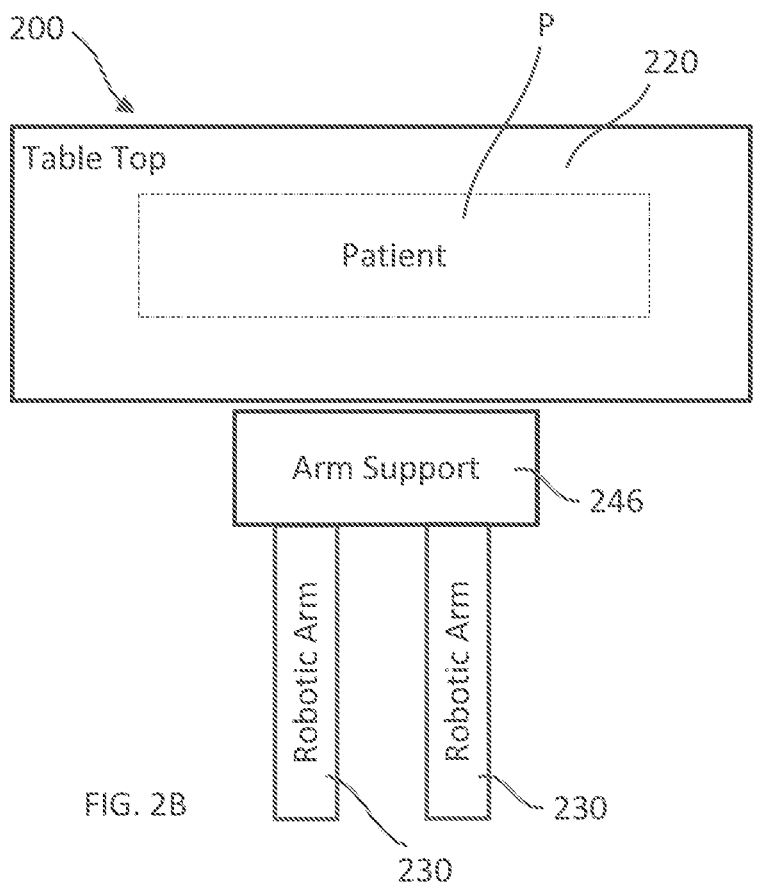
FIG. 2B is a schematic top view of a surgical table with robotic arms and an arm adapter coupled thereto, according to an embodiment.

In preparation for a robotically-assisted surgical procedure in which one or more robotic arms are releasably coupled to the surgical table and/or to an arm adapter, as described with respect to FIGS. 2A and 2B, each robotic arm may be delivered and connected to the surgical table and/or the arm adapter via an arm cart. As shown schematically in FIG. 3, an arm cart 350 can be configured to support one or more robotic arms. The arm cart 350 includes a first robotic arm 330A and can include an optional second robotic arm 330B. Although two robotic arms 330 are shown, the arm cart 350 can be configured to contain, transport, and/or deliver any suitable number of robotic arms 330, such as, for example, one robotic arm, three robotic arms, or four robotic arms.

The arm cart 350 can support the first robotic arm 330A (and the optional second robotic arm 330B) in a variety of configurations. In some embodiments, the arm cart 350 can support the robotic arm 330A such that the center of gravity of the robotic arm 330A is below one or more support structure locations (e.g., cradles) of the arm cart 350 such that the stability of the robotic arm 330A and the arm cart 350 is increased. In some embodiments, the arm cart 350 can support the robotic arm 330A such that the arm cart 350 bears most or all of the weight of the robotic arm 330A and a coupling mechanism (not shown) of the robotic arm 330A can be manually manipulated by a user without the user bearing the most or all of the weight of the robotic arm. For example, the robotic arm 330A can be suspended from a structure of the arm cart 350 or rested on a structure of the arm cart 350. In some embodiments, the arm cart 350 can be configured to secure the robotic arm 330 to the arm cart 350.

The arm cart 330 can be configured for movement such as, for example, by including wheels. The arm cart 350 can be configured to protect the robotic arm 330A from potential impact with the surrounding of the arm cart 350 during, for example, transport or storage. In some embodiments, the arm cart 350 can be configured to move the robotic arm 330 between one or more positions and/or one or more orientations, including, for example, a folded storage or transport position and a deployed or coupling position.

In some embodiments, the arm cart 350 can be configured to couple with one or more additional arm carts such that the two or more arm carts can be moved together to transport a number of robotic arms 330. For example, the arm cart 350 can be a first arm cart and can include a cart coupler (not shown) releasably coupleable to a mating cart coupler on a second, substantially identical cart. The cart coupler can enable the first cart to be moved on a support surface (e.g., a floor) together with the second cart. In some embodiments, the arm cart 350 can couple to and move in unison with two to four other arm carts.

Figure 21A:
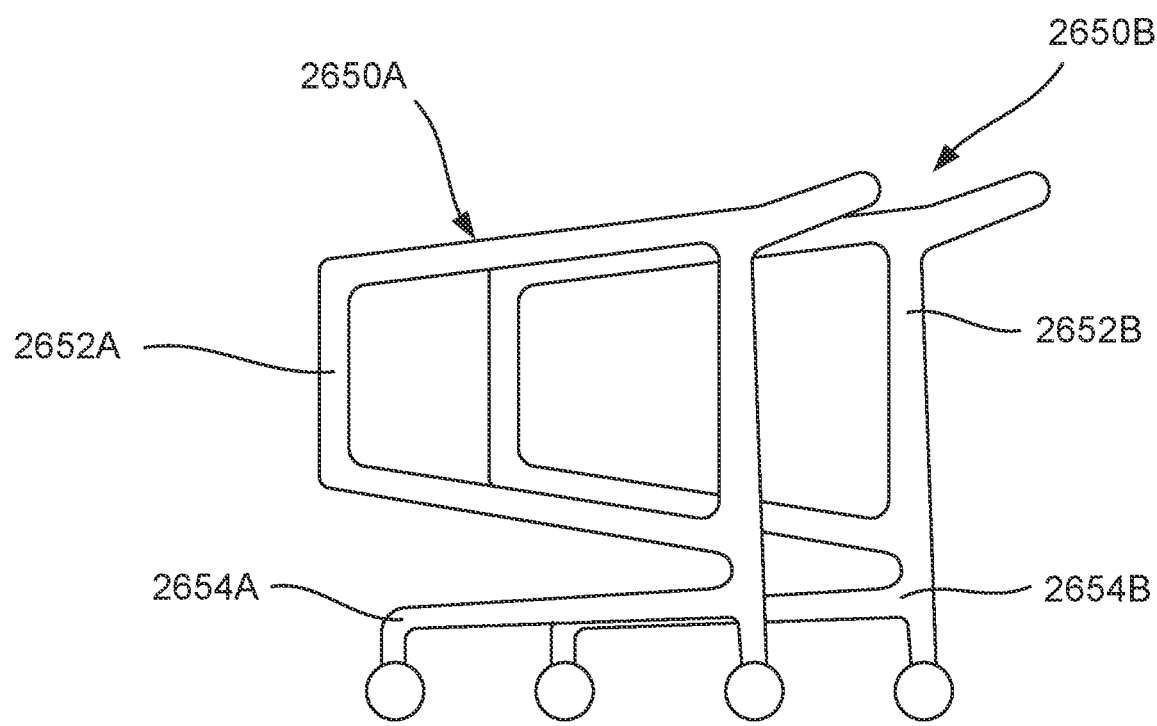
FIG. 21A is a schematic illustration of a side view of two arm carts in a nested configuration, according to an embodiment.

In some embodiments, the arm cart 350 can be shaped and sized such that, when not containing any robotic arms 330, the arm cart 350 can nest with other arm carts for more compact transportation of two or more empty arm carts. Said another way, the arm cart 350 can be a first arm cart and can be configured to nest with a second, substantially identical cart so that the first cart and the second cart collectively occupy less area on a support surface (e.g., a floor) when nested together than when not nested together. For example, FIG. 21A is a schematic illustration of a side view of a first arm cart 2650A and a second arm cart 2650B in a nested configuration. The first arm cart 2650A and the second arm cart 2650B can be the same or similar in structure and/or function to the arm cart 350 described herein. For example, the first arm cart 2650A can include a first arm container 2652A and a first base 2654A, and the second arm cart 2650B can include a second arm container 2652B and a second base 2654B. The arm containers 2652A and 2652B can be the same and/or similar in structure and/or function to the arm container 352 (described below). Similarly, the bases 2654A and 2654B can be the same and/or similar in structure and/or function to the base 354 (described below).

Figure 21B:
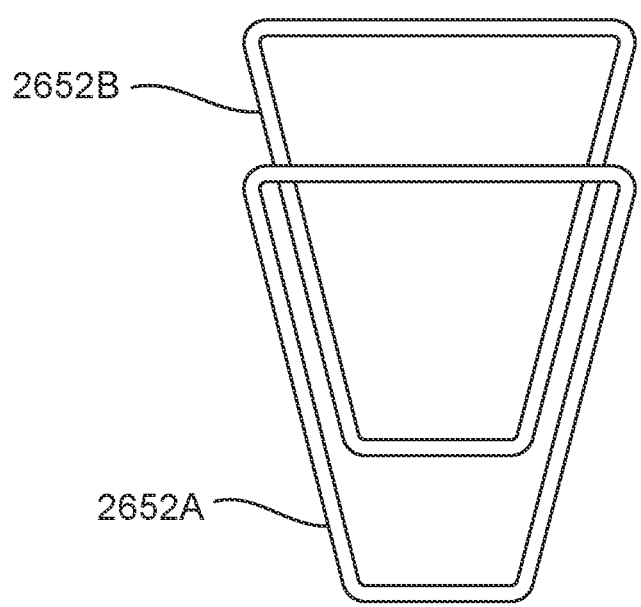
FIG. 21B is a schematic illustration of a top view of two arm containers of the arm carts of FIG. 21A in a nested configuration.

As shown in FIG. 21A, the first arm cart 2650A and the second arm cart 2650B can be shaped and sized such that a portion of the second arm cart 2650B can be inserted into an interior space of the first arm cart 2650A such that the second arm cart 2650B is nested within the first arm cart 2650A, similar to the manner in which conventional shopping carts can be nested together. Said another way, the arm containers 2652A and 2652B can be shaped and sized such that the second arm container 2652B can be partially disposed within the first arm container 2652A and the second base 2654B can be partially disposed within the first base 2654A. As shown in FIG. 21B, which is schematic illustration of a top view of the arm containers 2652A and 2652B, the arm containers 2652A and 2652B can have an isosceles trapezoidal outer profile such that a narrower portion of the second arm container 2652B can fit within the first arm container 2652A. Thus, when engaged as shown in FIG. 21A, the first arm cart 2650A and the second arm cart 2650B can be moved (e.g., pushed) in unison from one location to another. When desired, the first arm cart 2650A can be separated from the second arm cart 2650B and each arm cart 2650A and 2650B can be moved independently. While the first arm cart 2650A is shown and described as receiving the second arm cart 2650B, the second arm cart 2650B can be shaped and sized such that the second arm cart 2650B can also receive the first arm cart 2650A. For example, the first arm cart 2650A and the second arm cart 2650B can be shaped and sized such that the second arm cart 2650B can be nested within the first arm cart 2650A. The first arm cart 2650A can then be disengaged from the second arm cart 2650B, and the second arm cart 2650B can receive the first arm cart 2650A within the second arm cart 2650B similarly to how the first arm cart 2650A received the second arm cart 2650B. Although only two arm carts are shown, any suitable number of arm carts shaped similarly to the first arm cart 2650A and the second arm cart 2650B can be nested in series with the first arm cart 2650A or the second arm cart 2650.

Figure 22:
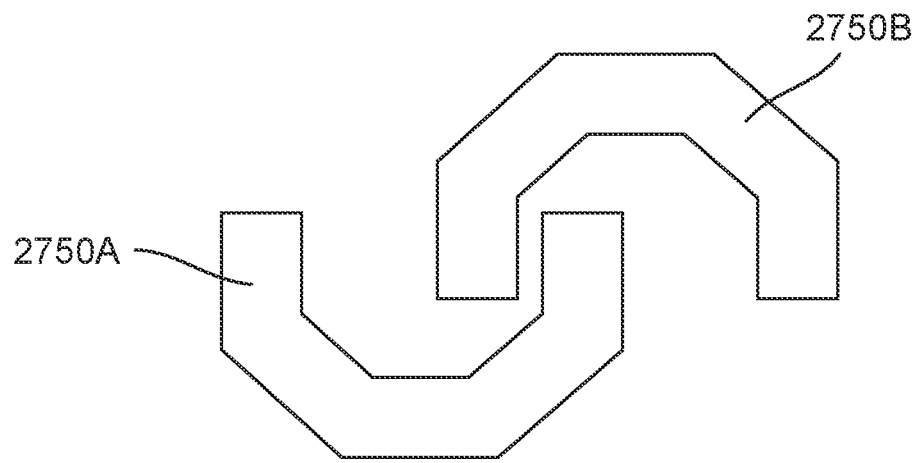
FIG. 22 is a schematic illustration of a top view of two arm carts in a nested configuration, according to an embodiment.

In some embodiments, rather than being shaped as an isosceles trapezoid, an arm cart can have any suitable shape such that the arm cart is configured to nest with another complementary or corresponding arm cart. For example, FIG. 22 is a schematic illustration of a top view of a first arm cart 2750A and a second arm cart 2750B in a nested configuration. The first arm cart 2750A and/or the second arm cart 2750B can be the same and/or similar in structure and/or function to the arm cart 350 described above. The first arm cart 2750A and the second arm cart 2750B are each substantially U-shaped such that the first arm cart 2750A and the second arm cart 2750B can be nested via partially disposing a portion of the first arm cart 2750A within an interior space of the second arm cart 2750B. Thus, when engaged as shown in FIG. 22, the first arm cart 2750A and the second arm cart 2750B can be moved (e.g., pushed) in unison from one location to another. When desired, the first arm cart 2750A can be separated from the second arm cart 2750B and each arm cart 2750A and 2750B can be moved independently. Although only two arm carts are shown, any suitable number of arm carts shaped similarly to the first arm cart 2750A and the second arm cart 2750B can be nested in series with the first arm cart 2750A or the second arm cart 2750. For example, when the second arm cart 2750B is partially disposed within the interior space of the first arm cart 2750A, a third arm cart (not shown) shaped and sized similarly to the second arm cart 2750B can also be disposed within the interior space of the first arm cart 2750A adjacent the second arm cart 2750B and extending in the opposite direction from the second arm cart 2750B.

Figure 23:
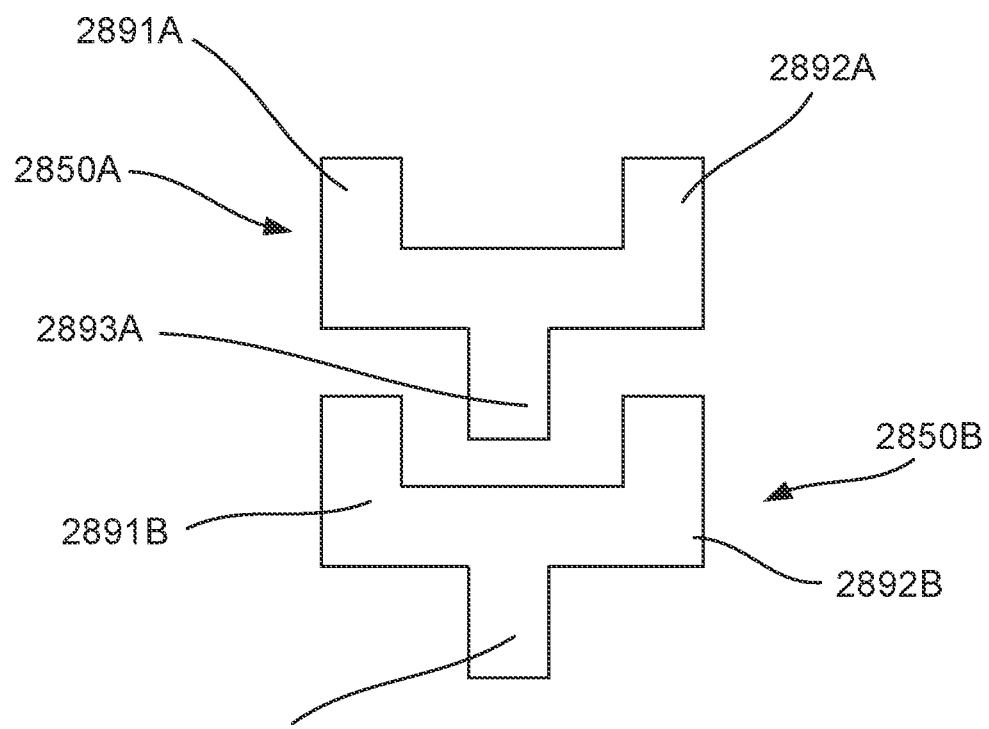
FIG. 23 is a schematic illustration of a top view of two arm carts in a nested configuration, according to an embodiment.

In some embodiments, an arm cart can include a wye-shaped portion and/or can include two front arm portions and one rear arm portion. For example, FIG. 23 is a schematic illustration of a top view of a first arm cart 2850A and a second arm cart 2850B. The first arm cart 2850A and/or the second arm cart 2850B can be the same and/or similar in structure and/or function to the arm cart 350 described above. The first arm cart 2850A can include a first front arm portion 2891A, a second front arm portion 2892A, and a rear arm portion 2893A. The second arm cart 2850B can include a first front arm portion 2891B, a second front arm portion 2892B, and a rear arm portion 2893B. The first arm cart 2850A can be disposed relative to the second arm cart 2850B such that the rear arm portion 2893A can be disposed in a space between the first front arm portion 2891B and the second front arm portion 2892B of the second arm cart 2850B. Thus, when engaged as shown in FIG. 23, the first arm cart 2850A and the second arm cart 2850B can be moved (e.g., pushed) in unison from one location to another. When desired, the first arm cart 2850A and the second arm cart 2850B can be separated from each other and moved independently. Although the second arm cart 2850B is described as receiving the first arm cart 2850A between the first front arm portion 2891B and the second front arm portion 2892B, the first arm cart 2850 can receive the rear arm portion 2893B can be received between the first front arm portion 2891A and the second front arm portion 2892A of the first arm cart 2850A. Although only two arm carts are shown, any suitable number of arm carts shaped similarly to the first arm cart 2850A and the second arm cart 2850B can be nested in series with the first arm cart 2850A or the second arm cart 2850.

In some embodiments, the arm cart 350 (e.g., an arm container and an arm support of the arm cart 350) can be configured to fold or flatten into a compact storage configuration when not being used to transport or store robotic arms. Said another way, the arm cart 350 can be movable from a first, deployed configuration containing and supporting the robotic arm 330 and a second, stowed configuration in which at least one of a vertical, lateral, and longitudinal dimension of the arm cart 350 is less than in the deployed configuration.

The arm cart 350 can include an arm container 352 and a base 354. The arm container 352 is configured to support, protect, and promote sterility for one or more robotic arms 330 (e.g., the first robotic arm 330A and the optional second robotic arm 330B) during transportation of the robotic arms 330, for example, from a storage area to the operating area, and during transfer of the one or more robotic arms 330 from the arm cart 350 to a surgical table (e.g., the surgical table 100 and/or the surgical table 200) for use during the surgical procedure. While the one or more robotic arms 330 are stored and/or transported by the arm cart 350, the one or more robotic arms 330 can be mostly, substantially completely, or completely maintained within the footprint of the arm cart 350 such that the one or more robotic arms 330 will be less likely to be accidentally bumped or damaged. In some embodiments, the arm container 352 can be structured as a vertically-extending protection frame that, in combination with the base 354, defines a space for storing the one or more robotic arms 330. In some embodiments, when the one or more robotic arms 330 are stored within the arm cart 350, the robotic arms can be maintained within the perimeter of the base 354, but may extend beyond the perimeter of the arm container 352.

The arm container 352 can be further configured to facilitate safe, efficient, sterile, and repeatable transfer of the one or more robotic arms 330 to the surgical table and/or an arm adapter. In some embodiments, transfer of the one or more robotic arms 330 from the arm cart 350 to the surgical table can be performed manually.

The base 354 can be configured to support the arm container 352 and provide transportation of the arm cart 350 to the surgical area. The base 354 can include any suitable means for movement of the arm cart 350 relative to the floor. For example, the base 354 can include wheels such that a medical provider can push/pull the arm cart to/from the operating area.

The arm cart 350 can include features that assist in aligning the one or more robotic arms 330 for transfer to the surgical table along the X, Y, and/or Z axes and/or rotationally about the X, Y, and/or Z axes. For example, as described above, the base 354 can include any suitable means for movement of the arm cart 350 such that the arm cart 350 can be moved along the X axis and/or the Y axis relative to the surgical table. Additionally, the arm cart 350 can include any suitable means for adjusting the height of the arm cart 350 and/or the one or more robotic arms 330 such that the height of the one or more robotic arms 330 can be adjusted relative to the surgical table. Thus, the arm cart 350 can move the one or more robotic arms 330 along the X, Y, and/or Z axes and/or rotationally about the X, Y, and/or Z axes such that a coupling portion of at least one of the one or more robotic arms 330 can be aligned for engagement with a mating coupling portion on a table or a table adapter.

In some embodiments, the arm cart 350 houses the one or more robotic arms 330 such that a line of sight can be maintained from the operator of the arm cart 350 to the portion of the surgical table to which the one or more robotic arms 330 are to be transferred during the approach of the arm cart 350 to the surgical table and the transfer of the one or more robotic arms 330 to the surgical table.

Figure 3:
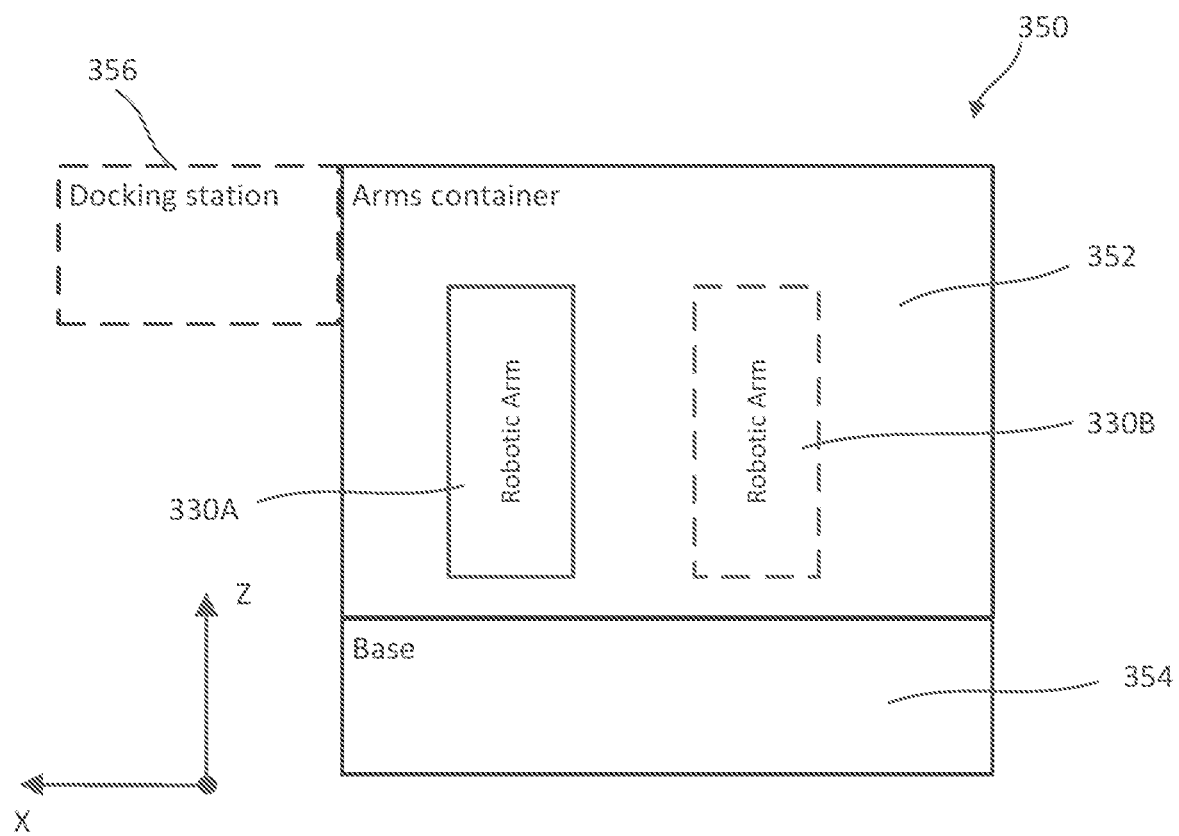
FIG. 3 is a schematic illustration of an arm cart according to an embodiment.

As shown in FIG. 3, the arm cart 350 may optionally include one or more docking stations 356 configured to be releasably attached to the surgical table and/or an arms support connected to the surgical table. In this manner, the arm cart 350 can be fixed to the surgical table and/or arms support during transfer of one or more robotic arms 330 from the arm cart 350, and then the arm cart 350 can be removed from the operating area.

The one or more robotic arms 330 can be docked and/or mounted to the surgical table 300 using a variety of different types of coupling and/or mounting methods and mechanisms. The arm cart 350 can employ corresponding coupling methods and mechanisms to provide efficient transfer of the robotic arms 330 from the arm cart 350 to any suitable location on the surgical table 300 and/or an arms support associated with the surgical table 300. In this manner, the arm cart 350 and the surgical table 300 can include a common interface such that the robotic arms 330 can be efficiently and repeatedly coupled to and/or removed from the surgical table 300 and the arm cart 350.

Figure 4:
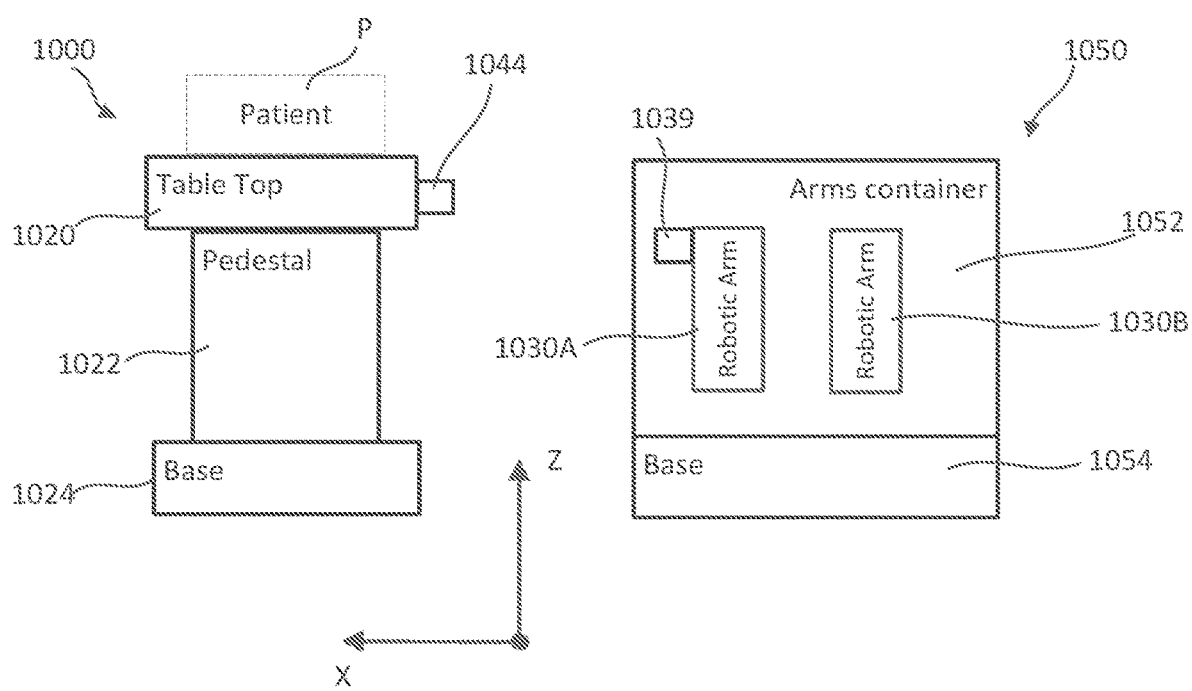
FIG. 4 is a schematic illustration of an arm cart and a surgical table, according to an embodiment.

In some embodiments, a first coupling member associated with the robotic arm can be configured to engage with a second coupling member associated with the surgical table. For example, FIG. 4 is a schematic illustration of an arm cart 1050 and a surgical table 1000. The arm cart 1050 can be the same or similar in structure and/or function to any of the arm carts described herein (e.g., arm cart 350). For example, the arm cart 1050 can include an arm container 1052 and a base 1054. The arm container 1052 is configured to support, protect, and promote sterility for one or more robotic arms 1030 (e.g., a first robotic arm 1030A and a second robotic arm 1030B) during transportation of the robotic arms 1030, for example, from a storage area to the operating area, and during transfer of the robotic arms 1030 from the arm cart 1050 to the surgical table 1000 for use during the surgical procedure. The arm container 1052 is further configured to facilitate safe, efficient, sterile, and repeatable transfer of the surgical arms 1030 to the surgical table 1000. Transfer of the robotic arms 1030 from the arm cart 1050 to the surgical table 1000 may be performed manually. The surgical table 1000 can be the same or similar to any of the surgical tables described herein (e.g., the surgical table 100). For example, the surgical table 1000 includes a table top 1020, a support 1022, and a base 1024. A patient P can be disposed on the table top 1020.

A first coupling member 1039 is coupled to the robotic arm 1030A. A second coupling member 1044 can be coupled to the table top 1020 and/or the pedestal 1022 of the surgical table 1000. The first coupling member 1039 and the second coupling member 1044 (also referred to herein in combination as a "coupler") can include any suitable complementary releasable coupling means. In some embodiments, the arm cart 1050 and/or the surgical table 1000 can include alignment features to assist in achieving the proper alignment (e.g., along and/or about the X, Y, and/or Z axes) between the first coupling member 1039 and/or the second coupling member 1044.

Although the second coupling member 1044 is shown as being disposed to the side of the table top 1020, in some embodiments, the second coupling member can be disposed on the bottom or the top of the table top 1020. Similarly, although the second coupling member 1044 is shown and described as being coupled to the table top 1020, in some embodiments the second coupling member 1044 can be coupled to any suitable portion of the surgical table 1000, such as, for example, the pedestal 1022 or the base 1024.

Figure 5:
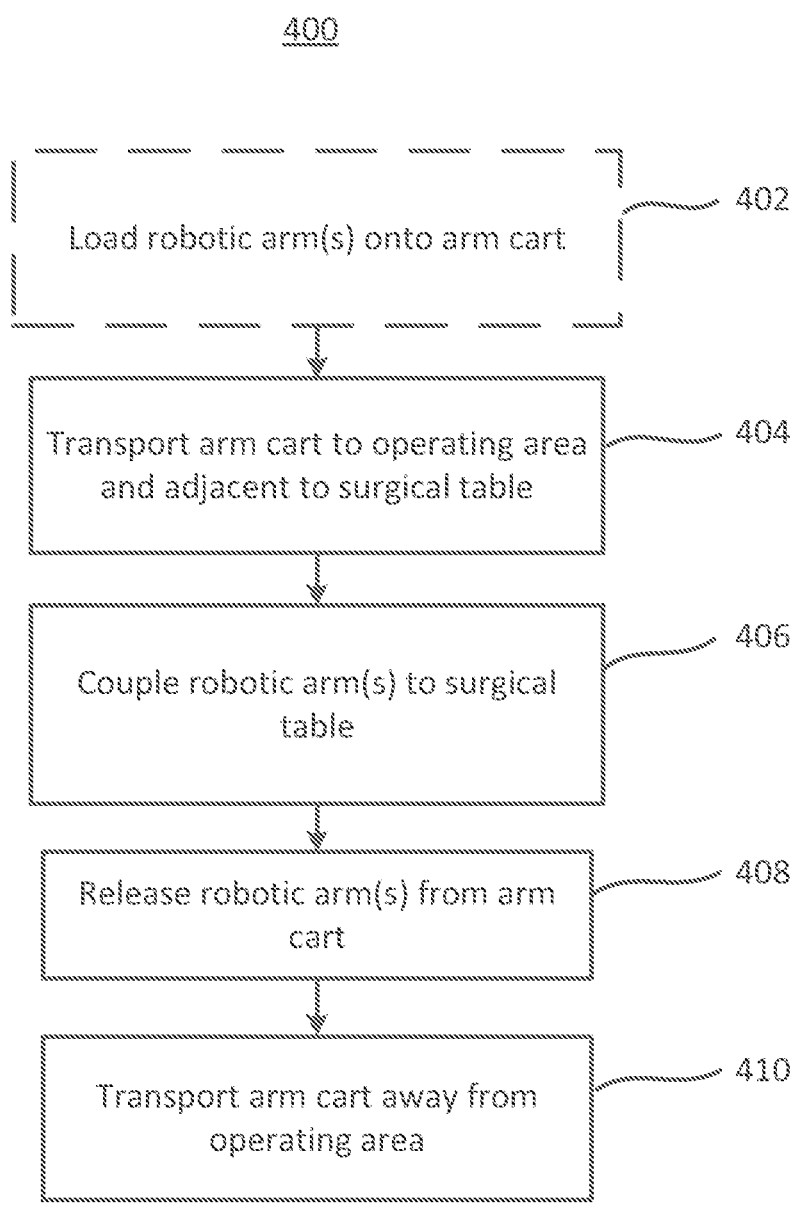
FIG. 5 is a flowchart of a method of using an arm cart to transfer robotic arms to a surgical table, according to an embodiment.

FIG. 5 is a flow chart of a method 400 of transporting and transferring surgical robotic arms to a surgical table using a surgical robotic arm cart, such as any of the arm carts described herein. The method 400 includes optionally loading one or more robotic arms onto an arm cart, at 402. For example, one or more robotic arms can be releasably coupled to an arm support of the arm cart. The arm support can be coupled to a base of the arm cart to support the one or more robotic arms above the base. The base can be freely movable on a support surface. The arm cart is then transported to an operating area and adjacent to a surgical table, at 404. In some embodiments, if not yet disposed in proper alignment with the surgical table, an arm portion of a coupler disposed on at least one of the one or more robotic arms can be disposed in operative relationship with a table portion of a coupler disposed on the surgical table. The one or more robotic arms are coupled to the surgical table, at 406. For example, in some embodiments, the arm portion of the coupler can be releasably coupled to the table portion of the coupler. The one or more robotic arms are released from the arm cart, at 408. The arm cart is transported away from the operating area, at 410.

In some embodiments, rather than loading one or more robotic arms onto the arm cart prior to transporting the arm cart to the operating area and adjacent the surgical table, the one or more robotic arms can be already loaded onto the arm cart. For example, the arm cart could be pre-loaded with one or more robotic arms such that a user does not need to load the arms prior to transporting the cart to an operating area. In some embodiments, the arm cart can serve as a storage system for one or more robotic arms when the arms are not in use such that the user does not need to load the arms onto the arm cart prior to using the arm cart to transport and/or transfer of the one or more robotic arms to the surgical table.

In some embodiments, if a second robotic arm has been loaded onto the arm cart, the arm cart can couple a first robotic arm to the surgical table, release the first robotic arm from the arm cart, and then be transported to a location adjacent another portion of the surgical table. If not yet disposed in proper alignment with the surgical table, an arm portion of a second coupler disposed on the second robotic arm can be disposed in operative relationship with a table portion of a second coupler disposed on the surgical table. The second robotic arm can then be coupled to the surgical table via, for example, the arm portion of the second coupler being releasably coupled to the table portion of the second coupler. The second robotic arm can be released from the arm cart and the arm cart can be transported away from the operating area.

Figure 6A:
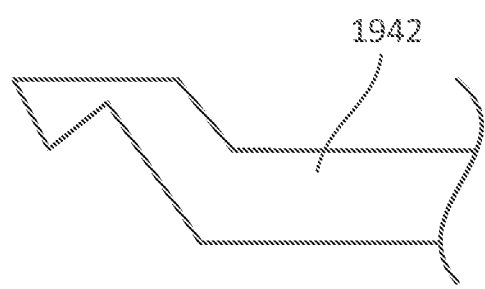
FIGS. 6A and 6B are schematic illustrations of coupling members, according to an embodiment.
Figure 6B:
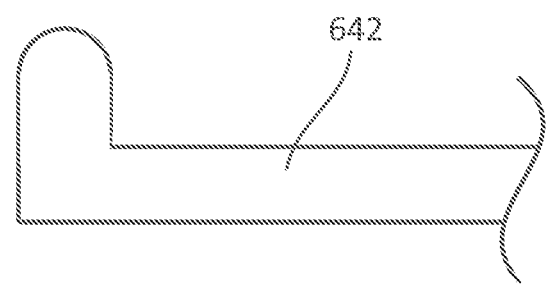

In some embodiments, an arm cart can move a robotic arm within the arm cart such that a coupling member associated with the robotic arm can be presented at a suitable location for engagement with a complementary coupling member associated with a table. For example, the arm cart can adjust the robotic arm to various height settings such that the robotic arm can cooperate with various surgical tables and/or various coupling portions of a surgical table at varying heights. For example, in some embodiments, the arm cart can perform a first macro phase of height adjustment within the arm cart in which the robotic arm cart is set to a high, medium, or low height range. The arm cart can then be moved into position relative to the surgical table such that the coupling member of the robotic arm is aligned with a coupling member associated with the surgical table with respect to the X axis and/or Y axis. Then, in a second micro phase of height adjustment, the arm cart can move the coupling member of the robotic arm cart up or down along the Z axis into engagement with the complementary coupling member of the surgical table. For example, the robotic arm cart can include a coupling member 1942 such as is shown in FIG. 6A and the surgical table can include a dovetail-shaped coupling member (not shown). After the arm cart sets the robotic arm at the appropriate macro setting of high, medium, or low, the arm cart can be moved toward the surgical table. When the arm cart is properly aligned along the X axis and the Y axis, the coupling member 1942 can be lowered (along the Z axis) by the arm cart into engagement with a dovetail-shaped coupling member of the surgical table. Similarly, rather than including the coupling member 1942, a robotic arm can include a coupling member 642 shaped such as is shown in FIG. 6B. When the arm cart is properly aligned along the X axis and the Y axis, the coupling member 642 can be raised (along the Z axis) into engagement with a dovetail-shaped coupling member of the surgical table. Although not shown, in some embodiments, a robotic arm can include both the coupling member 1942 and the coupling member 642 such that the coupling member 1942 can be moved down along the Z axis and the coupling member 642 can be moved up along the Z axis to sandwich a coupling member of a surgical table.

Figure 7A:
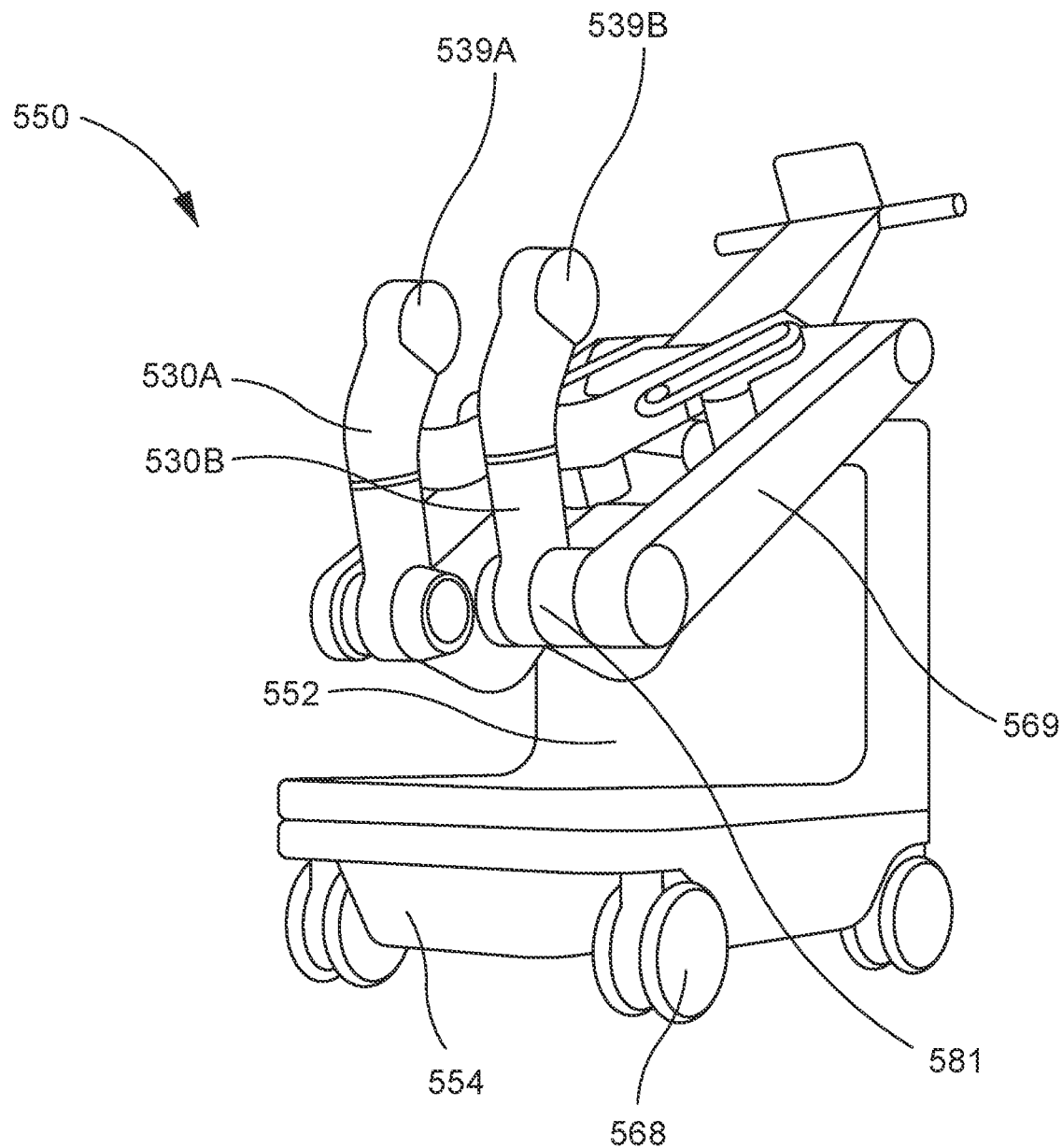
FIGS. 7A-7C show various views of an arm cart in a variety of configurations, according to an embodiment.
Figure 7B:
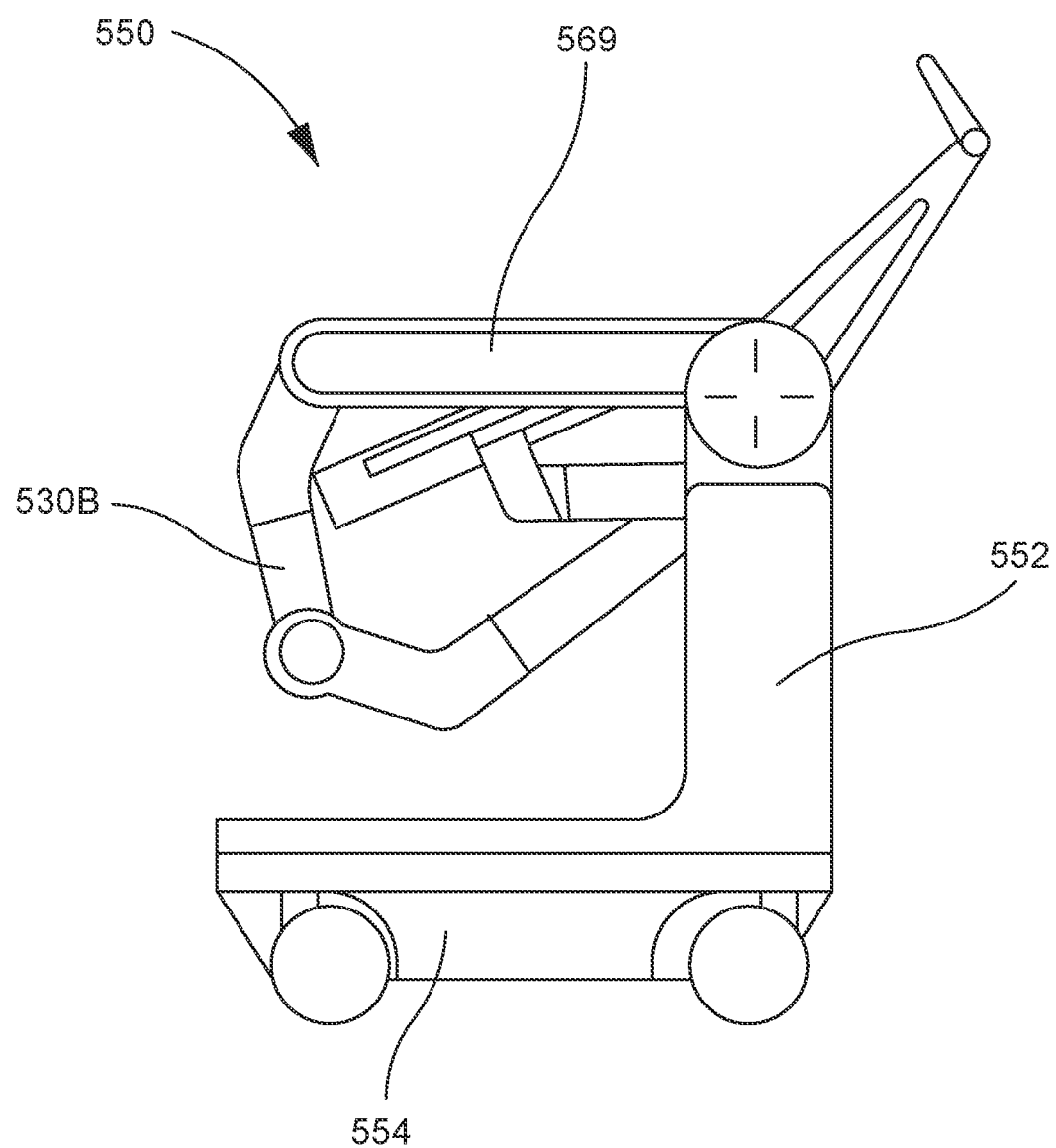
Figure 7C:
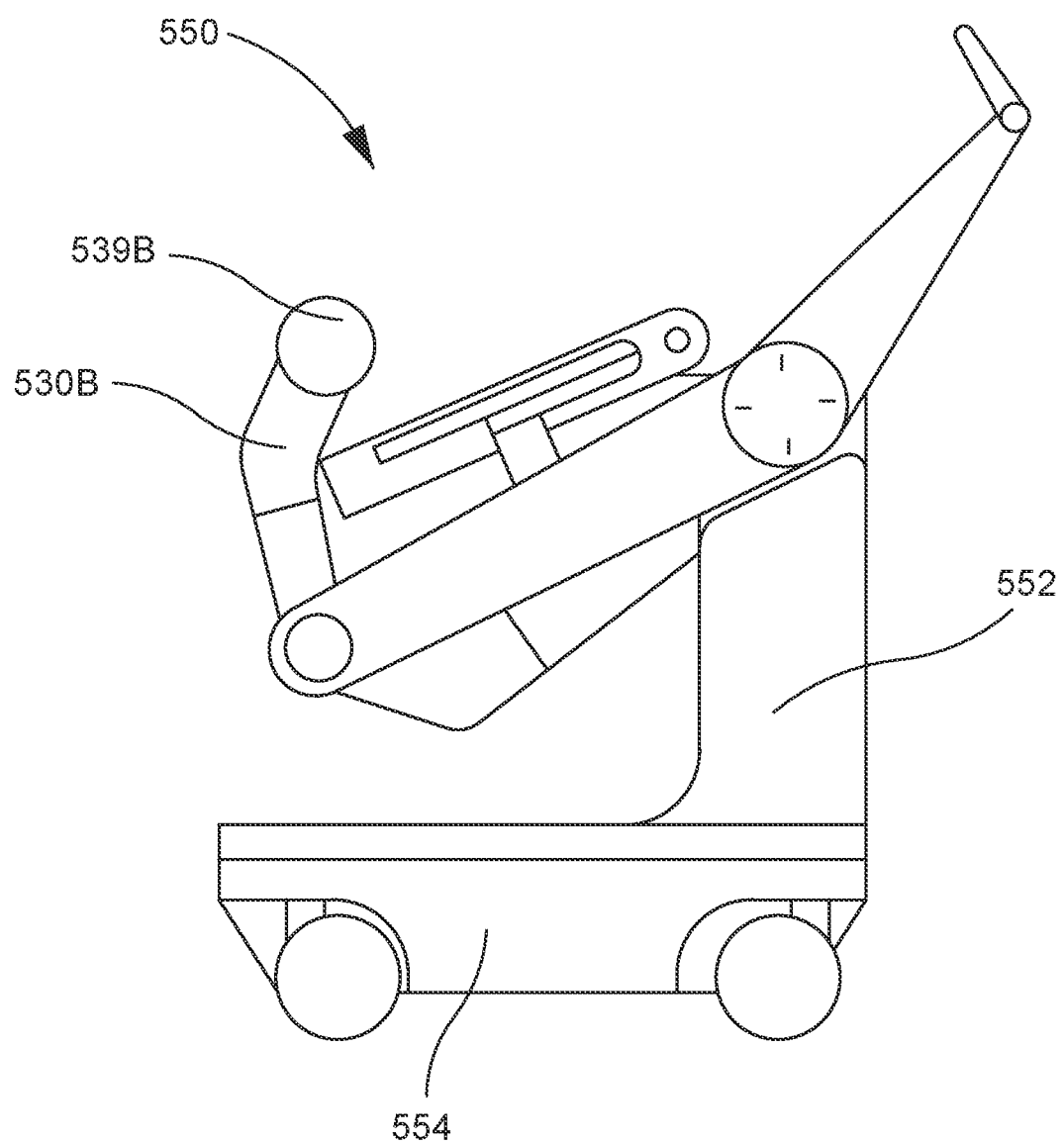

FIGS. 7A-7C show various views of an arm cart 550 in a variety of configurations, according to an embodiment. FIG. 7A is a perspective view of the arm cart 550. The arm cart 550 includes an arm container 552 and a base 554. A first robotic arm 530A and a second robotic arm 530B are releasably mounted to the arm cart 550. The arm container 552 can include an arm support 569 coupled to the base 554 and releasably couplable to the robotic arms 530 above the base. The base 554 can be freely moveable on a support surface, such as, for example, a floor, between a first location remote from a surgical table and a second location adjacent to the surgical table. For example, the base 554 can be coupled to a number of wheels 568, such as, for example, three or four wheels, such that the arm cart 550 is moveably supported on the support surface. The first robotic arm 530A can include an arm coupling member 539A (also referred to as an "arm portion of a coupler"), and the second robotic arm 530B can include an arm coupling member 539B. As shown in FIG. 7A, the arm support 569 can be coupled to the robotic arms 530 at a support location 581 on each of the robotic arms 530, and the support location 581 can be spaced from the coupler 539 of each robotic arm 530.

The base 554, the arm container 552, and the arm support 569 can permit and/or control movement of the robotic arms 530 along and/or about the X, Y, and/or Z axes. When the base 554 is at the second location adjacent to the surgical table, the arm support 569 and/or the arm container 552 can permit movement of one or both of the robotic arms 530 between a first position in which one or both of the arm coupling members 539 are not engageable with a coupling site of the surgical table and a second position in which one or both of the arm coupling members 539 are engageable with the coupling site of the surgical table. In some embodiments, at least one of the arm coupling members 539 (e.g., the first arm coupling member 539A) can be an arm portion of a coupler and a table portion of the coupler can be disposed on a surgical table. The arm support 569 can move the first robotic arm 530A such that the arm coupling member 539A is disposed in operative relationship with the table portion of the coupler.

For example, FIG. 7B is a side view of the arm cart 550 in a stowed configuration in which the first robotic arm 530A and the second robotic arm 530B are disposed within the arm container 552. In the stowed configuration, the first robotic arm 530A and the second robotic arm 530B can be transported via the arm cart 550. FIG. 7C is a side view of the arm cart 550 in a partially unfolded or deployed configuration in which the first robotic arm 530A and the second 530B have been rotated relative to the arm cart 550. The first robotic arm 530A and the second robotic arm 530B can each include one or more joints configured to engage with the arm support 569 of the arm cart 550 such that the arm cart 550 can control the orientation and position of each of the robotic arms 530 relative to the arm cart 550. The rotation of the first robotic arm 530A and the second robotic arm 530B can expose an arm coupling member of each of the first robotic arm 530A and the second robotic arm 530B such that each of the arm coupling members 539 are properly disposed for coupling to a surgical table, such as to a table portion of a coupler.

In some embodiments, after the first arm coupling member 539A has been disposed in operative relationship with a table portion of the coupler disposed on the surgical table, the first arm coupling member 539A can be releasably coupled to the table portion of the coupler. The first robotic arm 530A can then be uncoupled from the arm cart 550 and the arm cart 550 can be moved on the support surface away from the location adjacent the surgical table. In some embodiments, after the first robotic arm 530A has been releasably coupled to the surgical table, the arm cart 550 can be moved to a third location adjacent another portion of the surgical table. The second arm coupling member 539B can then be disposed in operative relationship with a table portion of a second coupler disposed on the surgical table. The second arm coupling member 539B can then be releasably coupled to the table portion of the second coupler. The second robotic arm 530B can then be uncoupled from the arm cart 550 and the arm cart 550 can be moved on the support surface away from the third location.

Figure 8A:
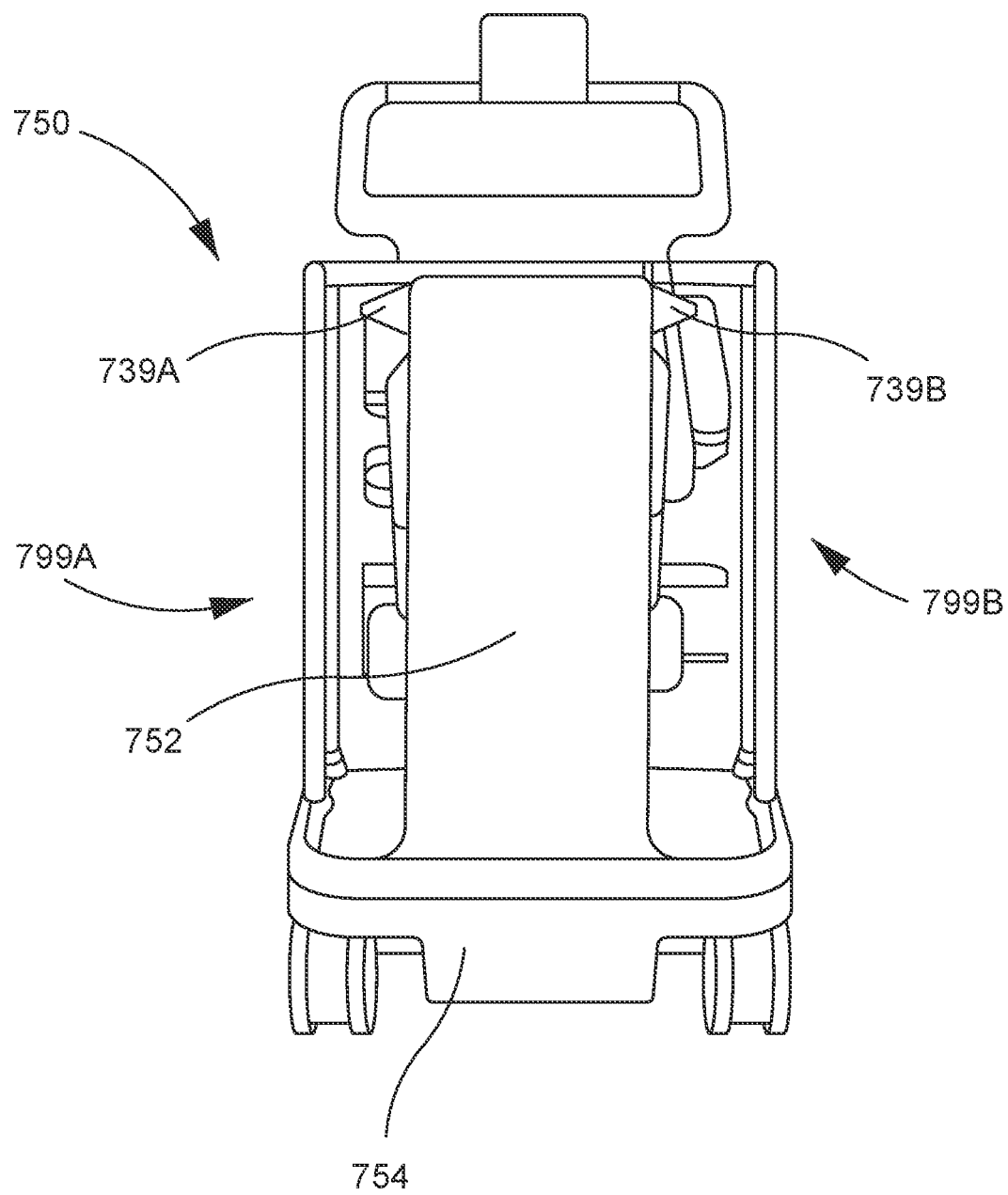
FIGS. 8A and 8B show a back and top view of an arm cart, according to an embodiment.
Figure 8B:
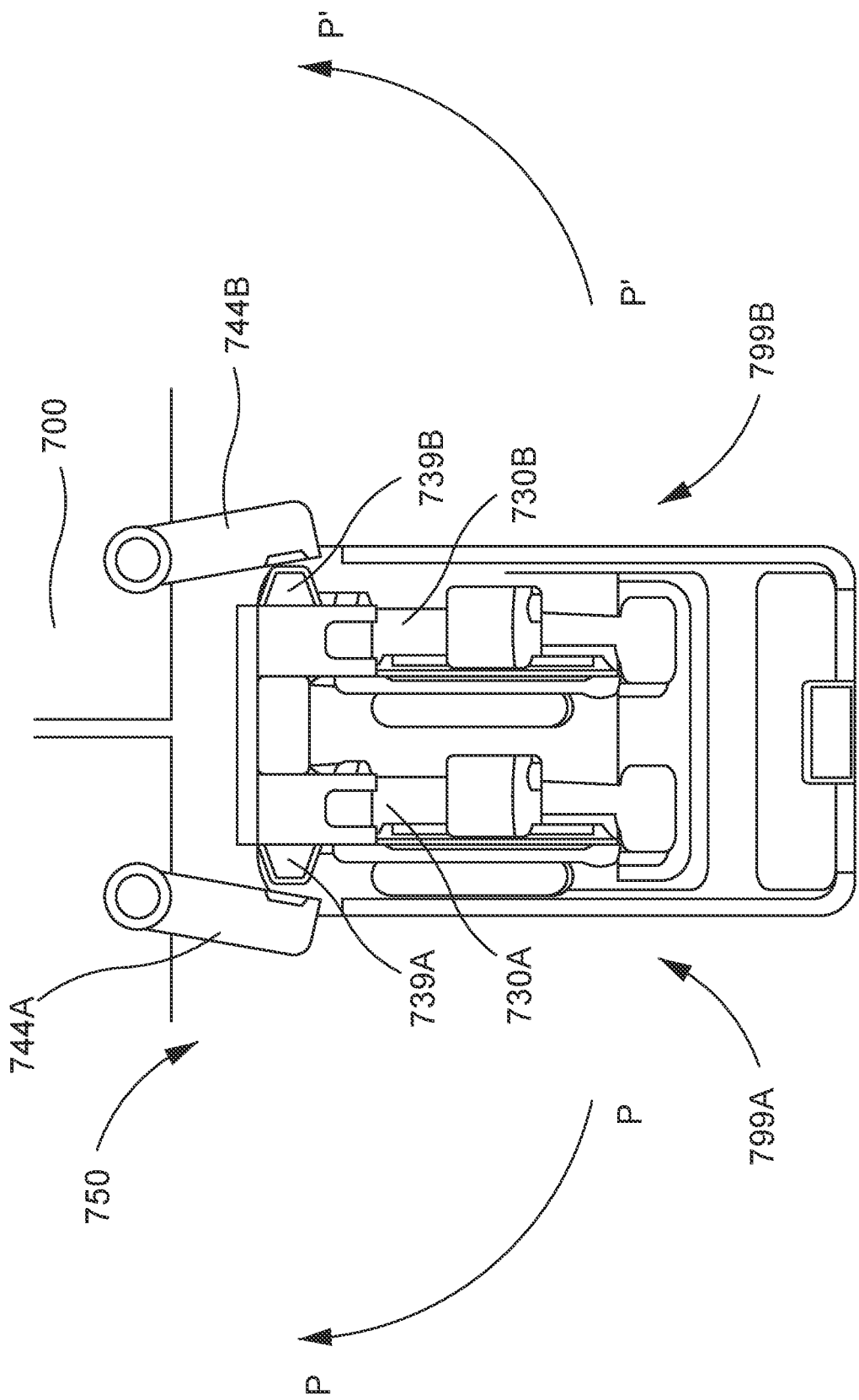

FIGS. 8A and 8B show a back and top view of an arm cart 750, according to an embodiment. The arm cart 750 can be the same or similar in structure and/or function to the arm cart 550 described with respect to FIGS. 7A-7C. As shown in FIG. 8A, the arm cart 750 includes an arm container 752 and a base 754. The arm cart 750 is configured to store, protect, and transport a first robotic arm 730A (shown in FIG. 8B) and a second robotic arm 730B (also shown in FIG. 8B). The arm container 752 can define side openings (e.g., first side opening 799A and second side opening 799B) such that the first robotic arm 730A and/or the second robotic arm 730B can be transferred into the arm container 752 and removed from the arm container 752 via the side openings 799A, 799B. The first robotic arm 730A includes a first arm coupling member 739A and the second robotic arm 730B includes a second arm coupling member 739B. As shown in FIG. 8B, the first robotic arm 730A and the second arm 730B are configured to engage with a surgical table 700. More specifically, the first arm coupling member 739A is configured to engage with a coupling member 744A rotatably attached to the surgical table 700 and the second arm coupling member 739B is configured to engage with a coupling member 744B rotatably attached to the surgical table 700. When the first arm coupling member 739A is engaged with the coupling member 744A, the first arm coupling member 739A can rotate the first robotic arm 730A laterally out of a side of the arm cart 750 via side opening 799A along, for example, arrow P-P. Similarly, when the second arm coupling member 739B is engaged with the coupling member 744B, the second arm coupling member 739B can rotate the second robotic arm 730B laterally out of a side of the arm cart 750 via side opening 799B along, for example, arrow P'-P'. Thus, the arm cart 750 can transfer the first robotic arm 730A and the second robotic arm 730B from the arm cart 750 to the surgical table 700. In some embodiments, the first coupling member 739A and the second coupling member 739B can rotate the first robotic arm 730A and the second robotic arm 730B, respectively, out of the arm cart 750 simultaneously. In some embodiments, the first coupling member 739A and the second coupling member 739B can rotate the first robotic arm 730A and the second robotic arm 730B, respectively, out of the arm cart 750 sequentially. In some embodiments, only one of the first robotic arm 730A and the second robotic arm 730B can be rotated out of the arm cart by the first coupling member 739A or the second coupling member 739B, respectively, and the remaining first robotic arm 730A or second robotic arm 730B can be stored in the arm cart 750 until a later time.

Figure 9:
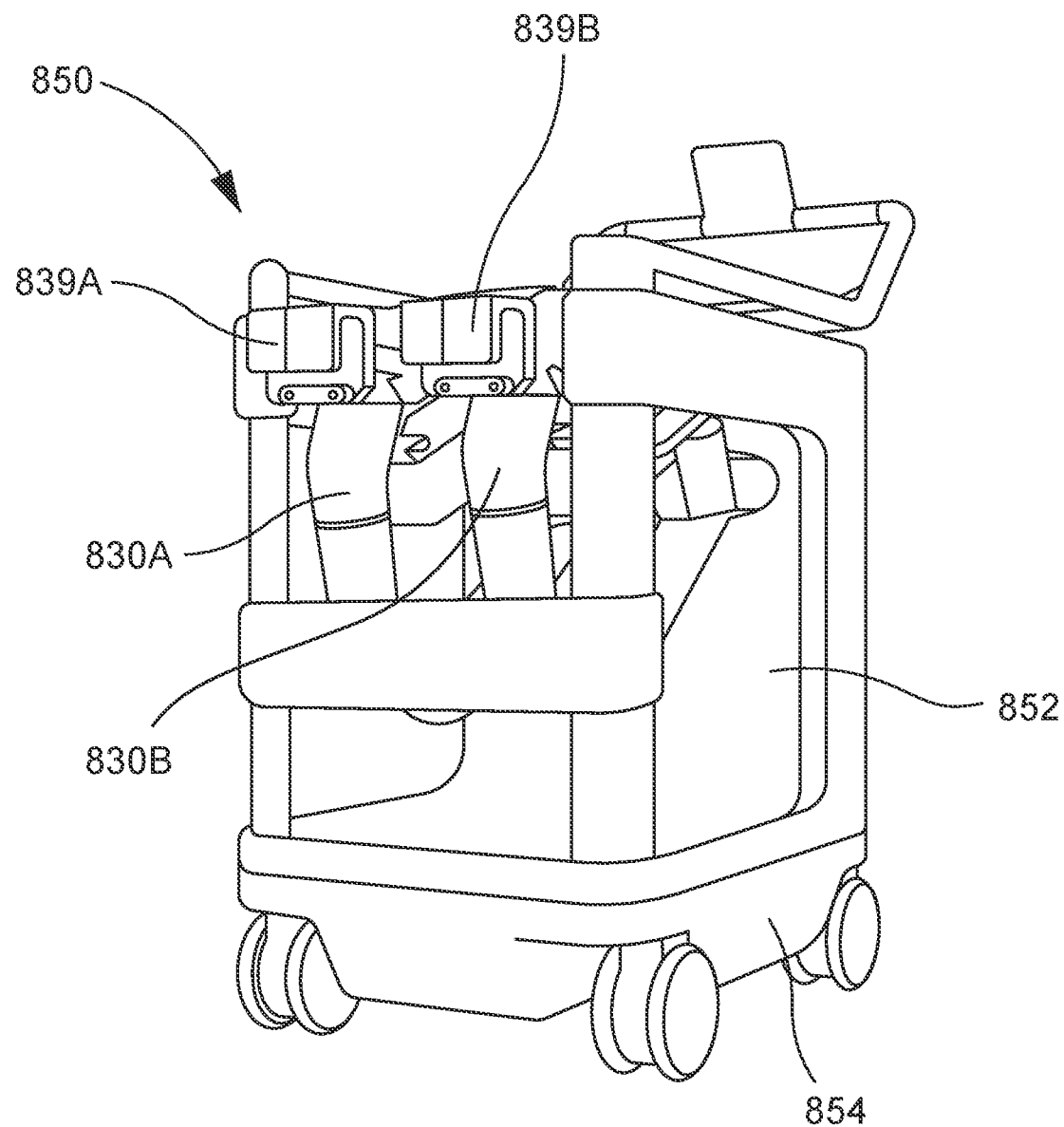
FIG. 9 is a perspective view of an arm cart, according to an embodiment.

FIG. 9 is a perspective view of an arm cart 850, according to an embodiment. The arm cart 850 can be the same or similar in structure and/or function to the arm cart 550 described with respect to FIGS. 7A-7C. As shown in FIG. 9, the arm cart 850 includes an arm container 852 and a base 854. A first robotic arm 830A and a second robotic arm 830B are releasably mounted to the arm cart 850. The first robotic arm 830A includes a coupling member 839A and the second robotic arm 830B includes a coupling member 839B. The first coupling member 839A and the second coupling member 839B both include latch shaped elements such that the first coupling member 839A and the second coupling member 839B are configured to couple the first robotic arm 830A and the second robotic arm 830B to a surgical table (not shown).

Figure 10A:
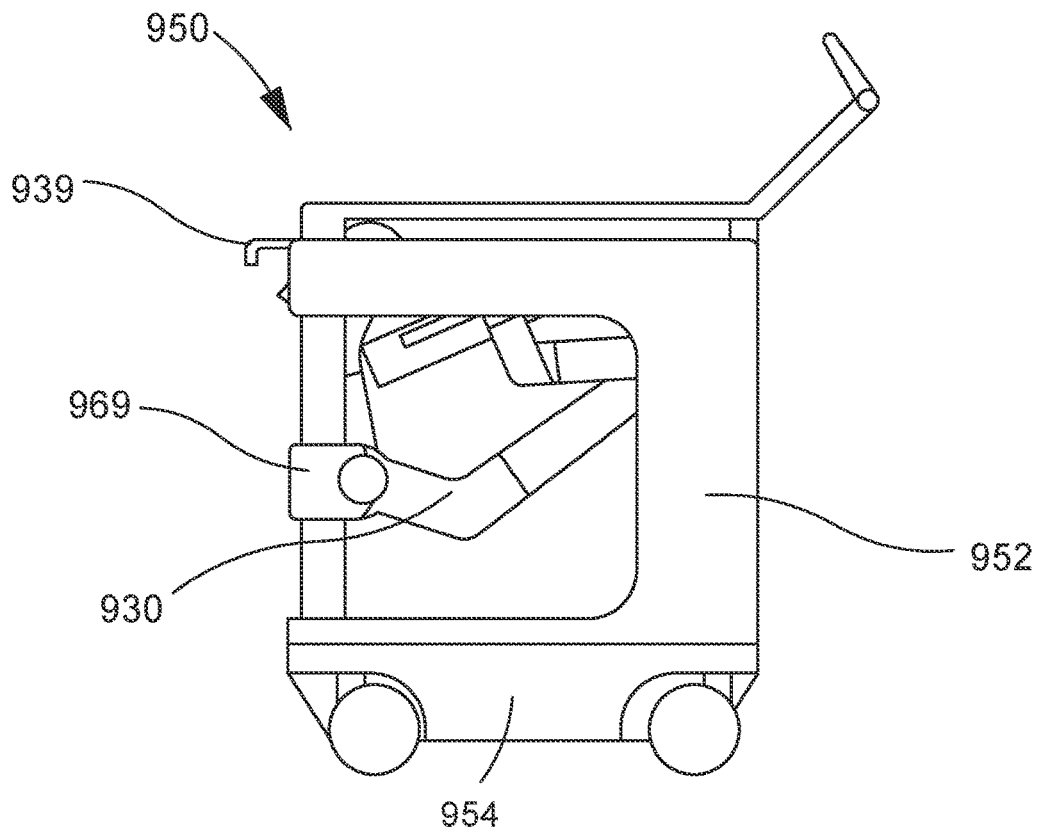
FIGS. 10A and 10B show a side view of an arm cart in a first configuration and a second configuration, according to an embodiment.
Figure 10B:
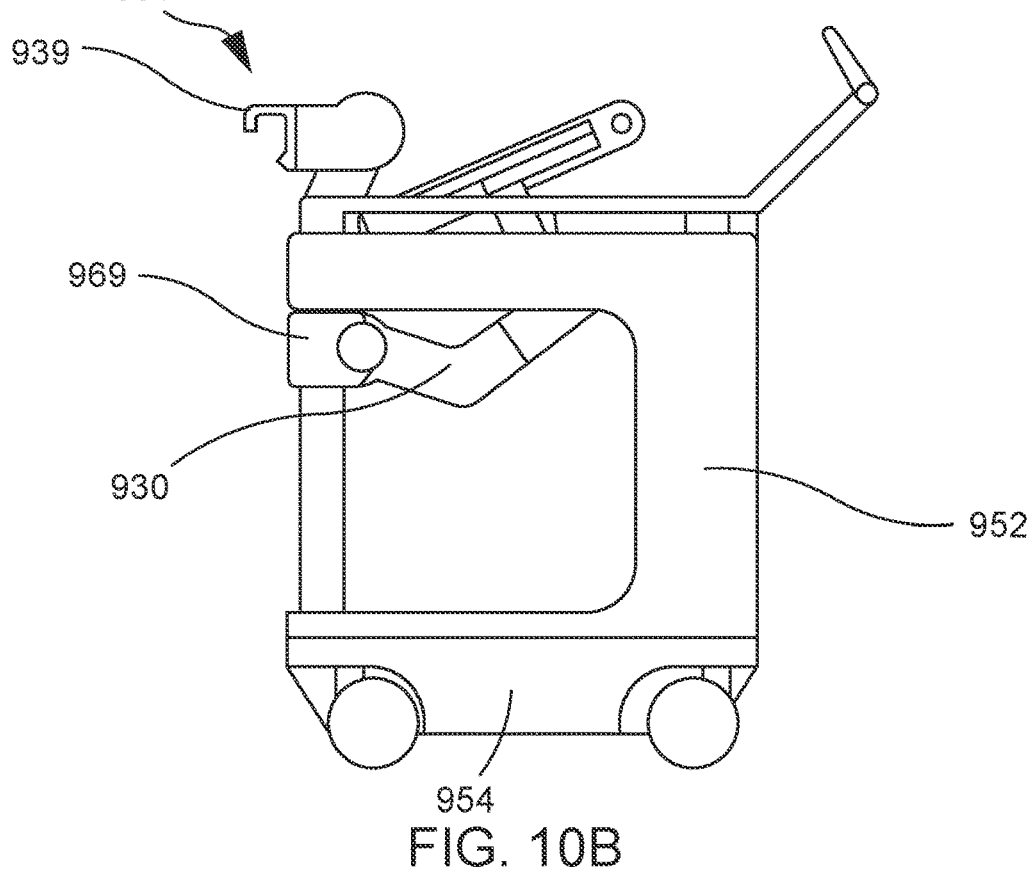

FIGS. 10A and 10B show a side view of an arm cart 950 in a first, stowed configuration and a second, deployed configuration, according to an embodiment. The arm cart 950 can be the same or similar in structure and/or function to any of the arm carts described herein, such as arm cart 550 described with respect to FIGS. 7A-7C. FIG. 10A is a side view of the arm cart 950 in a stowed configuration. The arm cart 950 includes an arm container 952 and a base 954. The base 954 can be freely moveable on a support surface, such as, for example, a floor, between a first location remote from a surgical table and a second location adjacent to the surgical table. The arm container 952 can be coupled to and extend upwardly from the base 954. An arm support 969 can be coupled to the arm container 952 and/or the base 954. The arm support 969 can be releasably coupleable to a robotic arm 930 to support the robotic arm 930 and/or control the position of the robotic arm 930. The robotic arm 930 can include a coupler 939 releasably coupleable to a coupling site on a surgical table (not shown). Although only one robotic arm 930 is shown and described, any suitable number of robotic arms can be stored, transported, and/or transferred by the arm cart 950.

In the stowed configuration, the entire robotic arm 930 except the coupler 939 can be substantially disposed or contained within the arm container 952 and can be stored, protected, and transported via the arm cart 950. During movement of the arm cart 950 on the support surface, the arm container 952 can protect the robotic arm 930 from impact with objects. As shown in FIG. 10B, which is a side view of the arm cart 950 in a partially unfolded or deployed configuration, the arm support 969 can move the robotic arm 930 linearly upward along the Z-axis.

In use, with the arm cart 950 in the stowed configuration shown in FIG. 10A, the arm cart 950 can be moved on the support surface from the first location remote from the surgical table to the second location adjacent the surgical table. When the arm cart 950 is adjacent the surgical table and the arm cart 950 is in the stowed configuration, the coupler 939 may not be engageable with the coupling site of the surgical table. The arm support 969 can then permit movement of the robotic arm 930 (e.g., via lifting the robotic arms 930 along the Z axis) between the stowed position and the deployed position in which the coupler 939 is engageable with the coupling site when the base 954 is at the second location.

Figure 11:
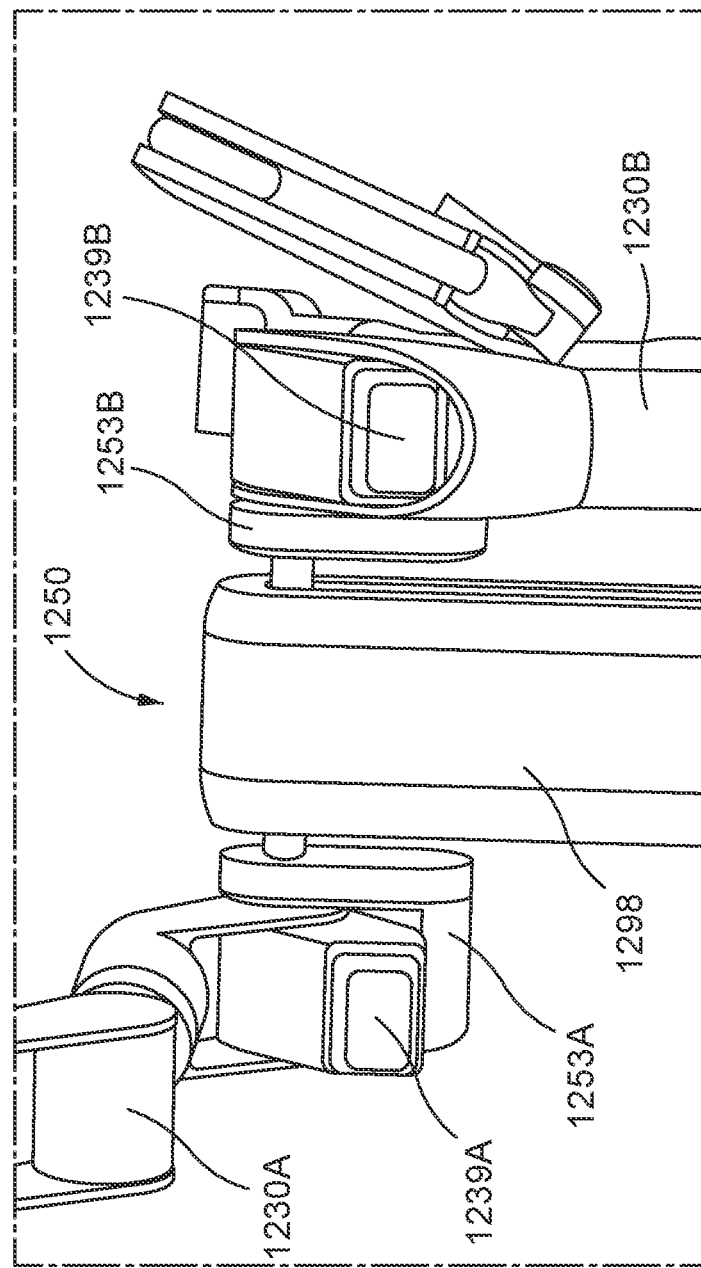
FIG. 11 is a schematic illustration of a portion of an arm cart supporting two robotic arms, according to an embodiment.

FIG. 11 is a schematic illustration of a portion of an arm cart supporting two robotic arms. As shown in FIG. 11, the arm cart 1250 includes a vertical post 1298. The vertical post can provide at least one translation path for robotic arms along the Z-axis. The arm cart 1250 also includes a first arm cradle 1253A and a second arm cradle 1253B. The first arm cradle 1253A is configured to support a first robotic arm 1230A and the second arm cradle 1253B is configured to support a second robotic arm 1230B. The first arm cradle 1253A is also configured to control the rotational position of at least a portion of the first robotic arm 1230A relative to the vertical post 1298 and/or a surgical table. Similarly, the second arm cradle 1253A is also configured to control the rotational position of at least a portion of the second robotic arm 1230B relative to the vertical post 1298 and/or a surgical table. The first robotic arm 1230A includes a first arm coupling member 1239A. Similarly, the second robotic arm 1230B includes a second arm coupling member 1239B.

The arm cart 1250 can rotate the first arm cradle 1253A and can translate the first arm cradle 1253A along a Z-axis translation path. Thus, when a first robotic arm 1230A is disposed in the first arm cradle 1253A, the arm cart 1250 can control the Z-axis and rotational positions of the first arm cradle 1253A and the first robotic arm 1230A. The arm cart 1250 can rotate the first robotic arm 1230A such that the first arm coupling member 1239A is exposed and positioned for engagement with a surgical table, as shown in FIG. 11. In such a position, the first robotic arm 1230A can be disposed in the first arm cradle 1253A such that the first robotic arm 1230A extends vertically upward from the first arm cradle 1253A. Additionally, the first arm cradle 1253A can rotate the first robotic arm 1230A, for example, from the configuration and orientation of the first robotic arm 1230A shown in FIG. 11 to the configuration and orientation of the second robotic arm 1230B shown in FIG. 11.

Similarly, the arm cart 1250 can rotate the second arm cradle 1253B and can translate the second arm cradle 1253B along a Z-axis translation path. Thus, when a second robotic arm 1230B is disposed in the second arm cradle 1253B, the arm cart 1250 can control the Z-axis and rotational positions of the second arm cradle 1253B and the second robotic arm 1230B. The arm cart 1250 can rotate the second robotic arm 1230B such that the second arm coupling member 1239B is exposed and positioned for engagement with a surgical table, as shown in FIG. 11. In such a position, the second robotic arm 1230B can be disposed in the second arm cradle 1253B such that the second robotic arm 1230B extends vertically downward from the second arm cradle 1253B. Additionally, the second arm cradle 1253B can rotate the second robotic arm 1230B, for example, from the configuration and orientation of the second robotic arm 1230B shown in FIG. 11 to the configuration and orientation of the first robotic arm 1230A shown in FIG. 11.

Figure 12:
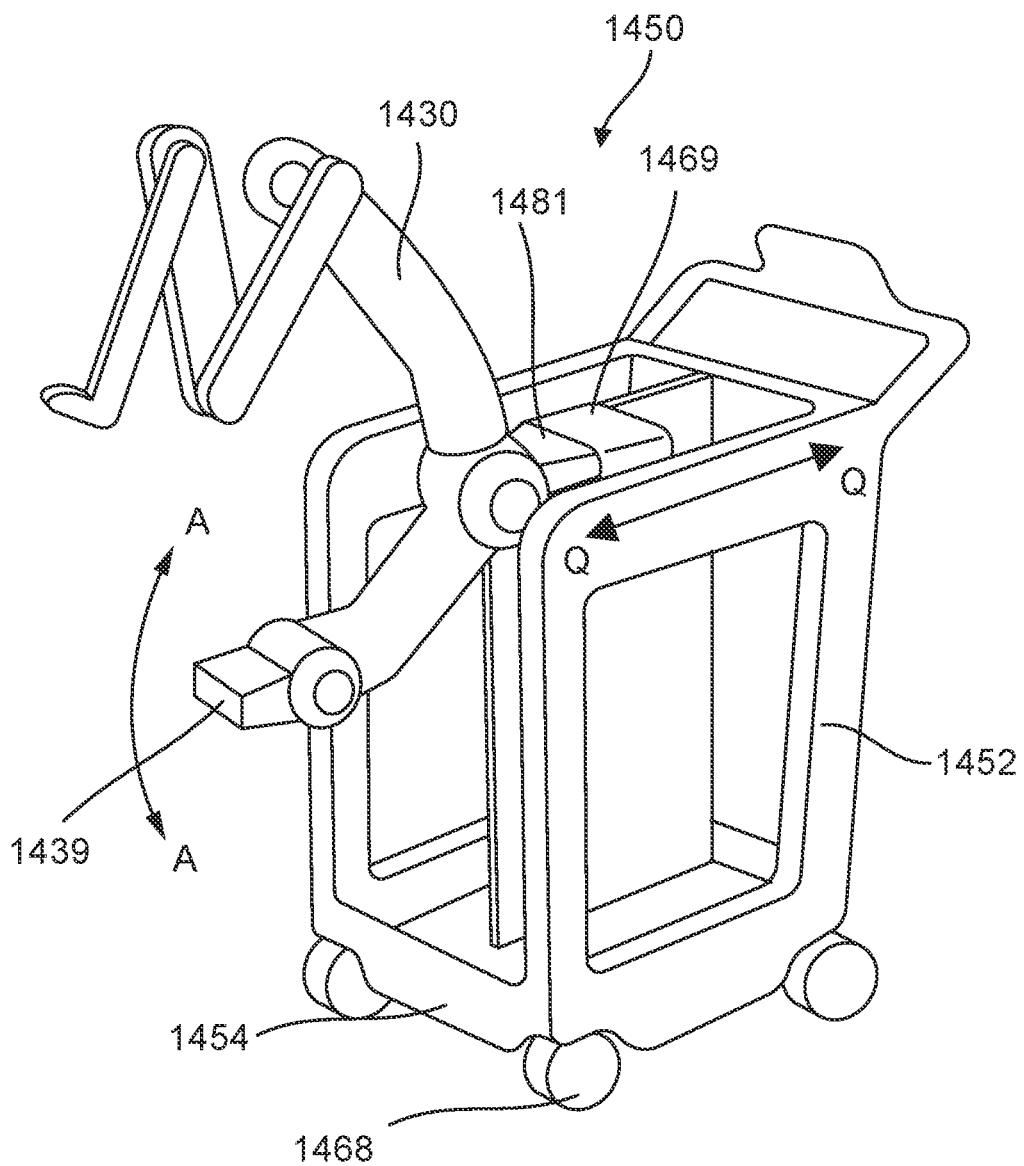
FIG. 12 is a perspective view of an arm cart in a docking configuration, according to an embodiment.

FIG. 12 is a perspective view of an arm cart in a docking configuration. As shown in FIG. 12, an arm cart 1450 can include an arm container 1452, a base 1454, and an arm support or carriage 1469. The arm cart 1450 can be the same or similar in structure and/or function to any of the arm carts described herein. For example, the base 1454 can be freely moveable on a support surface, such as, for example, a floor, between a first location remote from a surgical table and a second location adjacent to the surgical table. The base 1454 can be coupled to a number of wheels 1468, such as, for example, three or four wheels, such that the arm cart 1450 is moveably supported on the support surface. The arm support 1469 can translate relative to the arm container 1452 along arrow Q-Q between, for example, the docking position shown in FIG. 12 and a stowed or transport position (not shown). A robotic arm 1430 is releasably mounted to the arm cart 1450 via the arm support 1469. The robotic arm 1430 includes an arm coupling member 1439 (also referred to as a "coupler"). The arm support 1469 is coupleable to the robotic arm 1430 at a support location 1481 (e.g., an intermediate pivot joint distal to the coupler 1439) on the arm, the support location 1481 being spaced from the arm coupling member 1439. When the robotic arm 1430 is in a stowed position (not shown) in which the robotic arm 1430 is at least partially disposed within the arm container 1452, the arm cart 1450 is configured to support the robotic arm 1430 with the center of gravity of the arm 1430 being below the arm support 1469. Additionally, when the robotic arm 1430 is in the stowed position, the arm container 1452 is configured to protect the robotic arm 1430 from impact with objects during movement of the arm cart 1450.

As shown in FIG. 12, the robotic arm 1430 can be translated by the arm support 1469 relative to the arm container 1452 along arrow Q-Q from a stowed to a docking position. Additionally, when in the docking configuration shown in FIG. 12, at least a portion of the robotic arm 1430 can move rotationally relative to the arm support 1469 along arrow A-A from the stowed configuration to a docking configuration (as shown in FIG. 12). The rotation of the robotic arm 1430 can expose the side of the arm coupling member 1439 configured for coupling to a table such that the arm coupling member 1439 is properly disposed for coupling to the table. In the docking configuration shown in FIG. 12, the arm cart 1450 can move into position relative to a surgical table such that the arm coupling member 1439 can couple with a mating coupling member associated with the surgical table. Said another way, when in the stowed configuration, the arm coupling member 1439 is disposed within the arm container 1452. When in the deployed configuration, the arm coupling member 1439 is disposed outside of the arm container 1452. As shown in FIG. 12, the arm coupling member 1439 is proximate to a first end of the robotic arm 1430, the support location 1481 is proximate to a second end of the robotic arm 1430 opposite the first end of the robotic arm 1430, and the arm cart 1450 is configured to support the robotic arm 1430 with the arm coupling member 1439 disposed below the support location 1481 when the robotic arm 1430 is disposed in the docking configuration. Once in the docking configuration and properly aligned with a coupling site of a surgical table, the robotic arm 1430 can be transferred to the surgical table and the arm cart 1450 can be moved away from the surgical table.

Although not shown, in some embodiments the arm cart 1450 can be configured to support and transfer a second robotic arm to a second coupling site on a surgical table. In such embodiments, the arm cart 1450 can include a second arm support. A second robotic arm can be loaded onto the arm cart 1450 and into engagement with the second arm support. After transferring the robotic arm 1430 to a first coupling site of a surgical table as described above, the arm cart 1450 can be moved, with the second robotic arm in a stowed configuration, via the base 1454 to another location near the surgical table. The second arm support can then rotate the second robotic arm similarly as described above from the stowed configuration to the deployed configuration such that an arm coupling member of the second robotic arm can be disposed in a proper position for engagement with a second mating coupling member associated with the surgical table. Once in the docking configuration and properly aligned with a coupling site of a surgical table, the second robotic arm can be transferred to the surgical table and the arm cart 1450 can be moved away from the surgical table.

Figure 13A:
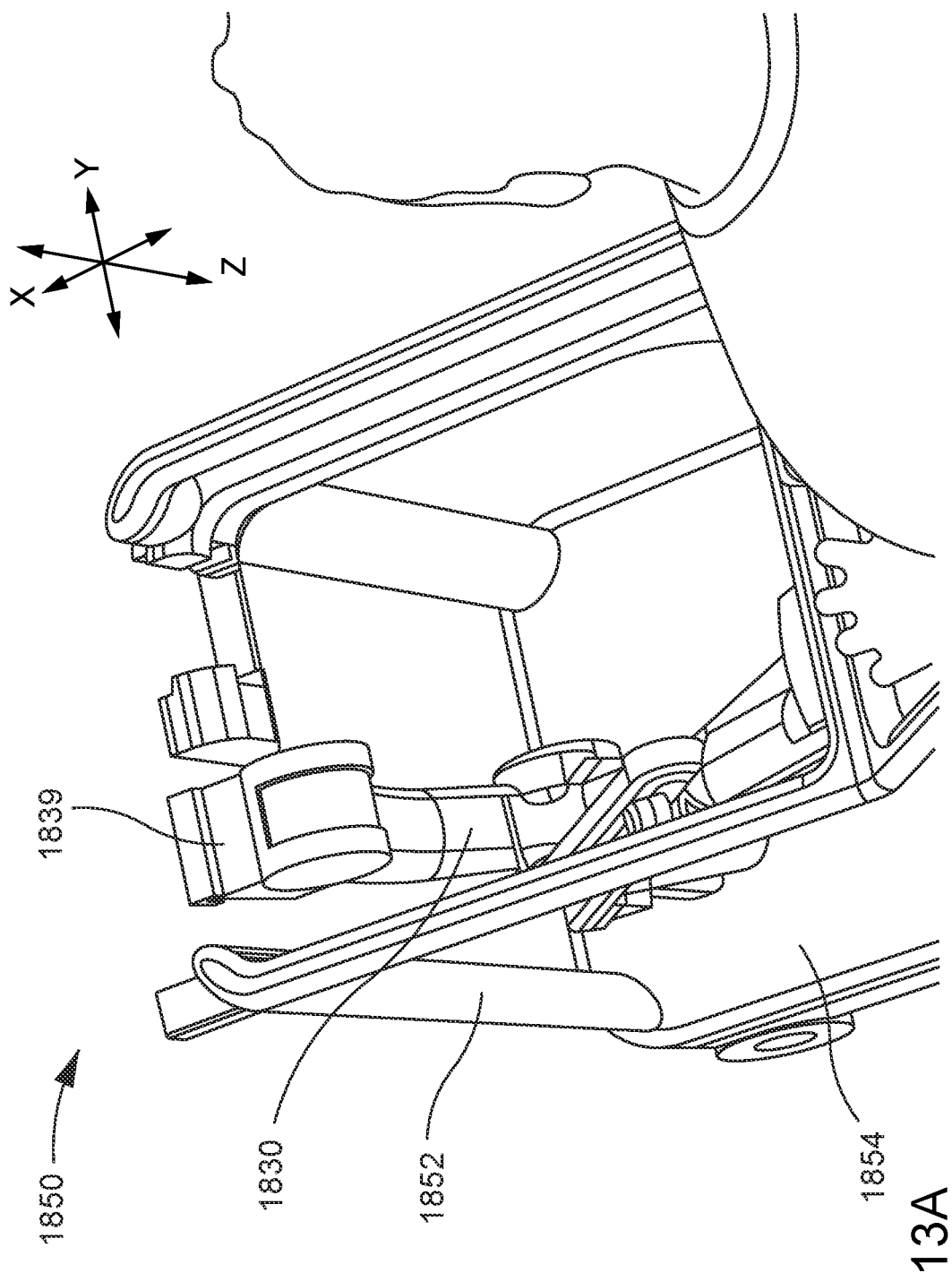
FIGS. 13A-13F are various views of an arm cart in a variety of configurations, according to an embodiment.
Figure 13B:
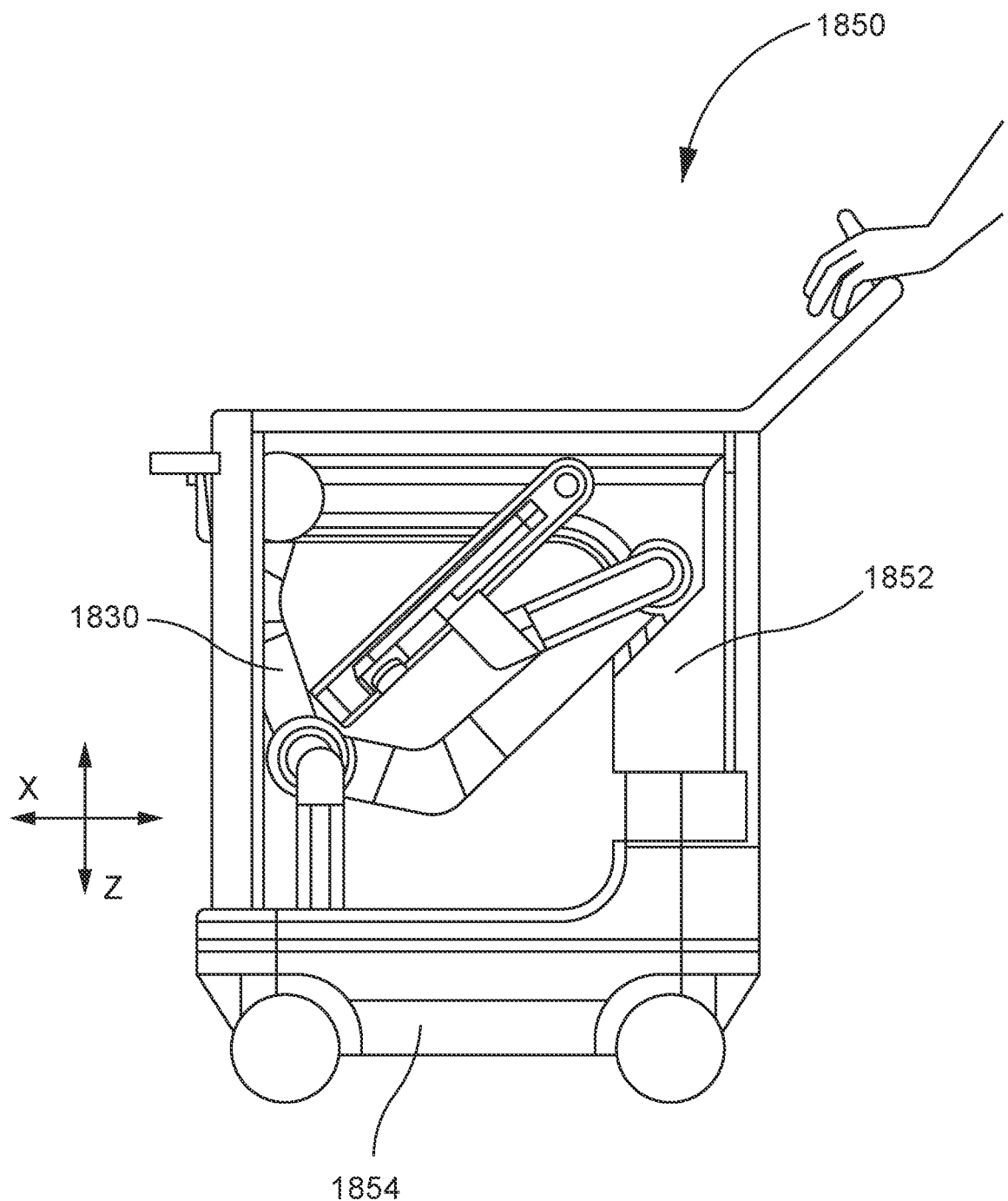

FIGS. 13A-13F are various views of an arm cart 1850 in a variety of configurations. The arm cart 1850 can be the same or similar in structure and/or function to any of the arm carts described herein. For example, FIGS. 13A and 13B are a perspective view and a side view of the arm cart 1850, respectively. The arm cart 1850 can include an arm container 1852 and a base 1854. The arm container 1852 is configured to support, protect, and promote sterility for a robotic arm 1830 during transportation of the robotic arm 1830, for example, from a storage area to the operating area, and during transfer of the robotic arm 1830 from the arm cart 1850 to a surgical table for use during the surgical procedure. The arm container 1852 can be coupled to the base 1854 and releasably couplable to the robotic arm 1830 above the base. The base 1854 can be freely moveable on a support surface, such as, for example, a floor, between a first location remote from a surgical table and a second location adjacent to the surgical table. For example, the base 1854 can be coupled to a number of wheels 1868, such as, for example, three or four wheels, such that the arm cart 1850 is moveably supported on the support surface. The robotic arm 1830 includes an arm coupling member 1839 (also referred to as a "coupler"). The base 1854 and the arm container 1852 can permit and/or control movement of the robotic arm 1830 along and/or about the X, Y, and/or Z axes. When the base 1854 is at the second location adjacent to the surgical table, the arm container 1852 can permit movement of the robotic arm 1830 between a first position in which the arm coupling member 1839 is not engageable with a coupling site of the surgical table and a second position in which the arm coupling member 1839 is engageable with the coupling site of the surgical table.

Figure 13C:
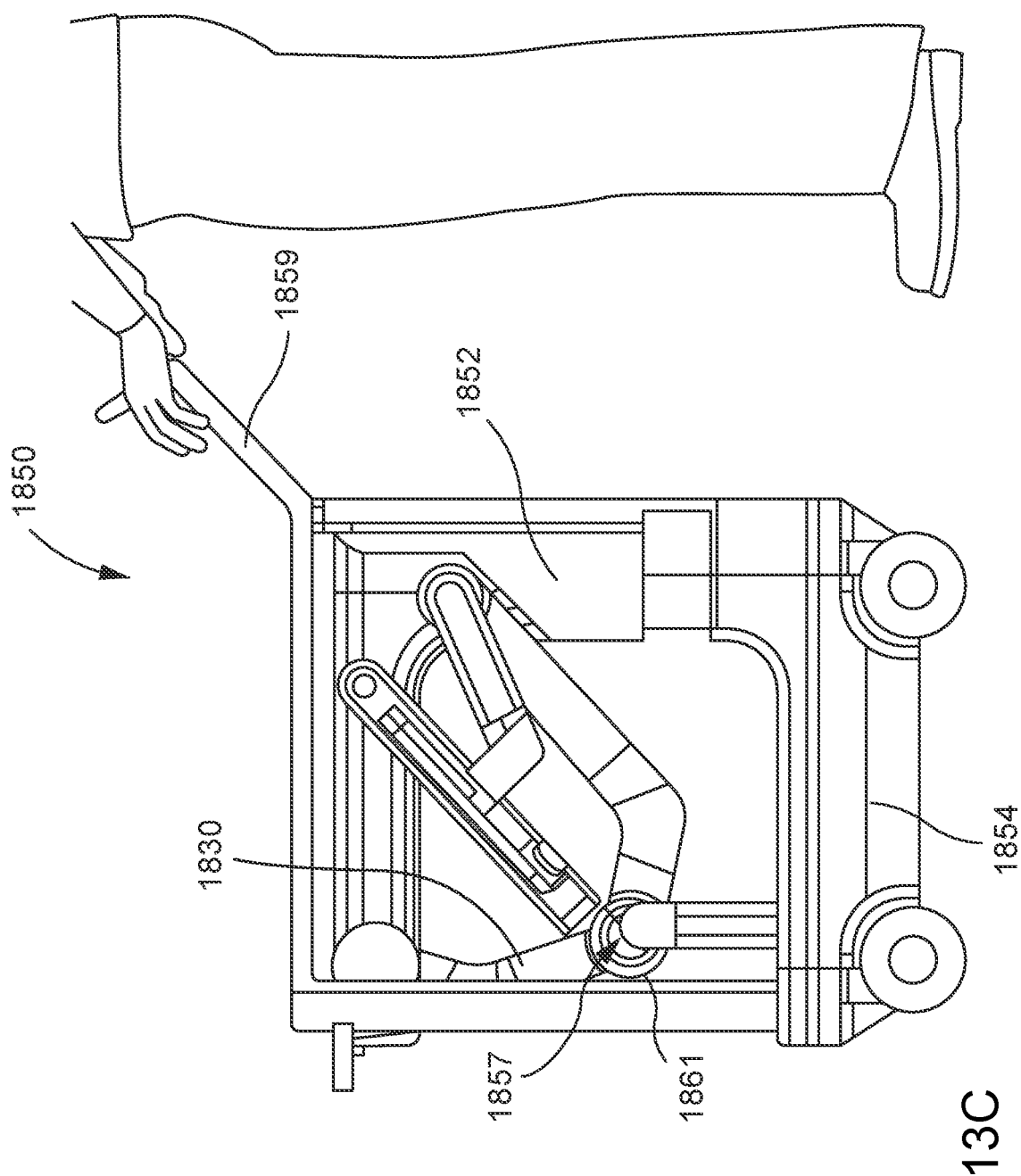
Figure 13D:
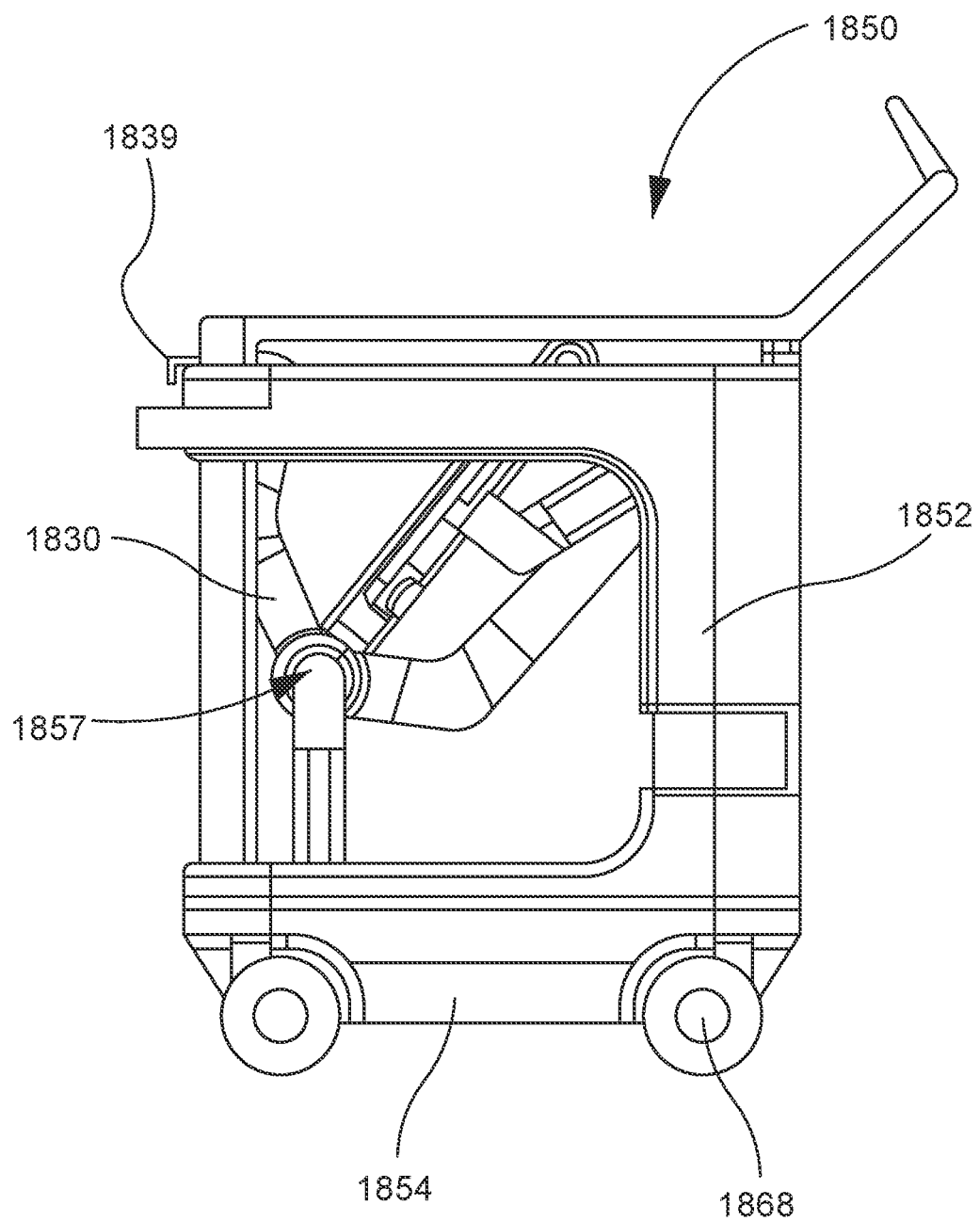
Figure 13E:
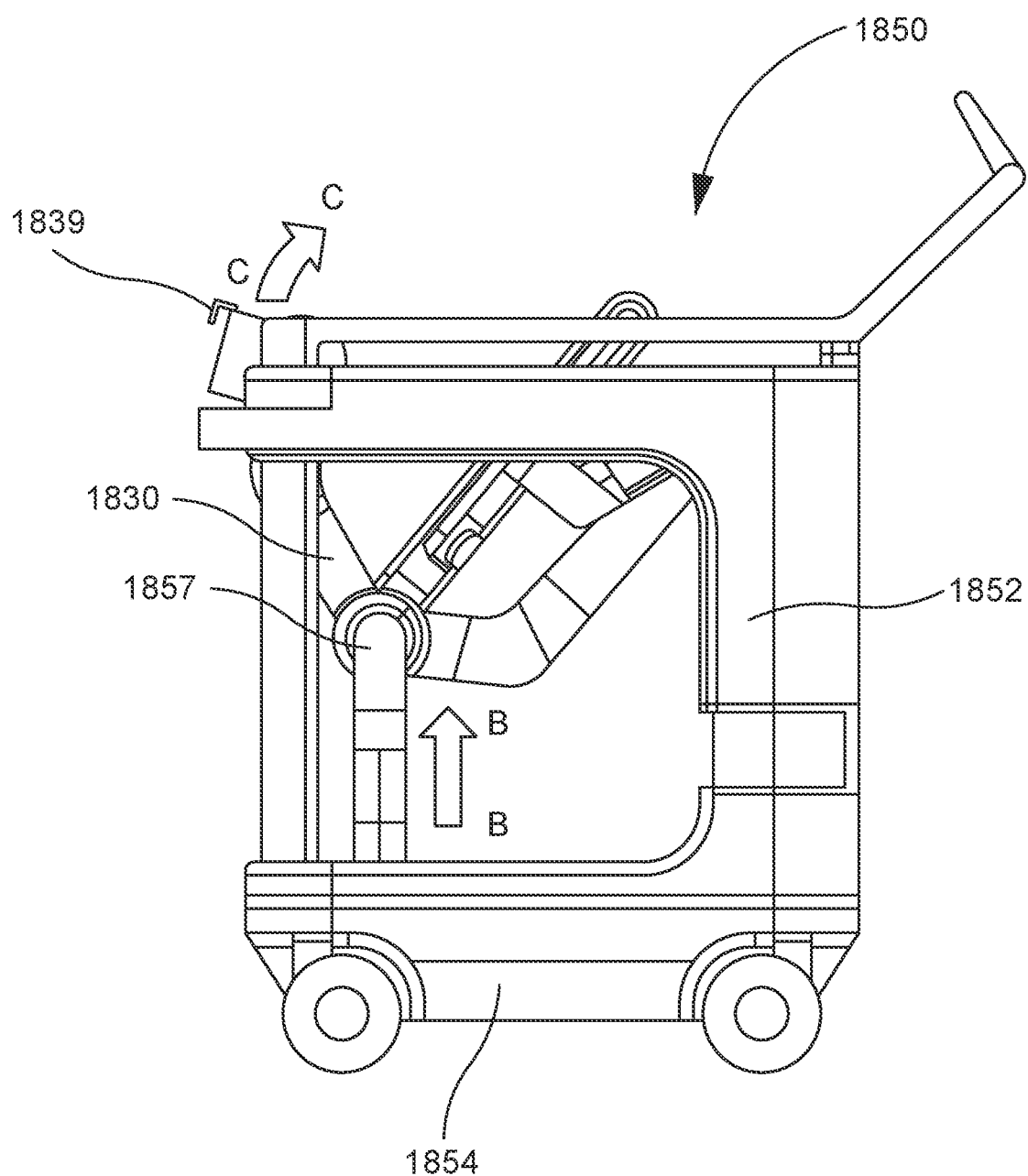
Figure 13F:
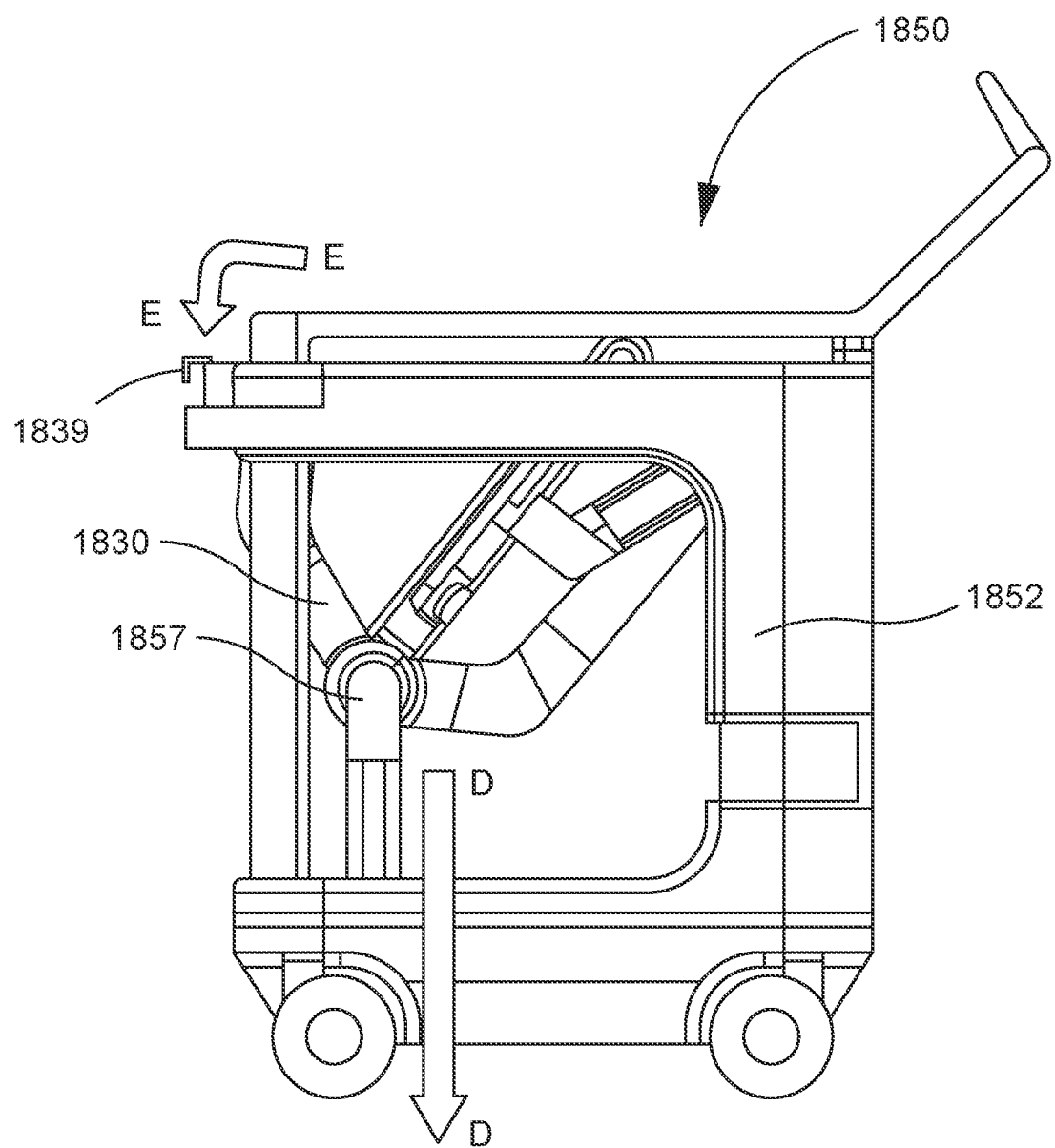

As shown in FIG. 13C, which is a side view of the arm cart 1850 in a stowed configuration, the arm cart 1850 can include a cradle 1857 (also referred to as an "arm support") to support the robotic arm 1830. Additionally, the arm cart 1850 can include a handle 1859 for engagement by the operator and easier maneuvering of the arm cart 1850. The cradle 1857 can be configured to releasably engage with and/or support a joint of the robotic arm 1830. The cradle 1857 can be coupled to the robotic arm 1830 at a support location 1881 on the robotic arm 1830, and the support location 1861 can be spaced from the coupling member 1839 of the robotic arm 1830. The cradle 1857 can be translatable in the Z-direction to control the vertical position of the robotic arm 1830. For example, FIGS. 13D-13F show the arm cart 1850 in three stages of a coupling operation. As shown in FIG. 13D, the cradle 1857 supports the robotic arm 1830 at least partially within the arm container 1852 such that the robotic arm 1830 such that the robotic arm 1830 is protected by the arm container 1852 and can articulate as needed. In the stowed configuration, the entire robotic arm 1830 except the coupler 1839 can be substantially disposed or contained within the arm container 1852 and can be stored, protected, and transported via the arm cart 1850. During movement of the arm cart 1850 on the support surface, the arm container 1852 can protect the robotic arm 1830 from impact with objects.

As shown in FIG. 13E, the cradle 1857 can linearly move the robotic arm 1830 vertically along arrow B-B such that the arm coupling member 1839 is raised along the Z axis and rotated along arrow C-C. In some embodiments, the robotic arm 1830 can be moved along the Z axis such that the arm coupling member 1839 is aligned with, for example, a coupling member associated with a surgical table, such as a surgical table that is the same or similar in structure and/or function to any of the surgical tables described herein (e.g., the surgical table 100). In some embodiments, the arm coupling member 1839 can be raised high enough such that the arm coupling member 1830 overshoots a coupling member associated with a surgical table along the Z axis. By overshooting along the Z axis, the arm coupling member 1839 can still engage with a surgical table in the case of a mismatch between the height of the surgical table and the height of the arm cart 1850. For example, as shown in FIG. 13F, after the cradle 1857 has raised the robotic arm 1830 such that the arm coupling member 1839 is at the Z-axis position shown in FIG. 13E, the cradle 1857 can move downward along arrow D-D such that the arm coupling member 1839 of the robotic arm 1830 is lowered with respect to the arm cart 1850 and travels along arrow E-E. In such a position, if the arm cart 1850 is aligned with a coupling member of a surgical table with respect to the X axis and the Y axis, the arm coupling member 1839 may engage with the coupling member associated with the surgical table. In some embodiments, the robotic arm 1830 can articulate before the cradle 1857 moves downward such that the robotic arm 1830 is closer to the surgical table along the X axis to effectively latch with the coupling member of the surgical table. In some embodiments, the distance along the Z axis that the arm coupling member 1839 may move can be, for example, 6 inches or more.

Although the arm cart 1850 is described as storing, deploying, and transferring only one robotic arm 1830, in some embodiments the arm cart 1850 can store, deploy, and transfer a second robotic arm similarly as described above with respect to the robotic arm 1830. For example, both the robotic arm 1830 and a second robotic arm can be loaded onto the arm cart 1850 prior to transfer of either robotic arm to a surgical table. The arm cart 1850 can include a second arm support and the second robotic arm can be loaded into engagement with the second arm support. After transferring the robotic arm 1830 to a first coupling site of a surgical table as described above, the arm cart 1850 can be moved, with the second robotic arm in a stowed configuration, via the base 1854 to another location near the surgical table. The second arm support can then move the second robotic arm similarly as described above from the stowed configuration to the deployed configuration such that an arm coupling member of the second robotic arm can be disposed in a proper position for engagement with a second mating coupling member associated with the surgical table. Once in the docking configuration and properly aligned with a coupling site of a surgical table, the second robotic arm can be transferred to the surgical table and the arm cart 1850 can be moved away from the surgical table.

Figure 14A:
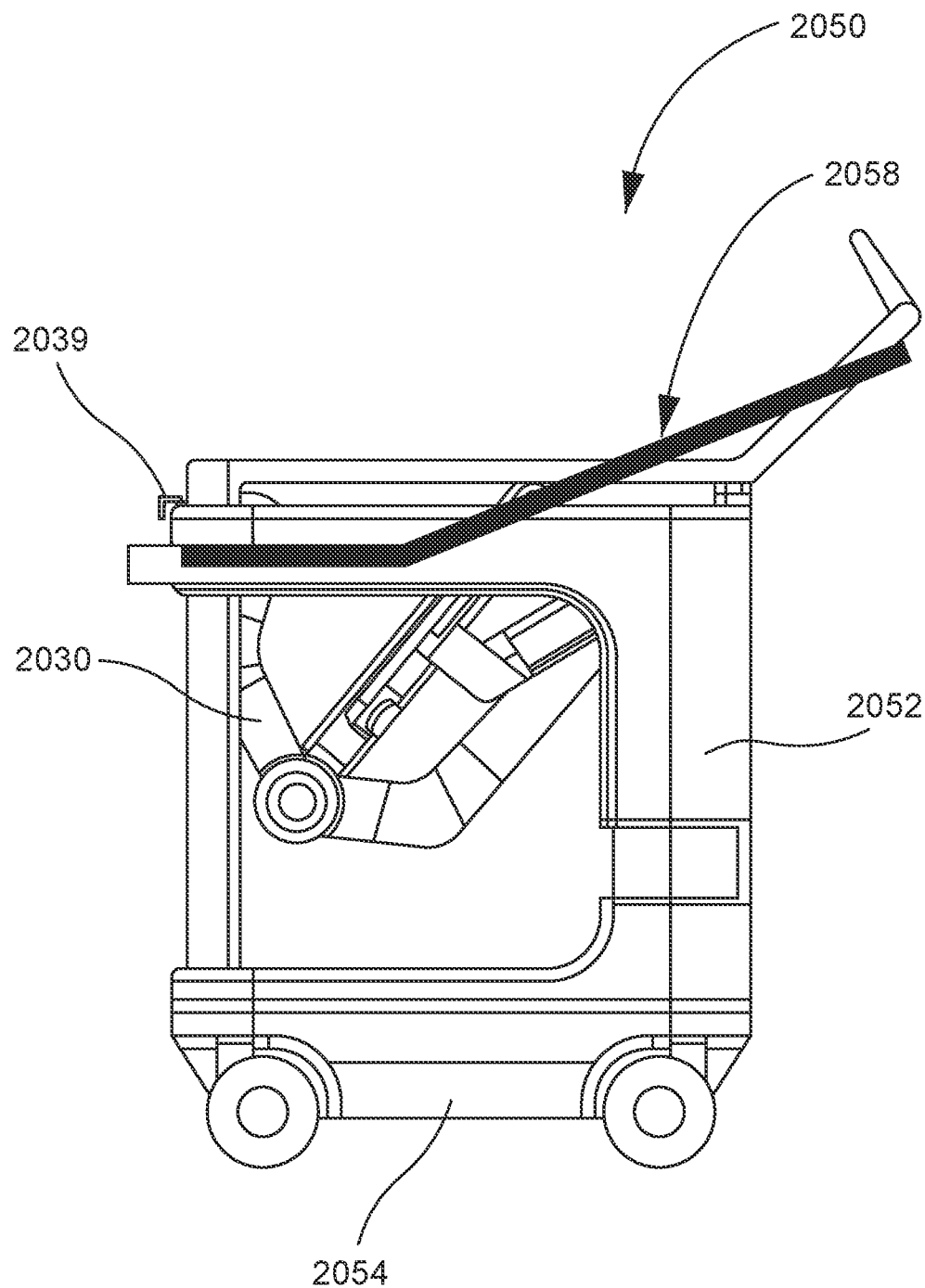
FIGS. 14A-14C show side views of an arm cart in three configurations during a docking operation.
Figure 14B:
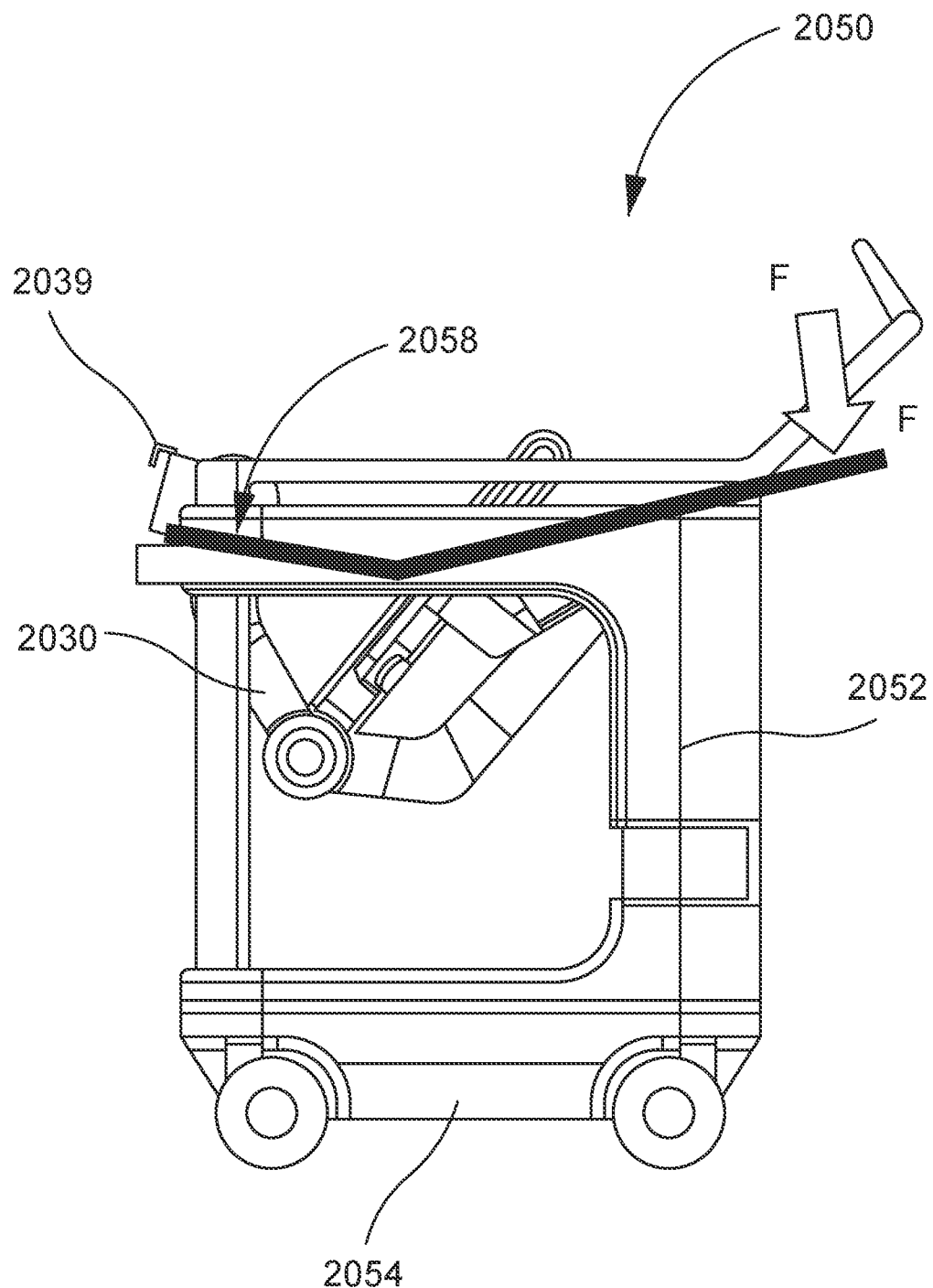
Figure 14C:
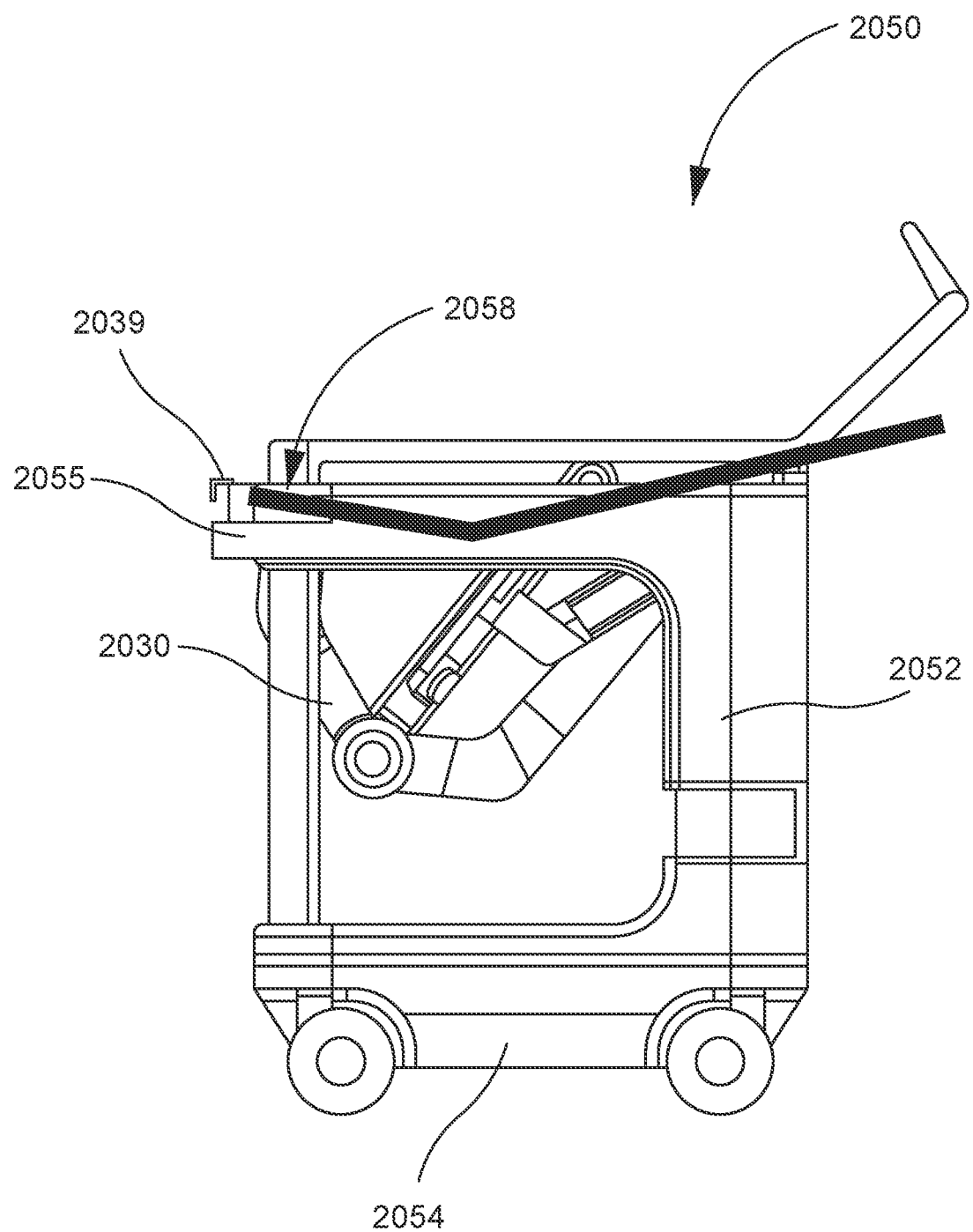

FIGS. 14A-14C show side views of an arm cart 2050 in three configurations during a coupling operation. The arm cart 2050 can be the same or similar in structure and/or function to any of the arm carts described herein. For example, the arm cart 2050 can include an arm container 2052 and a base 2054. The arm container 2052 is configured to support, protect, and promote sterility for a robotic arm 2030 during transportation of the robotic arm 2030, for example, from a storage area to the operating area, and during transfer of the robotic arm 2030 from the arm cart 2050 to a surgical table for use during the surgical procedure. The arm container 2052 can be coupled to the base 2054 and releasably couplable to the robotic arm 2030 above the base. The base 2054 can be freely moveable on a support surface, such as, for example, a floor, between a first location remote from a surgical table and a second location adjacent to the surgical table. For example, the base 1854 can be coupled to a number of wheels 1868, such as, for example, three or four wheels, such that the arm cart 1850 is moveably supported on the support surface. The robotic arm 2030 includes an arm coupling member 2039 (also referred to as a "coupler"). The base 2054 and the arm container 2052 can permit and/or control movement of the robotic arm 2030 along and/or about the X, Y, and/or Z axes. When the base 2054 is at the second location adjacent to the surgical table, the arm container 2052 can permit movement of the robotic arm 2030 between a first position in which the arm coupling member 2039 is not engageable with a coupling site of the surgical table and a second position in which the arm coupling member 2039 is engageable with the coupling site of the surgical table.

Unlike the arm cart 1850 described above with reference to FIGS. 13A-13F, the arm cart 2050 does not include a cradle for translating the robotic arm 2030 in the Z direction (i.e., vertically). Rather, the arm cart 2050 includes a lever 2058 (also referred to as an "arm support") configured to control the position of the arm coupling member 2039 of the robotic arm 2030. The lever 2058 can be actuated through any suitable actuation means. For example, the lever 2058 can be user-actuated. The lever 2058 can be used to lift the arm coupling member 2039 and lower the arm coupling member 2039 into engagement with, for example, a coupling member associated with a surgical table (not shown) (e.g., a rail). The lever 2058 can include a four bar link or an over center mechanism such that the lever 2058 can move the arm coupling member 2039 through a high arc for greater flexibility along the Z axis. The arm cart 2050 can be configured to support the robotic arm 2030 in the first, stowed position when the robotic arm 2030 has a center of gravity disposed below the lever 2058. Similarly, the arm cart 1850 can be configured to support the robotic arm 2030 in the second, deployed position when the robotic arm 2030 also has a center of gravity disposed below the lever 2058.

In use, as shown in FIG. 14A, the robotic arm 2030 can be disposed at least partially within the arm container 2052. In the stowed configuration, the entire robotic arm 2030 except the coupler 2039 can be substantially disposed or contained within the arm container 2052 and can be stored, protected, and transported via the arm cart 2050. During movement of the arm cart 2050 on the support surface, the arm container 2052 can protect the robotic arm 2030 from impact with objects. The arm cart 2050 can be pushed into adjoining or abutting contact with, for example, a coupling member associated with a surgical table, such as a surgical table the same or similar to any of the surgical tables described herein (e.g., the surgical table 100). As shown in FIG. 14B, when the lever 2058 is pushed, such as along arrow F-F, the lever 2058 can rotationally move the robotic arm 2030 such that the arm coupling member 2039 vertically overshoots the coupling member associated with the surgical table along the Z axis. By overshooting along the Z axis, the arm coupling member 2039 can still engage with the coupling member of the surgical table in the case of a mismatch between the height of the surgical table and the height of the arm cart 2050. For example, as shown in FIG. 14C, after the lever 2058 has lifted the robotic arm 2030 such that the arm coupling member 2039 is at the Z-axis position shown in FIG. 14B, the lever 2058 can lower the arm coupling member 2039 such that the arm coupling member 2039 of the robotic arm 2030 is lowered with respect to the arm cart 2050. In such a position, if the arm cart 1050 is aligned with a coupling member of a surgical table with respect to the X axis and Y axis, the arm coupling member 2039 may engage with the coupling member associated with the surgical table. In some embodiments, the robotic arm 2030 can articulate before the lever 2058 lowers the robotic arm 2030 such that the robotic arm 2030 is closer to the surgical table in the X-direction to effectively latch with the coupling member of the surgical table. In some embodiments, the distance along the Z-axis that the arm coupling member 2030 may move can be, for example, 6 inches or more.

Although the arm cart 2050 is described as storing, deploying, and transferring only one robotic arm 2030, in some embodiments the arm cart 2050 can store, deploy, and transfer a second robotic arm similarly as described above with respect to the robotic arm 2030. For example, both the robotic arm 2030 and a second robotic arm can be loaded onto the arm cart 2050 prior to transfer of either robotic arm to a surgical table. The arm cart 2050 can include a second arm support and the second robotic arm can be loaded into engagement with the second arm support. After transferring the robotic arm 2030 to a first coupling site of a surgical table as described above, the arm cart 2050 can be moved, with the second robotic arm in a stowed configuration, via the base 2054 to another location near the surgical table. The second arm support can then move the second robotic arm similarly as described above from the stowed configuration to the deployed configuration such that an arm coupling member of the second robotic arm can be disposed in a proper position for engagement with a second mating coupling member associated with the surgical table. Once in the docking configuration and properly aligned with a coupling site of a surgical table, the second robotic arm can be transferred to the surgical table and the arm cart 2050 can be moved away from the surgical table.

In some embodiments, an arm cart can be coupled to a robotic arm via spring-loaded cart arms. For example, FIG. 15A is a schematic illustration of a cross-sectional front view of an arm cart 2150 and a robotic arm 2130 in an uncoupled configuration. The arm cart 2150 can be the same or similar in structure and/or function to any of the arm carts described herein. For example, the arm cart 2150 can include an arm container (not shown) and a base (not shown). The arm cart 2150 can include a first cart arm 2156A and a second cart arm 2156B coupled to the arm container and/or base via a first spring-loaded coupling mechanism 2155A and a second spring-loaded coupling mechanism 2155B. Thus, the first cart arm 2156A and the second cart arm 2156B are spring-biased along arrows G-G and G'-G', respectively. The first cart arm 2156A and the second cart arm 2156B can include a first engagement feature 2151A and a second engagement feature 2151B, respectively.

The robotic arm 2130 can include a target joint $J1_{2130}$ disposed at or near a mounting end of the robotic arm 2130. The target joint $J1_{2130}$ can include a first detent 2133A and a second detent 2133B for engagement with the engagement feature 2151A of the first cart arm 2156A and the second engagement feature 2151B of the second cart arm 2156B, respectively. For example, FIG. 15B is a schematic side view of the robotic arm 2130. As shown in FIG. 15B, the target joint $J1_{2130}$ includes the detent 2133A. The detent 2133A can be shaped and sized for engagement with the engagement feature 2151A of the first cart arm 2156A. In some embodiments, the detents 2133A and 2133B and the engagement features 2151A and 2151B can be shaped and sized such that, upon engagement of the detent 2133A with the engagement feature 2151A and the detent 2133B with the engagement feature 2151B, the cart arms 2156A and 2156B can control the location and rotational position of the target joint $J1_{2130}$.

In use, as shown in FIG. 15A, the arm cart 2150 and/or the robotic arm 2130 can be moved into proximity with each other such that the cart arms 2156A and 2156B can move into engagement with the robotic arm 2130. The cart arms 2156A and 2156B can then be moved along arrows G-G and G'-G', respectively, via the spring-loaded coupling mechanisms 2155A and 2155B. As shown in FIG. 15C, which is a cross-sectional front view of the arm cart 2150 in a coupled configuration with the robotic arm 2130, the engagement features 2151A and 2151B can lockingly engage with the detents 2133A and 2133B of the robotic arm 2130. Upon locking engagement, the arm cart 2150 can rotate the robotic arm 2130 via the cart arms 2156A and 2156B as shown by arrow H-H into a storage position or a deployment position. In some embodiments, after moving the robotic arm 2130 into a storage or deployment position, the cart arms 2156A and 2156B can decouple from the robotic arm 2130 and can engage another robotic arm for storage and/or deployment of the other robotic arm. While the cart arms 2156A and 2156B are described as coupling with the target joint $J1_{2130}$, in some embodiments the cart arms 2156A and 2156B can be configured to engage a different structure associated with the robotic arm 2130.

Although not shown in FIGS. 15A-15C, the robotic arm 2130 can include a table coupling mechanism configured to releasably couple to a coupling site on a surgical table. The table coupling mechanism can have a first latching configuration with a first release force and a second latching configuration with a second release force greater than the first release force. For example, in some embodiments, the table coupling mechanism can be in the first latching configuration when the table coupling mechanism has been inserted into engagement with a mating coupling mechanism on a surgical table, but the table coupling mechanism can be pulled out of engagement if the arm cart 2150 moves away from the surgical table, pulling the robotic arm 2130. The table coupling mechanism can be in the second latching configuration if an additional latching element locks the table coupling mechanism to the table coupling mechanism such that if the arm cart 2150 moves away from the surgical table, the robotic arm 2130 remains coupled to the surgical table. Additionally, in some embodiments, the force required to dislodge the engagement features 2151A and 2151B from engagement with the detents 2133A and 2133B can be greater than the first release force and less than the second release force. Thus, if the table coupling mechanism is in the first latching configuration, the robotic arm 2130 will not be separated from the arm cart 2150 if the arm cart 2150 is pulled away from the surgical table. If the table coupling mechanism is in the second latching configuration, however, the robotic arm 2130 will be separated from the arm cart 2150 and remain coupled to the surgical table upon movement of the arm cart 2150 away from the surgical table.

Figure 16:
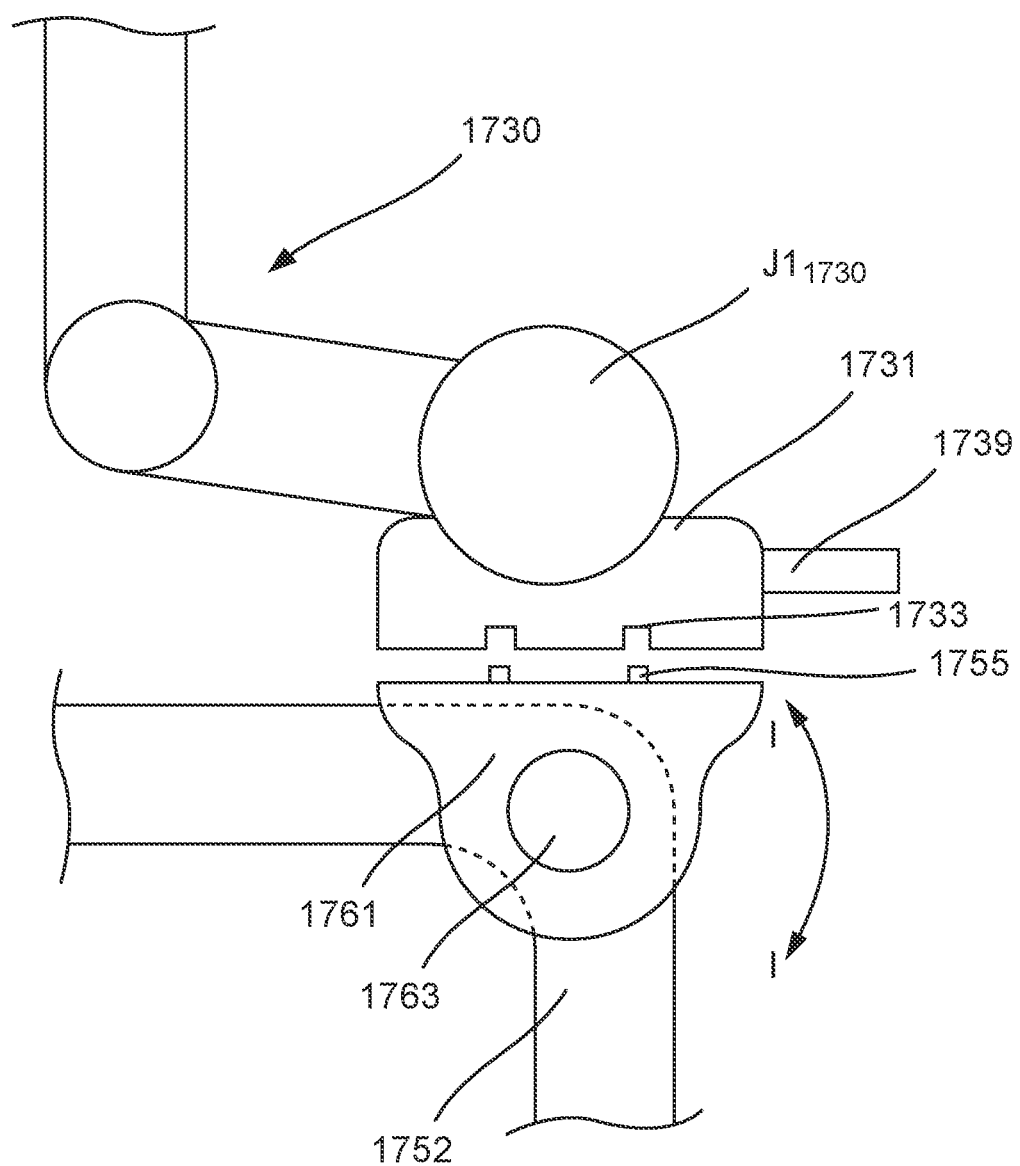
FIG. 16 is a schematic illustration of a coupling mechanism of an arm container and a robotic arm, according to an embodiment.

FIG. 16 is a schematic illustration of a coupling mechanism rotationally coupled to an arm container and configured to releasably lock to a robotic arm. FIG. 16 is a schematic illustration of a robotic arm 1730 and a coupling mechanism 1761 rotationally coupled to an arm container 1752. As shown in FIG. 16, the coupling mechanism 1761 is rotationally coupled to the arm container 1752 via a pivot joint 1763. The arm container 1752 can be the same or similar in structure and/or function to any of the arm containers described herein. The coupling mechanism 1761 includes engagement features 1755 and is configured to rotate along arrow I-I. The robotic arm 1730 includes a target joint $J1_{1730}$ and a coupling mechanism 1731. An arm coupling member 1739 is attached to the coupling mechanism 1731. The arm coupling member 1739 can be configured for attachment of the robotic arm 1730 to a surgical table (not shown). The coupling mechanism 1731 of the robotic arm 1730 can include engagement features 1733. The engagement features 1733 can be shaped and sized for engagement with the engagement features 1755 of the coupling mechanism 1761 of the arm container 1752.

In use, the coupling mechanism 1761 coupled to the arm container 1752 can be lockingly engaged with the coupling mechanism 1731 of the robotic arm 1730 via the engagement features 1755 and the engagement features 1733. When the coupling mechanism 1761 and the coupling mechanism 1731 are lockingly engaged, the coupling mechanism 1761 can be rotated, such as along arrow I-I, such that the robotic arm 1730 is also rotated. Thus, the arm container 1752 can control the location and rotational position of the robotic arm for storage and/or deployment. In some embodiments, the latching and rotating of the coupling mechanism 1761 and the coupling mechanism 1731 can be controlled by the user via, for example, a lever or button.

Figure 17:
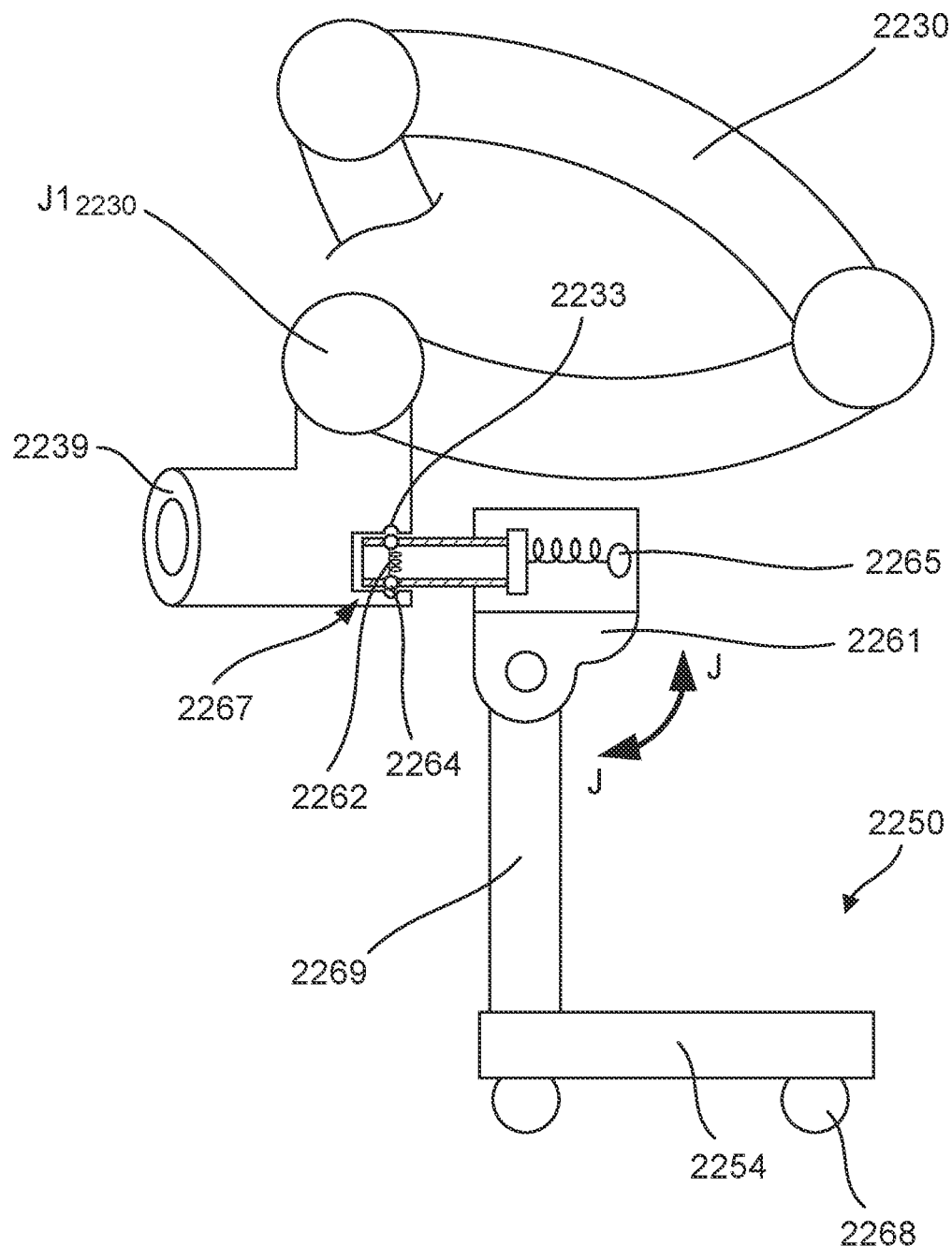
FIG. 17 is a schematic illustration of an arm cart engaged with a robotic arm in a deployment configuration, according to an embodiment.

FIG. 17 is a schematic illustration of an arm cart 2250 engaged with a robotic arm 2230. The arm cart 2250 can be the same or similar in structure and/or function to any of the arm carts described herein. For example, the arm cart 2250 can include an arm support 2269 and a base 2254. The base 2254 can be freely moveable on a support surface, such as, for example, a floor, between a first location remote from a surgical table and a second location adjacent to the surgical table. For example, the base 2254 can be coupled to a number of wheels 2268, such as, for example, three or four wheels, such that the arm cart 2250 is moveably supported on the support surface. A docking assembly 2265 can be coupled to the arm support 2269 via a cradle 2261. The cradle 2261 can rotate relative to the arm support 2269 such that the docking assembly 2265 rotates along arrow J-J. The rotation of the cradle 2261 can be assisted by mechanical means such as springs, shocks, pressure cylinders, and/or a motor. The docking assembly 2265 can include a docking pin 2267. The docking pin 2267 can include a spring 2262 and two or more balls 2264.

The robotic arm 2230 can be the same or similar in structure and/or function to any of the robotic arms described herein. For example, the robotic arm 2230 can include a target joint $J1_{2230}$ and an arm coupling member 2239 (also referred to as a "coupler"). The arm coupling member 2239 can include an engagement feature 2233 configured for engagement with the docking pin 2267. The engagement feature 2233 can be shaped, for example, as a cylindrical space with detents having a shape complementary to the balls 2264 of the docking pin 2267.

In use, the robotic arm 2230 can be coupled to the arm cart 2250 via the docking assembly 2265. The docking pin 2267 of the docking assembly 2265 can be inserted into the engagement feature 2233 of the arm coupling member 2239 until the spring 2263 pushes the balls 2264 outwardly into releasable engagement with the detents 2233 such that the robotic arm 2230 and the arm cart 2250 are in a coupled configuration, as shown in FIG. 17. When in the coupled configuration, the robotic arm 2230 can be rotated between a stored and deployed position via the cradle 2261 along arrow J-J. When in the stored position, the arm cart 2250 can be moved from the first location remote from the surgical table to the second location adjacent the surgical table. The robotic arm 2230 can then be rotated via the cradle 2261 along arrow J-J such that the arm coupling member 2239 is engageable with a coupling site of the surgical table. The robotic arm 2230 can then be engaged with the surgical table via the arm coupling member 2239. To release the robotic arm 2230 from the arm cart 2250, a pulling force can be applied to the docking pin 2267 sufficient to overcome the force of the spring 2262 holding the balls 2264 in the detents of the engagement feature 2233 and to withdraw the docking pin 2267 from the engagement feature 2233. The arm cart 2250 can then be moved away from the robotic arm 2230 and the surgical table.

Figure 18:
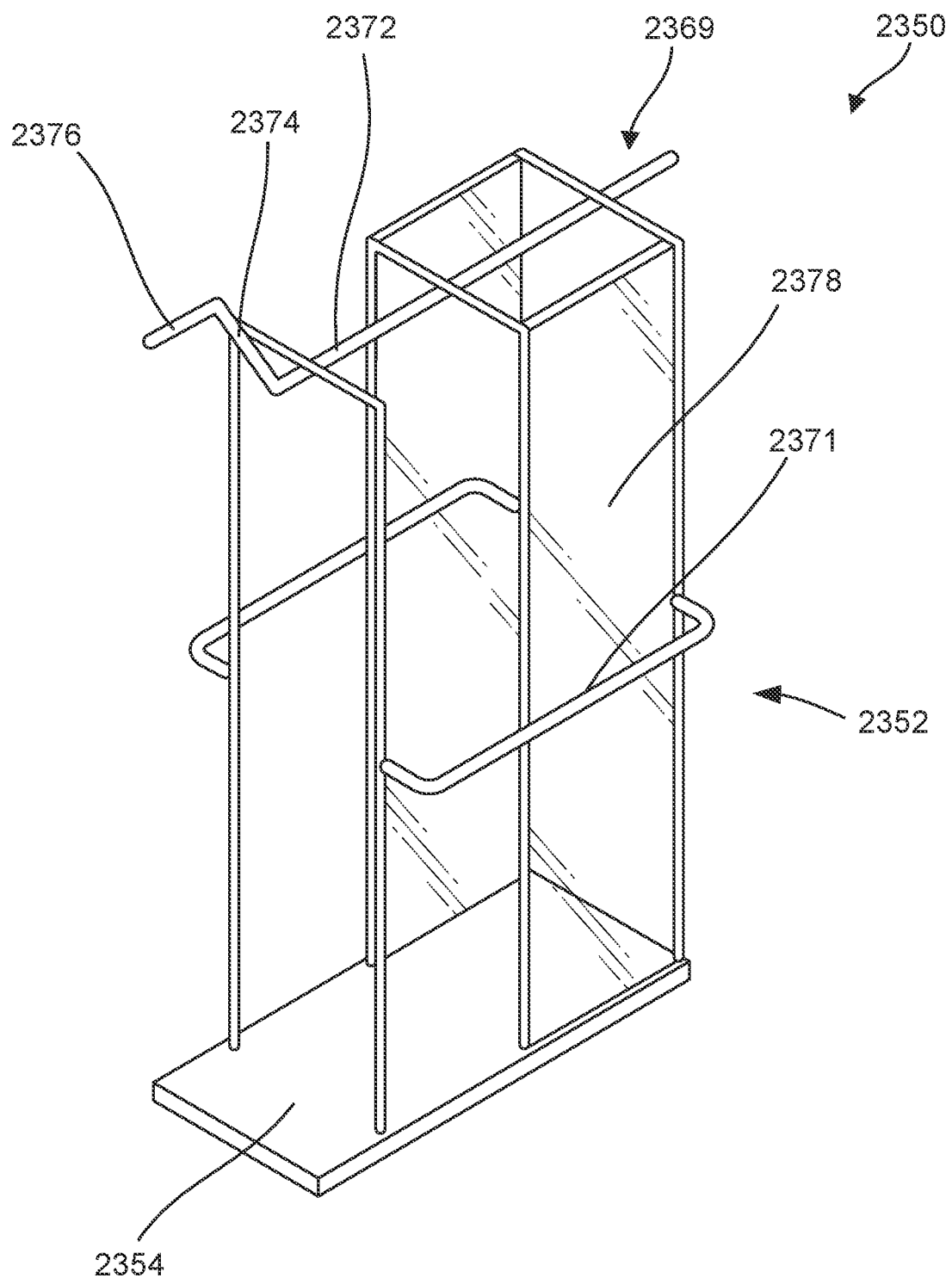
FIG. 18 is a schematic perspective view of an arm cart, according to an embodiment.

In some embodiments, a robotic arm can be suspended from a rail on an arm cart such that the arm cart supports the weight of the robotic arm and the mounting end of the robotic arm can be manually manipulated by a user into engagement with, for example, a surgical table without the user having to support the entire weight of the robotic arm. For example, FIG. 18 is a schematic perspective view of an arm cart 2350. The arm cart 2350 can include an arm container 2352 and a base 2354. The base 2354 can be freely moveable on a support surface, such as, for example, a floor, between a first location remote from a surgical table and a second location adjacent to the surgical table. For example, the base 2354 can be coupled to a number of wheels (not shown), such as, for example, three or four wheels, such that the arm cart 2350 is moveably supported on the support surface.

The arm cart 2350 can include an arm support 2369. The arm support 2369 can be coupled to the base 2354 and can be releasably coupleable to a robotic arm (not shown) to support the robotic arm above the base 2354 and, when the base 2354 is positioned at the second location adjacent to the surgical table, permit movement of the arm between a first position in which a coupler of the robotic arm is not engageable with a coupling site of the surgical table and a second position in which the coupler is engageable with the coupling site. The arm cart 2350 is configured to support the robotic arm in both the first position and second position, the center of gravity of the robotic arm being disposed below the arm support 2369 when the arm is in both the first position and the second position.

More specifically, the arm support 2369 can include an elongate robotic arm rail 2372. A robotic arm can be suspended from the robotic arm rail 2372 at a support location of the robotic arm spaced from a mounting end or coupler of the robotic arm. The robotic arm can be slid along the robotic arm rail 2372 such that the mounting end or coupler of the robotic arm can hang below the support location of the robotic arm and the user can manipulate the mounting end or coupler of the robotic arm relative to the surgical table. Additionally, in some embodiments, the robotic arm rail 2372 is coupled to an upper robotic arm rail 2376 via a ramp 2374. Thus, a robotic arm can be slid from the robotic arm rail 2372, up the ramp 2374, and along the upper robotic arm rail such that the robotic arm is position at a higher location along the Z axis and may be easier to couple with, for example, a surgical table.

The arm container 2352 can include one or more walls 2378 for protecting the robotic arm when the robotic arm is suspended from the robotic arm rail 2372. In some embodiments, the arm cart 2350 can be configured to support the robotic arm at least partially within the arm container 2352 when the arm is disposed in the first position to protect the robotic arm from impact with objects during movement of the arm cart 2352 on the support surface. In some embodiments, the arm cart 2350 can be configured to support the entire robotic arm except the coupler within the arm container 2352 when the arm is disposed in the first position. In some embodiments, the arm cart 2350 can be configured to support the arm such that the coupler is disposed within the arm container 2352 when the arm is disposed in the first position and such that the coupler is disposed outside the arm container 2352 when the arm is disposed in the second position. The arm container 2352 can also include one or more arm cart side rails 2371 to further protect any robotic arms suspended from the robotic arm rail 2372 and to allow for the user to push or pull the arm cart 2350 via the side rail 2371.

In use, the robotic arm can be suspended from the arm support 2369 and the arm cart 2352 can be moved from the first location remote from the surgical table to the second location adjacent to the surgical table. The robotic arm can then be slid along the arm support 2369 such that a coupler of the robotic arm is closer to the coupling site of the surgical table. The user can then maneuver (e.g., by hand) the coupler of the robotic arm such that the coupler is releasably coupled with the coupling site of the surgical table. Upon engagement, the weight of the robotic arm can be supported by the surgical table and the robotic arm can be disengaged from the arm support 2369. The arm cart 2352 can then be moved away from the surgical table and the robotic arm.

Although the arm cart 2350 is described as storing and transferring only one robotic arm 2330, in some embodiments the arm cart 2350 can store and transfer a second robotic arm similarly as described above. For example, both the robotic arm described above and a second robotic arm can be loaded onto the arm support 2369 prior to transfer of either robotic arm to the surgical table. After transferring one of the robotic arms to the coupling site of the surgical table as described above, the arm cart 2350 can be moved, with the second robotic arm in a stowed configuration, via the base 2354 to another location near the surgical table. The second robotic arm can be positioned for engagement with the surgical table similarly as described above. Once properly aligned with a second coupling site of the surgical table, the second robotic arm can be transferred to the surgical table and the arm cart 2350 can be moved away from the surgical table.

Figure 19A:
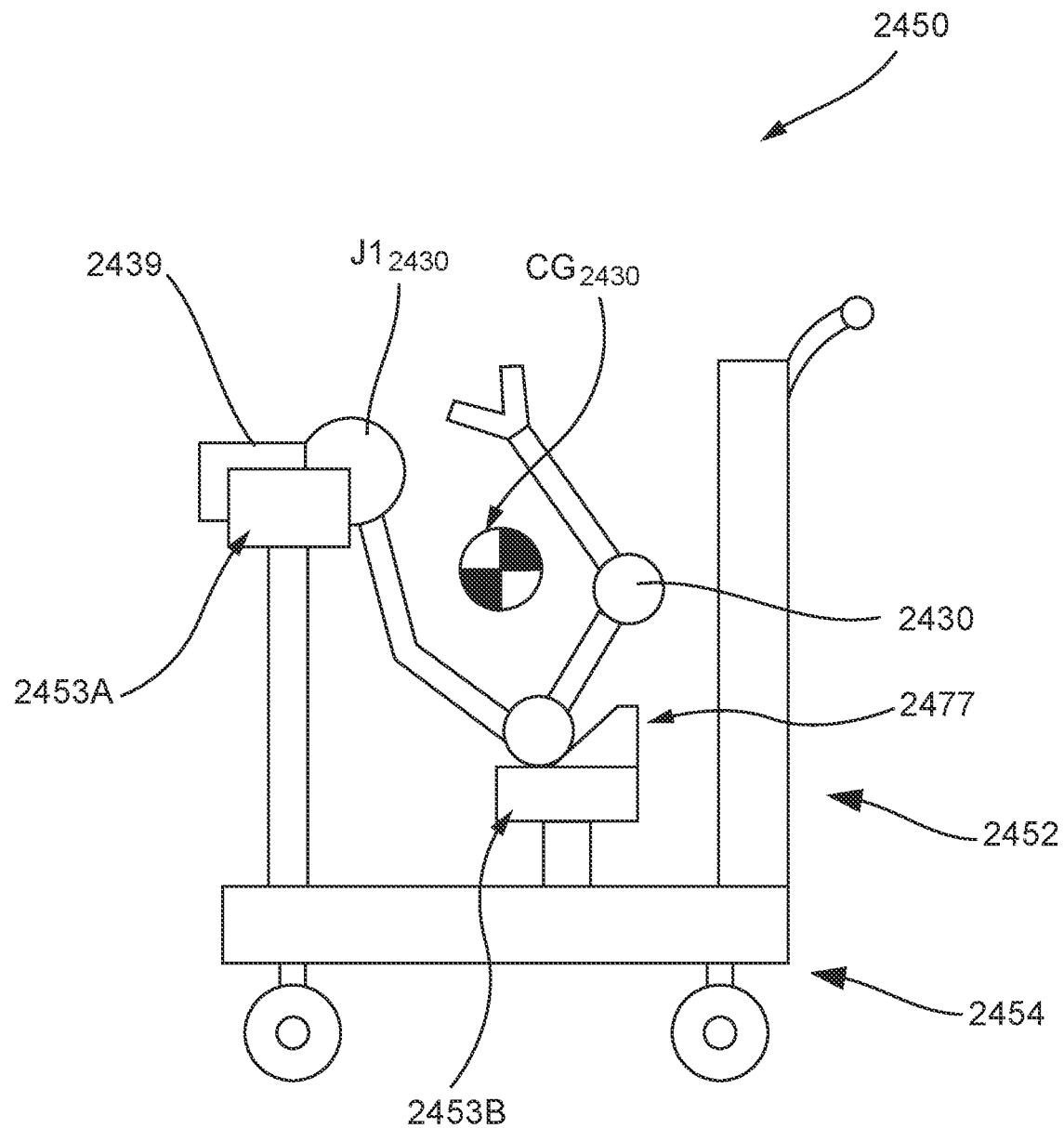
FIGS. 19A-19C are various views of an arm cart and robotic arm in multiple configurations, according to an embodiment.

FIG. 19A is a schematic illustration of a side view of an arm cart 2450 and a robotic arm 2430. The arm cart 2450 can be the same or similar in structure and/or function to any of the arm carts described herein. For example, the arm cart 2450 includes an arm container 2452 and a base 2454. The arm container 2452 can be coupled to and extend upwardly from the base 2454. The base 2454 can be freely moveable on a support surface, such as, for example, a floor, between a first location remote from a surgical table and a second location adjacent to the surgical table. The arm cart 2450 can also include a first arm cradle 2453A (also referred to as a "first arm support") and a second arm cradle 2453B (also referred to as a "second arm support"). The second arm cradle 2453B can include a back stop 2477.

The robotic arm 2430 can be the same or similar in structure and/or function to any of the robotic arms described herein. For example, the robotic arm 2430 can include an arm coupling member 2439 (also referred to as a "coupler"). The arm cart 2450 is configured to support the robotic arm 2430 such that the center of gravity $CG_{2430}$ of the robotic arm 2430 is disposed below the first arm cradle 2453A when the robotic arm 2430 is disposed in the first position. As shown in FIG. 19A, the first arm cradle 2453A and the second arm cradle 2453B can be positioned on opposite sides of the center of gravity $CG_{2430}$ of the robotic arm 2430 such that the bending moments needed to support the robotic arm 2430 are minimized. The robotic arm 2430 can be held in position on the first arm cradle 2453A and the second arm cradle 2453B by gravity. Thus, the first arm cradle 2453A and the second arm cradle 2453B can be stationary relative to the base 2454 and no latch is needed to maintain the robotic arm 2430 on the arm container 2452. In some embodiments, substantially the entire robotic arm 2430 except the arm coupling member 2439 can be disposed within the arm container 2452 and protected by the arm container 2452 from impact with objects during movement of the arm cart 2450 on the support surface.

Figure 19C:
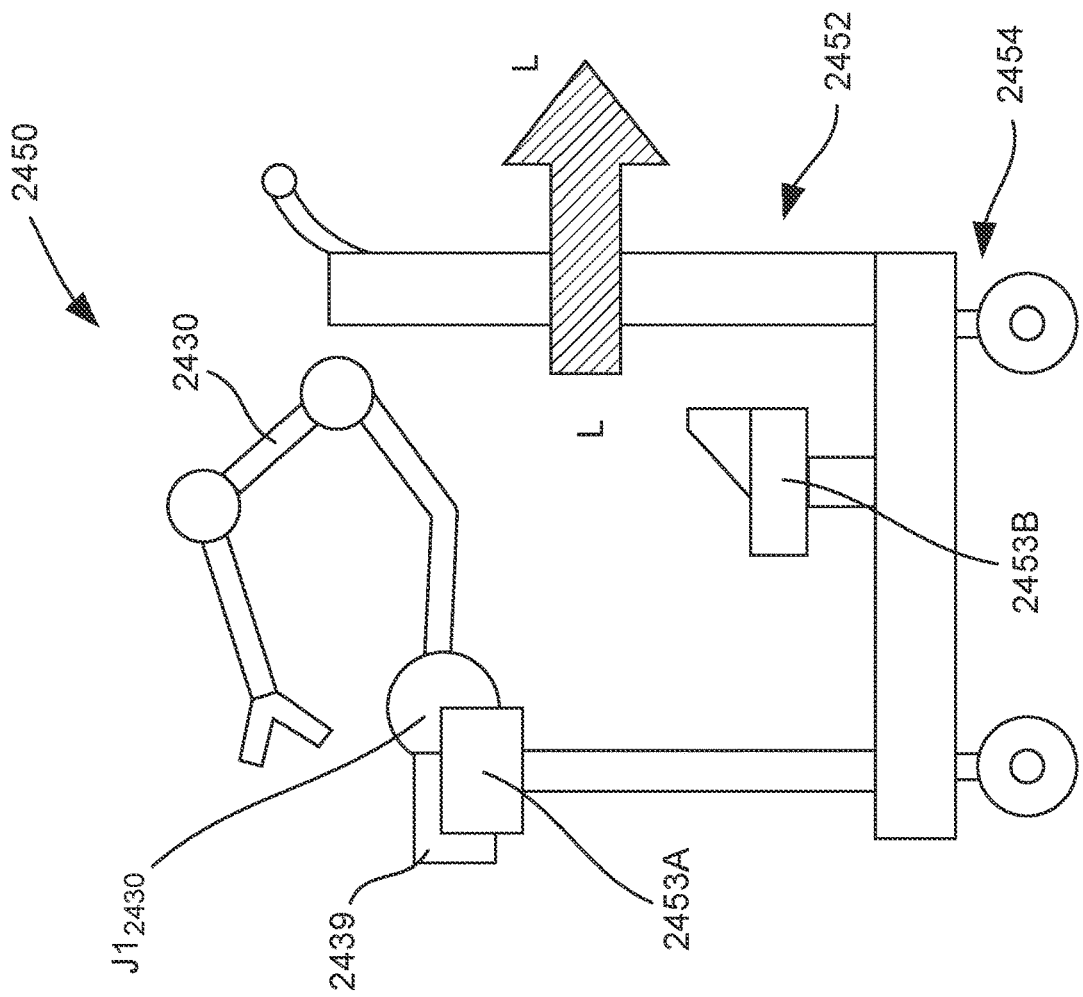
Figure 19B:
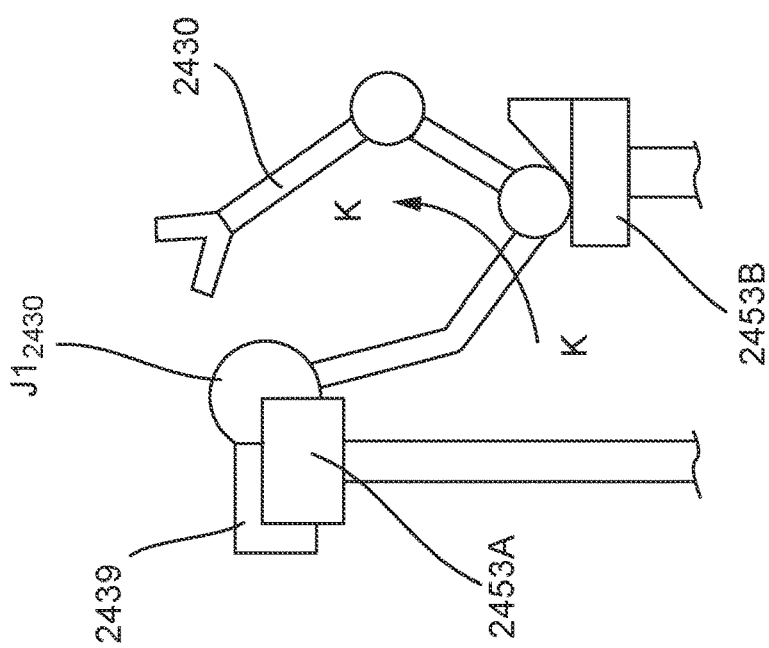

In use, as shown in FIG. 19B, after the arm coupling member 2439 is coupled to, for example, a surgical table, the robotic arm 2430 can pivot along arrow K-K up and out of the second arm cradle 2453B. In some embodiments, power can be provided from the surgical table to the robotic arm 2430 via the coupler 2439. The surgical arm 2430 can include at least one joint, such as joint $J1_{2430}$, separating a first portion of the robotic arm 2430 (e.g., the portion including coupler 2439) from a second portion of the robotic arm 2430. The joint $J1_{2430}$ can enable movement of the first portion of the robotic arm 2430 relative to the second portion of the arm using the power provided by the table. For example, after coupling the coupler 2439 of the robotic arm 2430 to a coupler associated with the surgical table, the second portion of the robotic arm can be caused to move about the joint $J1_{2430}$ such that the second portion of the robotic arm 2430 is moved away from the second arm support 2453B. In some embodiments, the power provided from the surgical table to the robotic arm 2430 can cause two or more portions of the robotic arm 2430 to rotate relative to two or more joints of the robotic arm 2430 away from the arm cart 2450. As shown in FIG. 19C, when the robotic arm 2430 has pivoted high enough such that the robotic arm 2430 does not obstruct movement of the arm cart 2450, the arm cart 2450 can be moved away from the robotic arm 2430, such as along arrow L-L.

Figure 20A:
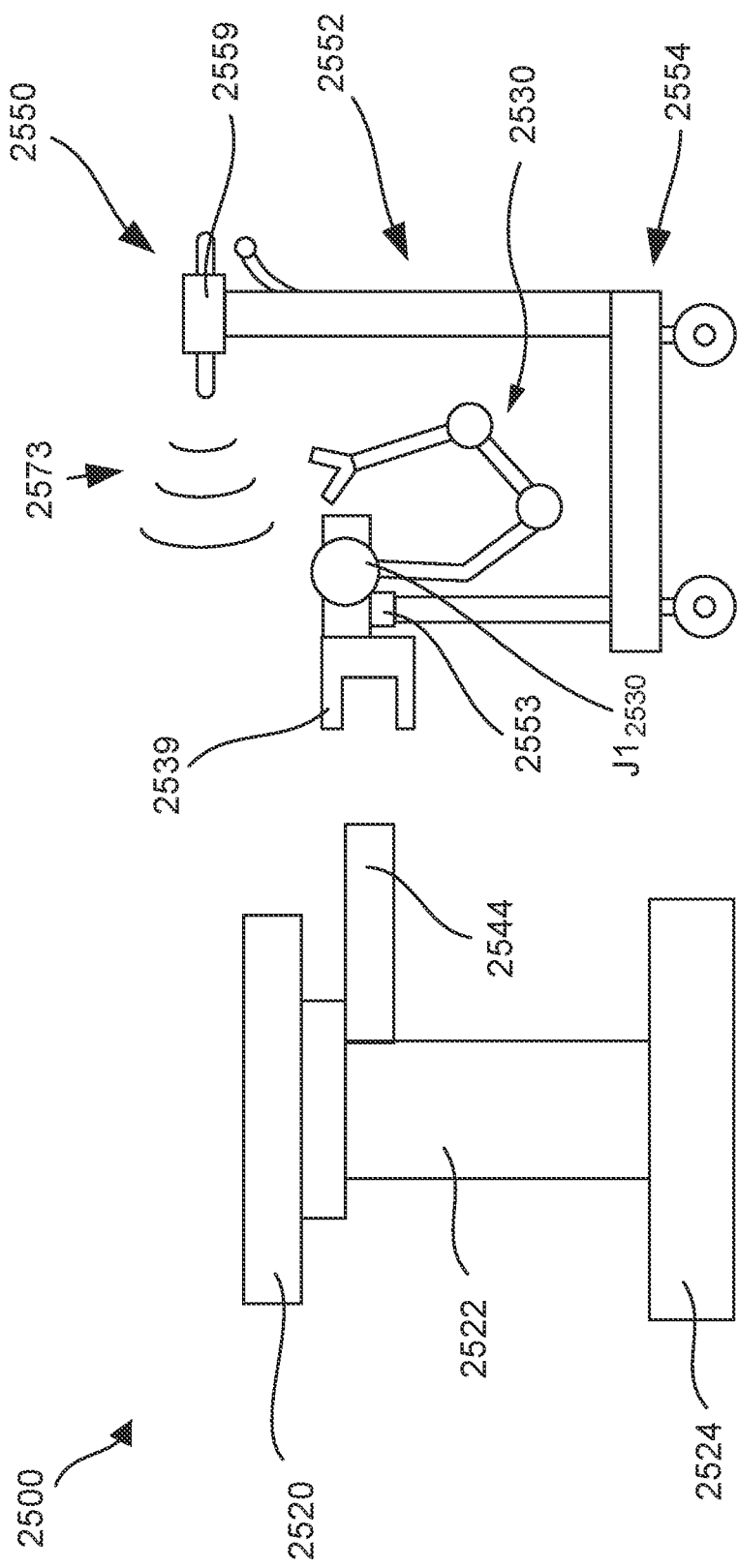
FIGS. 20A-20C are various views of an arm cart and robotic arm in multiple configurations, according to an embodiment.

In some embodiments, a wireless hand control on an arm cart can be used to activate movement of a robotic arm for transfer to a surgical table. For example, FIG. 20A is a schematic illustration of a surgical table 2500, an arm cart 2550, and a robotic arm 2530 in a first configuration. The surgical table 2500 can be the same or similar to any of the surgical tables described herein (e.g., the surgical table 100). For example, the surgical table 2500 includes a table top 2520, a support 2522, and a base 2524. A patient (not shown) can be disposed on the table top 2520. The surgical table 2500 can include a table coupling member 2544.

The arm cart 2550 can be the same or similar in structure and/or function to any of the arm carts described herein. For example, the arm cart 2550 can include an arm container 2552, an arm cradle 2453 (also referred to as an "arm support"), and a base 2554. The arm container 2552 can also include a handle 2559 including a wireless hand control 2573. The wireless hand control 2573 can include any suitable wireless communication components, such as, for example, infrared communication elements.

The robotic arm 2530 can be the same or similar in structure and/or function to any of the robotic arms described herein. For example, the robotic arm 2530 can include a coupling member 1039 and a target joint $J1_{2530}$. The coupling member 2539 of the robotic arm 2530 can be configured to releasably engage with the coupling member 2544 of the table 2500. Additionally, the coupling member 2539 and the coupling member 2544 can include any suitable complementary releasable coupling means.

Figure 20B:
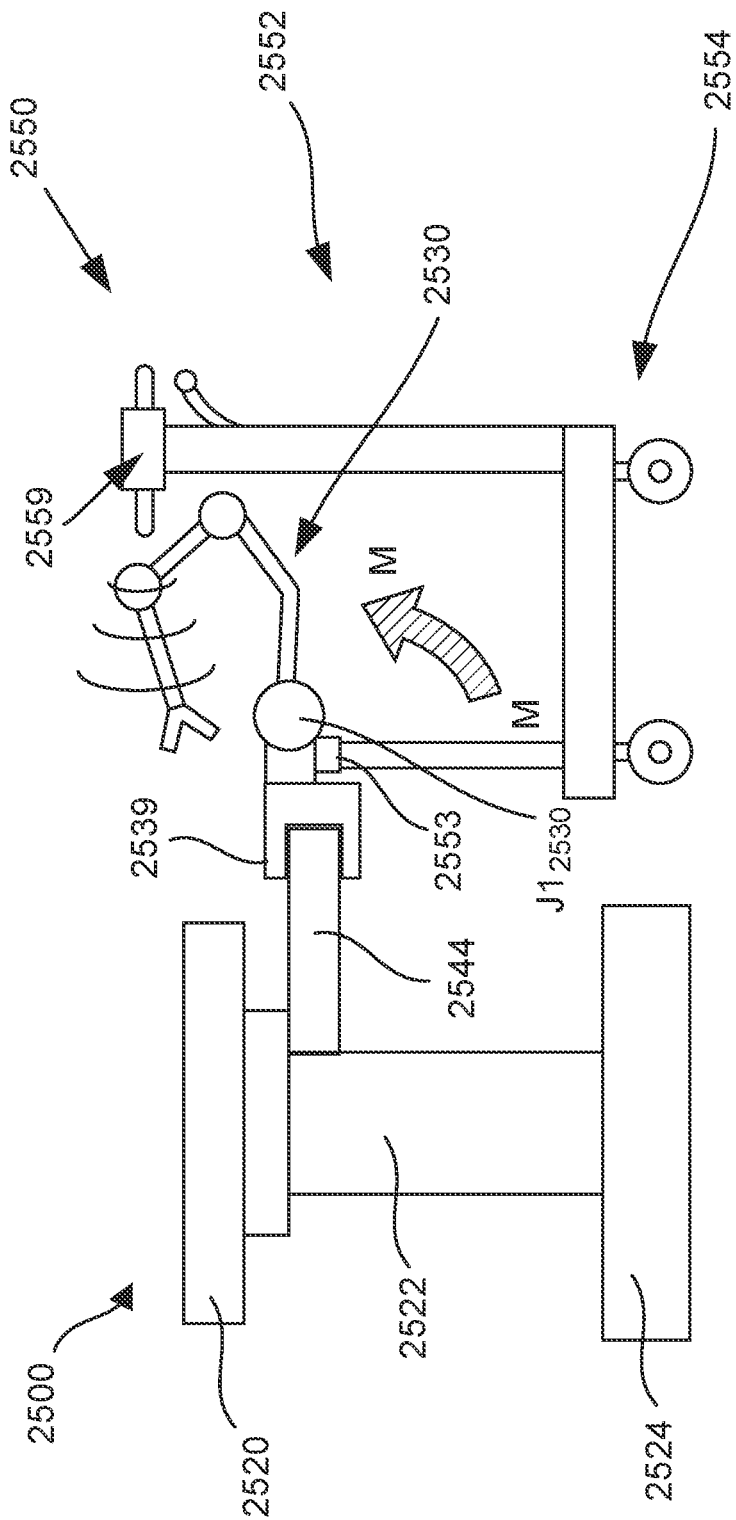
Figure 20C:
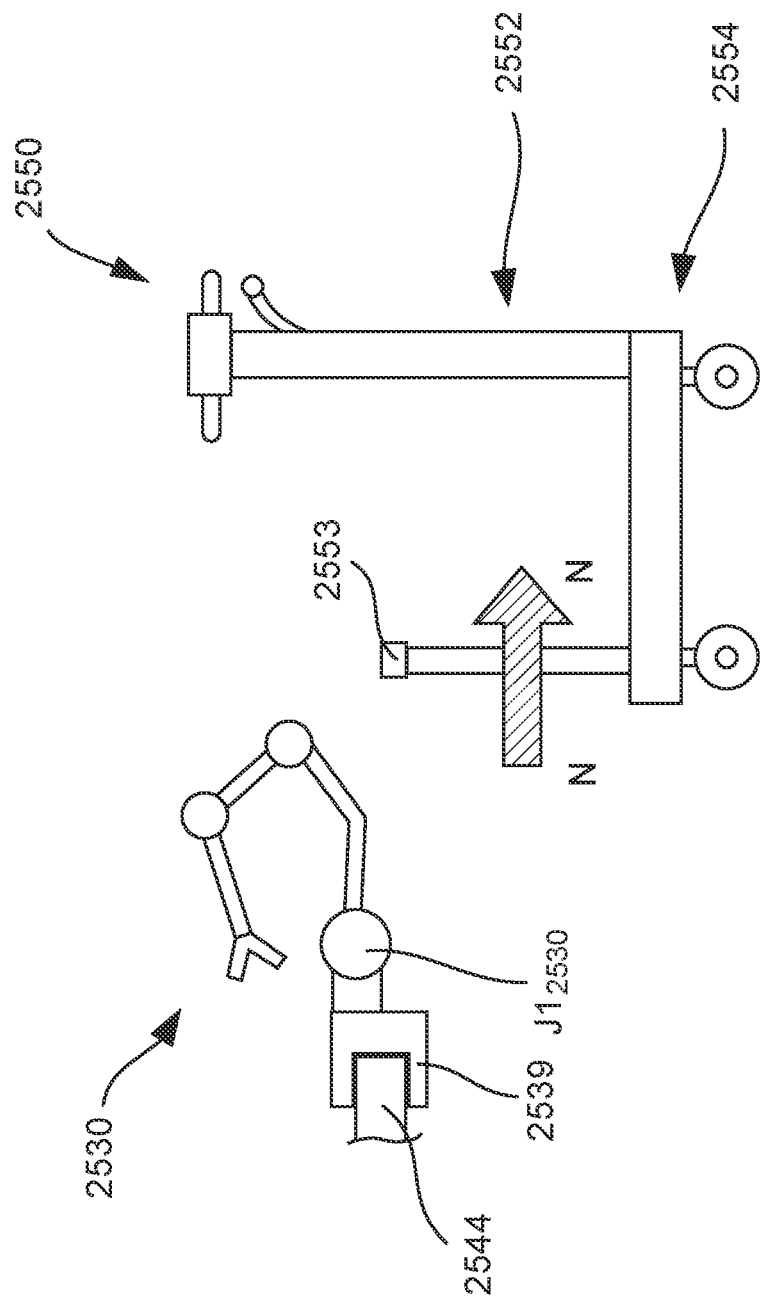

In use, the robotic arm 2530 can be maintained in a folded, storage position within the arm container 2552, as shown in the configuration of FIG. 20A. The arm cart 2550 can be moved such that the arm cart 2550 is adjacent the surgical table 2500 and the coupling member 2539 is engaged with the coupling member 2544. A user can then use the wireless hand control 2573 to communicate with the robotic arm 2530 and initiate movement of the robotic arm 2530 along arrow M-M from the folded, storage position to the deployed position, as shown in FIG. 20B. In some embodiments, the movement of the robotic arm 2530 can be powered by power provided from the surgical table 2500 to the robotic arm 2530 via the coupling member 2539, causing one or more portions of the robotic arm 2530 to rotate relative to at least one other portion of the robotic arm 2530 around one or more joints of the robotic arm 2530. After the robotic arm 2530 has moved into the deployed configuration (and out of the way of movement of the arm cart 2530), the arm cart 2530 can be pulled away from the surgical table 2500 and the robotic arm 2530, such as is shown by arrow N-N in FIG. 20C.

In addition, although not necessarily described for each embodiment, any of the embodiments described here.

in can include an adapter with more than two link members or only one link member. The various embodiments of a robotic surgical system described herein can include a table top on which a patient can be disposed, an adapter, and one or more link members. As described above, in some embodiments, the robotic arm can be incorporated into the adapter (e.g., an adapter/robotic arm assembly) and be coupled to a surgical table or be couplable to a surgical table. The adapters and the robotic arms (or in the case of an adapter/robotic arm assembly) can include one or more links or link members to allow for movement of the adapter and/or arms about and/or along the X, Y, and/or Z axes, to a desired location relative to the table top and/or relative to a patient disposed thereon.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The invention claimed is:

1. An apparatus comprising:
a surgical robotic arm having a coupler; and
a cart that includes:
 a movable base;
 a container coupled to the movable base; and
 an arm support releasably couplable to the surgical robotic arm and movably coupled to the movable base to move the surgical robotic arm, wherein the arm support is configured to move the surgical robotic arm between a first position in which the surgical robotic arm is at least partially within the container and a second position in which the coupler is engageable with a surgical table.

2. The apparatus of claim 1, wherein the arm support is configured to move the surgical robotic arm along a translation path and configured to rotate the surgical robotic arm about an axis.

3. The apparatus of claim 1, wherein the arm support is a first arm support and the surgical robotic arm is a first surgical robotic arm, wherein the arm cart further comprises a second arm support releasably couplable to a second surgical robotic arm and movably coupled to the movable base such that both the first and second surgical robotic arms are individually movable with respect to the movable base.

4. The apparatus of claim 1, wherein, while in the first position, the entire surgical robotic arm is contained within the arm container except for the coupler that is at least partially disposed outside of the arm container.

5. The apparatus of claim 1, wherein the arm support is linearly movable to move the surgical robotic arm between the first and second positions.

6. The apparatus of claim 1, wherein the arm support is rotationally movable to rotate the arm between the first and second positions.

7. The apparatus of claim 1, wherein the arm cart is a first arm cart that is configured to couple to a second arm cart that is of similar shape and size of the first arm cart, enabling both arm carts to move on a support surface in unison.

8. The apparatus of claim 7 further comprising a first coupler that is configured to releaseably couple to a second coupler of the second arm cart.

9. An arm cart for a surgical robotic arm, the arm cart comprising:
a movable base;
an arm container coupled to the movable base and in which at least a portion of the surgical robotic arm may be housed; and
an arm support releasably couplable to the surgical robotic arm and movably coupled to the movable base to move the surgical robotic arm.

10. The arm cart of claim 9, wherein the arm support is configured to move the surgical robotic arm along a translation path and configured to rotate the surgical robotic arm about an axis.

11. The arm cart of claim 9, wherein the arm support is a first arm support and the surgical robotic arm is a first surgical robotic arm, wherein the arm cart further comprises a second arm support releasably couplable to a second surgical robotic arm and movably coupled to the movable base such that both the first and second surgical robotic arms are individually movable.

12. The arm cart of claim 9, wherein the arm support is configured to move the surgical robotic arm between a first position in which the surgical robotic arm is within the arm container and a second position in which a coupler of the surgical robotic arm is engageable with a surgical table.

13. The arm cart of claim 12, wherein, while in the first position, the entire surgical robotic arm is housed within the arm container except for the coupler that is at least partially disposed outside of the arm container.

14. The arm cart of claim 12, wherein the arm support is linearly movable to move the surgical robotic arm between the first and second positions.

15. The arm cart of claim 12, wherein the arm support is rotationally movable to rotate the arm between the first and second positions.

16. The arm cart of claim 9, wherein the arm cart is a first arm cart that is configured to couple to a second arm cart that is of similar shape and size of the first arm cart, enabling both arm carts to move on a support surface in unison.

17. The arm cart of claim 16 further comprises a first coupler that is configured to releaseably couple to a second coupler of the second arm cart.

18. An arm cart for a surgical robotic arm, the arm cart comprising:
a movable base; and
a first arm support and a second arm support that are both coupled and stationary relative to the movable base, wherein the surgical robotic arm is held in position on the first and second arm supports by gravity.

19. The arm cart of claim 18, wherein the first arm supports holds a first portion of the surgical robotic arm and the second arm support holds a second portion of the surgical robotic arm, wherein the first portion of the surgical robotic arm comprises a joint that is configured to move the surgical robotic arm between a first position in which both the first and second arm supports hold the surgical robotic arm in position and a second position in which the surgical robotic arm is only supported by the first arm support.

20. The arm cart of claim 18, wherein a first height of the first arm support from the movable base is greater than a second height of the second arm support from the movable base.

* * * * *